US010653805B2

(12) United States Patent
Reiner et al.

(10) Patent No.: US 10,653,805 B2
(45) Date of Patent: *May 19, 2020

(54) COMPOSITIONS AND METHODS FOR IN VIVO IMAGING

(71) Applicant: The General Hospital Corporation, Boston, MA (US)

(72) Inventors: Thomas Reiner, Weehawken, NJ (US); Edmund J. Keliher, Topsfield, MA (US); Ralph Weissleder, Peabody, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/147,370

(22) Filed: Sep. 28, 2018

(65) Prior Publication Data
US 2019/0201562 A1 Jul. 4, 2019

Related U.S. Application Data

(63) Continuation of application No. 15/581,386, filed on Apr. 28, 2017, now Pat. No. 10,117,954, which is a continuation of application No. 13/988,790, filed as application No. PCT/US2011/061856 on Nov. 22, 2011, now Pat. No. 9,649,394.

(60) Provisional application No. 61/419,929, filed on Dec. 6, 2010, provisional application No. 61/416,035, filed on Nov. 22, 2010.

(51) Int. Cl.
*A61K 51/00* (2006.01)
*A61M 36/14* (2006.01)
*A61K 51/04* (2006.01)
*A61K 49/00* (2006.01)
*A61K 51/12* (2006.01)

(52) U.S. Cl.
CPC ...... *A61K 51/0459* (2013.01); *A61K 49/0021* (2013.01); *A61K 51/1251* (2013.01)

(58) Field of Classification Search
CPC ............ A61K 51/0459; A61K 49/0021; A61K 51/1251
USPC ...................................................... 424/1.89
See application file for complete search history.

(56) References Cited

U.S. PATENT DOCUMENTS

| 6,903,098 B1 | 6/2005 | Lubisch et al. | |
| 9,649,394 B2* | 5/2017 | Reiner | A61K 49/0021 |
| 10,117,954 B2* | 11/2018 | Reiner | A61K 49/0021 |
| 2003/0044353 A1 | 3/2003 | Weissleder | |
| 2005/0059663 A1* | 3/2005 | Martin | A61K 31/00 514/248 |
| 2005/0249668 A1 | 11/2005 | Weissledeer et al. | |
| 2006/0093552 A1 | 5/2006 | Babich et al. | |
| 2006/0269942 A1 | 11/2006 | Kolb et al. | |
| 2007/0105835 A1 | 5/2007 | Kazantsev | |
| 2008/0076778 A1 | 3/2008 | Ossovskaya et al. | |
| 2008/0118432 A1* | 5/2008 | Bergstein | G01N 33/5073 424/1.49 |
| 2008/0181847 A1 | 7/2008 | Robillard et al. | |
| 2009/0098084 A1 | 4/2009 | Xu et al. | |
| 2011/0268654 A1 | 11/2011 | Hilderbrand et al. | |

FOREIGN PATENT DOCUMENTS

| WO | WO 2006067376 | 6/2006 | |
| WO | WO 2007/014420 | 7/2006 | |
| WO | WO-2008075040 A2 * | 6/2008 | ............. A61K 51/04 |
| WO | WO 2010048144 | 4/2010 | |
| WO | WO 2010051530 | 5/2010 | |

OTHER PUBLICATIONS

Adam et al. J. Nucl. Med. 2008, 49, 299P.
Arnold et al. Bioorg. Med. Chem. Lett. 18 (2008) 5867-5870.
Balcar et al., "Reaktivitat Von Stickstoff-Heterocyclen," Tet. Lett., 24:1481-1484 (1983) (with translated abstract).
Blackman et al., "Tetrazine ligation: fast bioconjugation based on inverse-electron-demand Diels-Alder reactivity," J. Am. Chem. Soc., 130:13518-13519 (2008).
Carpenter et al., "CellProfiler: image analysis software for identifying and quantifying cell phenotypes," Genome Biology, 7:R100 (2006).
Devaraj et al. Angew. Chem. Int. Ed. 2009, 48, 7013-7016.
Devaraj et al. Bioconjugate Chem. 2009, 20, 397-401.
Devaraj et al., "Bioorthogonal turn-on probes for imaging small molecules inside living cells," Angew. Chem., Int. Ed., 49:2869-2872 (2010).
Devaraj et al., "Fast and sensitive pretargeted labeling of cancer cells through a tetrazine/trans-cyclooctene cycloaddition," Angew. Chern., Int. Ed., 48:7013-7016, S7013/1-S7013/6 (2009).
Devaraj et al., "Tetrazine-based cycloadditions: application to pretargeted live cell imaging," Bioconjug. Chem., 19:2297-2299 (2008).
Faust et al. Bioconjugate Chem. 2008, 19, 1001-1008.
Ferraris, "Evolution of poly(ADP-ribose) polymerase-1 (PARP-1) inhibitors. From concept to clinic," J. Med. Chem., 53:4561-4584 (2010).
Haince and Hendzel, "PARP1-dependent kinetics of recruitment of MRE11 and NBS1 proteins to multiple DNA damage sites," J. Biol. Chem., 283:1197-1208 (2008).
Hassa, "The diverse biological roles of mammalian PARPS, a small but powerful family of poly-ADP-ribose polymerases," Front. Biosci., 13:3046-3082 (2008).
Hudnall et al. Chem. Commun. 2008, 4596-4597.
Hudnall et al. J. Fluorine Chem. 131 (2010) 1182-1186.
International Search Report and Written Opinion dated Dec. 14, 2012 issued in international application No. PCT/US2011/061856, 11 pgs.
Kaijzle et al. Clin. Cancer Res. 2007, 13, 3490-3497.
Keliher et al., "High-Yielding, Two-Step 18F Labeling Strategy for $^{18}$F-PARP1 Inhibitors," Chem. Med. Chern., DOI:10.1002/cmdc. 201000426 (2010).

(Continued)

*Primary Examiner* — Michael G. Hartley
*Assistant Examiner* — Sean R Donohue
(74) *Attorney, Agent, or Firm* — Fish & Richardson P.C.

(57) ABSTRACT

This document relates to compounds useful for targeting PARP1. Also provided herein are methods for using such compounds to detect and image cancer cells.

9 Claims, 15 Drawing Sheets

(56) References Cited

OTHER PUBLICATIONS

Li et al. Biorg. Med. Chem. Lett. 2006, 16, 794-797.
Malpica et al., "Applying watershed algorithms to the segmentation of clustered nuclei," Cytometry, 28:289-297 (1997).
Meder et al., "PARP-1 and PARP-2 interact with nucleophosmin/B23 and accumulate in transcriptionally active nucleoli," J. Cell Sci., 118:211-222 (2005).
Menear et al., "4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1," J. Med. Chem., 51:6581-6591 (2008).
Nosho, "Overexpression of poly(ADP-ribose) polymerase-1 (PARP-1) in the early stage of colorectal carcinogenesis," Eur. J. Cancer, 42:2374-2381 (2006).
Otsu, "A Threshold Selection Method from Gray-Level Histograms," IEEE Trans. Sys. Man. Cyber., 9:62-66 (1979).
Pipkorn et al., "Inverse-electron-demand Diels-Alder reaction as a highly efficient chemoselective ligation procedure: synthesis and function of a BioShuttle for temozolomide transport into prostate cancer cells," J. Pept. Sci., 15:235-241 (2009).
Reiner et al., "Bioorthogonal small-molecule ligands for PARP1 imaging in living cells," Chern. Bio. Chem., 11:2374-2377 (2010).
Reiner et al., "Synthesis and In Vivo Imaging of a 18F-Labeled PARP1 Inhibitor Using a Bioorthogonal Scavenger-Assisted High Performance Method," Angew Chem Int Ed Engl. 50(8);1922-25 (2011).
Riss et al. J. Label. Cnnpd Radiopharm. 2009, 52, 576-579.
Rouleau and Poirier, "PARP inhibition: PARP1 and beyond," Nature Rev. Cancer, 10:293-301 (2010).
Royzen et al., "A photochemical synthesis of functionalized trans-cyclooctenes driven by metal complexation," J. Am. Chem. Soc., 130:3760-3761 (2008).
Sauer et al., "Umsetzungen von 1.2.4.5-Tetrazinen mit Olefinen. Zur struktur von Dihydropyridazinen," Chem. Ber., 998:1435-1445 (1965) (with translated abstract).
Thalhammer et al., "Reaktivitat Einfacher Offenkettiger Und Cyclischer Dienophile Bei Diels-Alder-Reaktionen Mit Inversem Elektronenbedarf," Tet. Lett., 47:6851-6854 (1990) (with translated abstract).
Thurber et al., "Effect of Small-Molecule Modification on Single-Cell Pharmacokinetics of PARP Inhibitors," Molecular Cancer Therapeutics, 13:986-995 (2014).
Zaremba, "Poly(ADP-ribose) polymerase-1 polymorphisms, expression and activity in selected human tumour cell lines," Br. J. Cancer, 101:256-262 (2009).
Zhang et al. Curr. Top. Med. Chem. 2007, 7, 1817-1828.
Zhong et al. B. J. Can. 2009, 101, 2015-2022.

\* cited by examiner

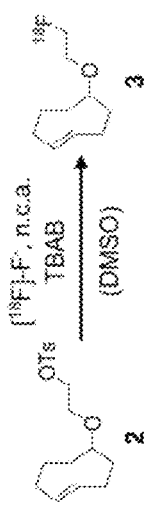
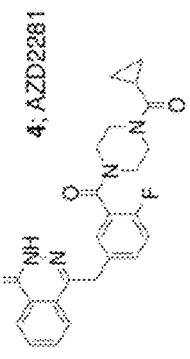
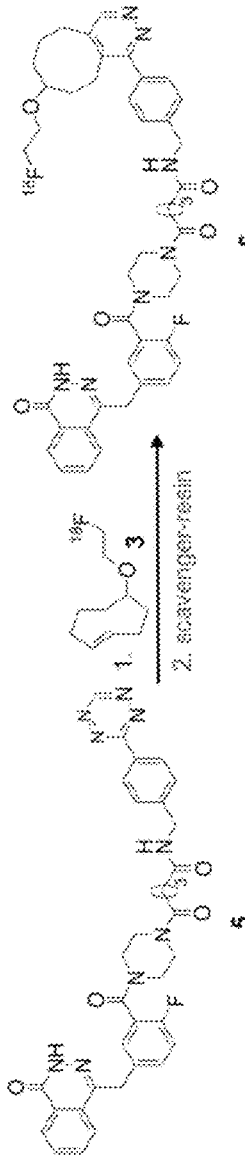
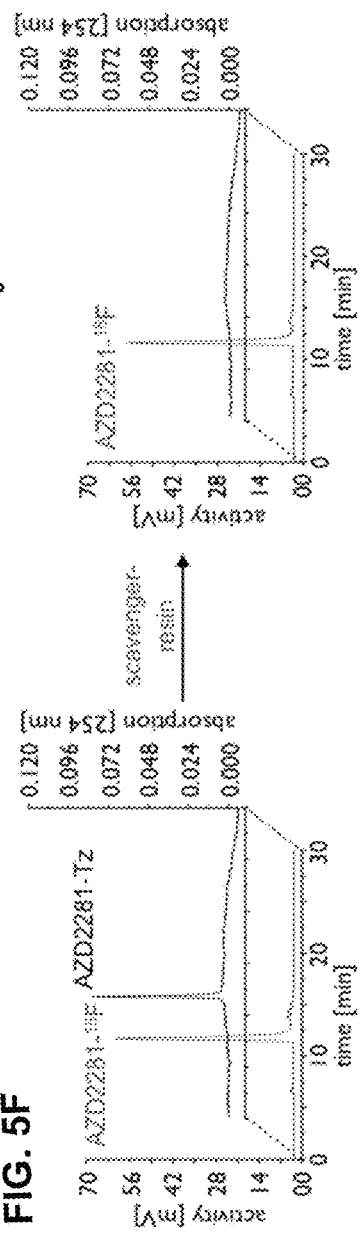
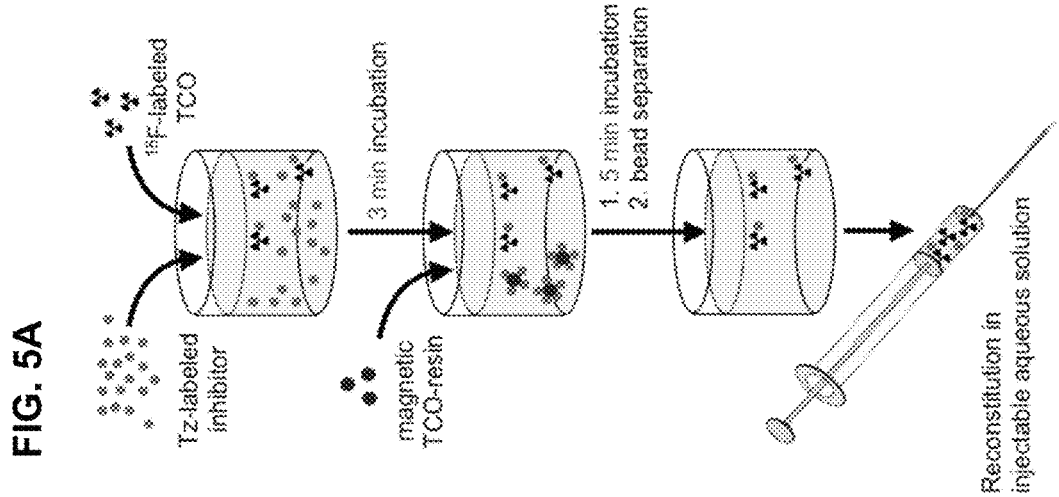
FIG. 5A
FIG. 5B
FIG. 5C
FIG. 5D
FIG. 5E
FIG. 5F

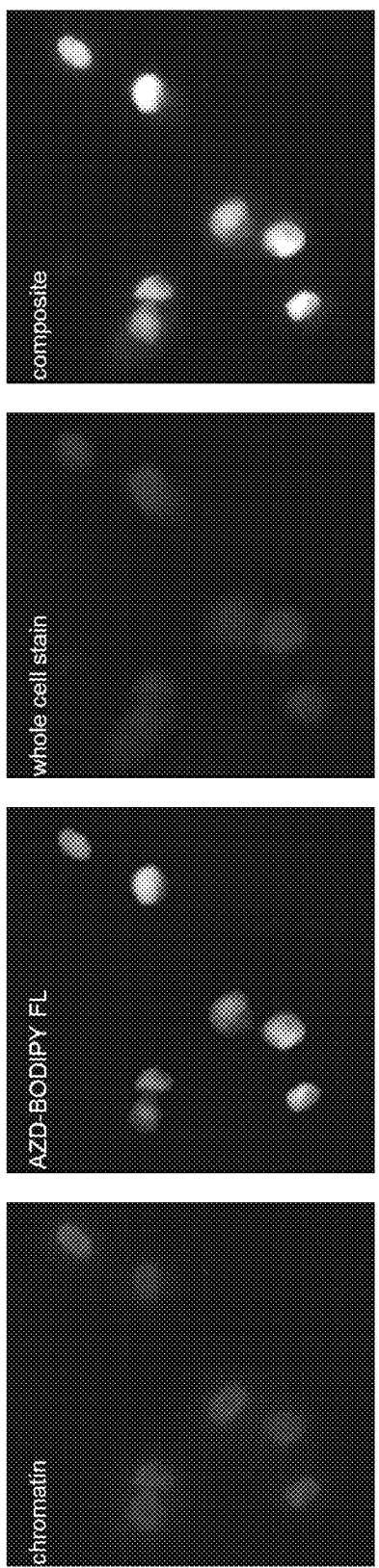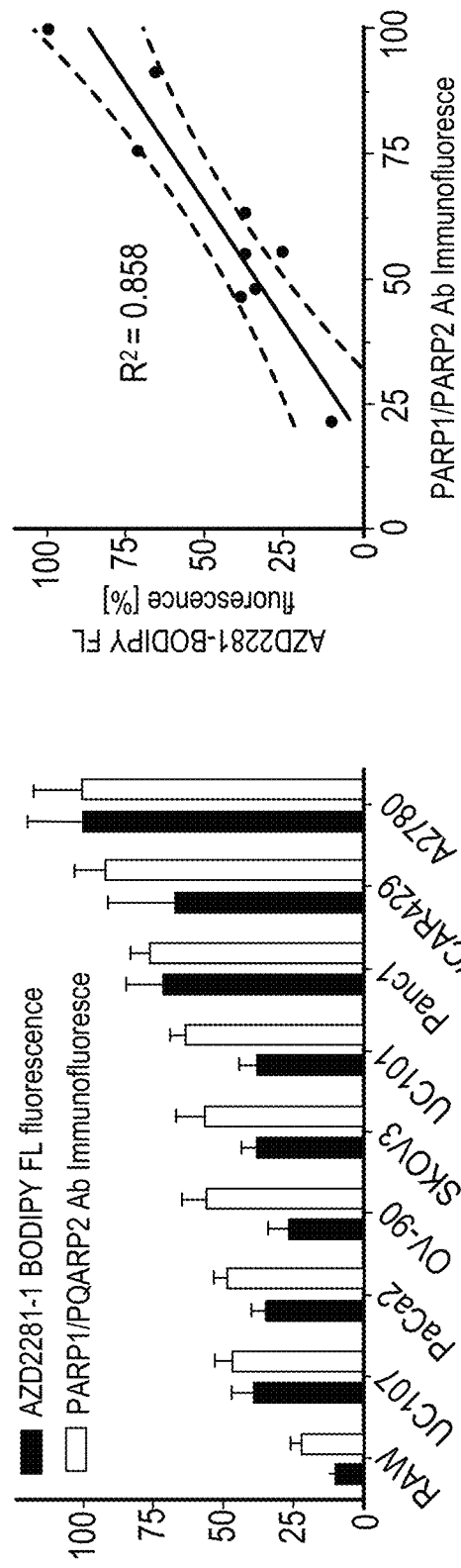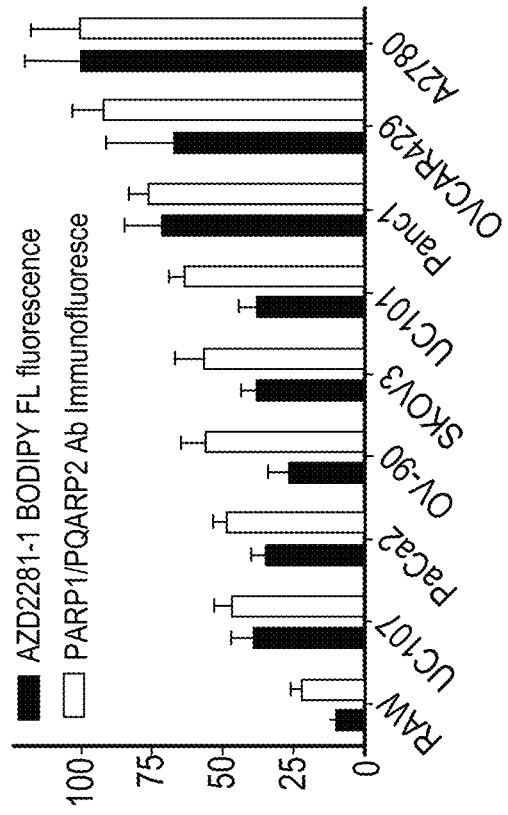
FIG. 9A
FIG. 9B
FIG. 9C

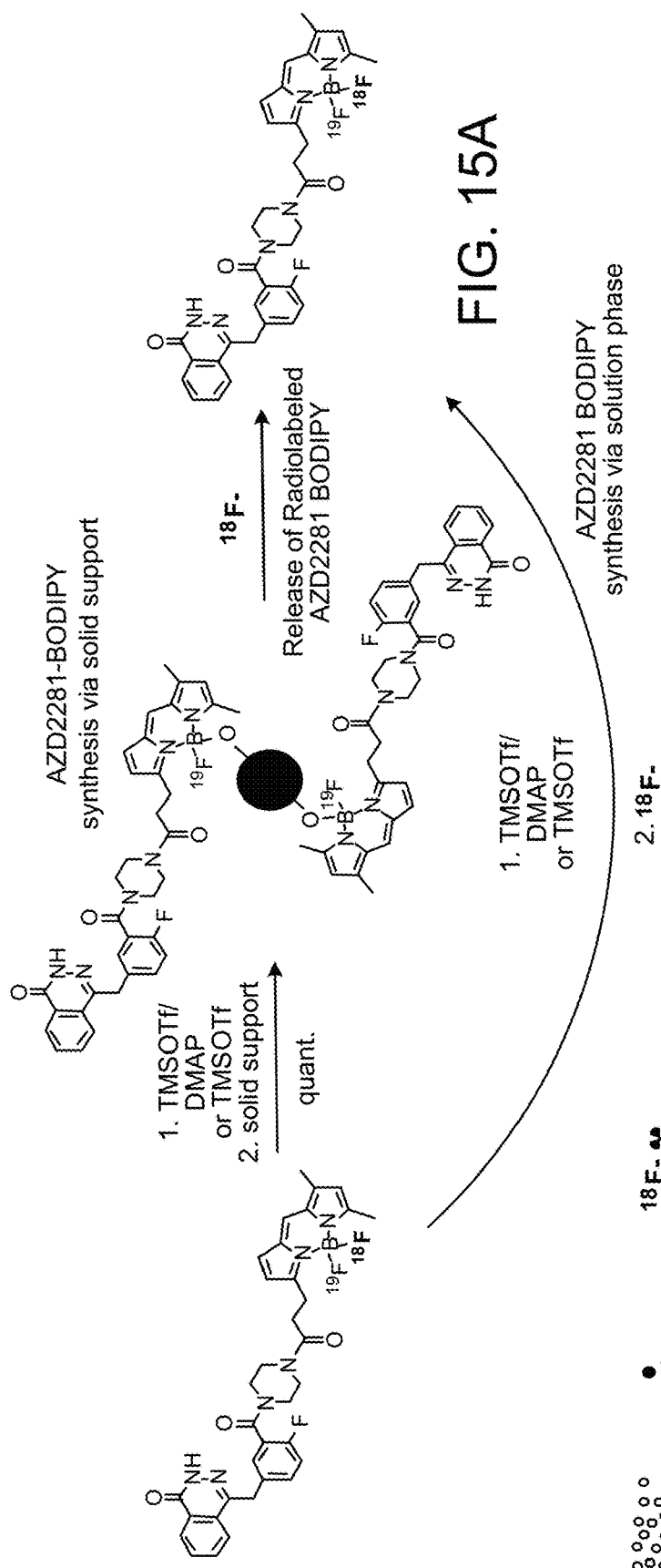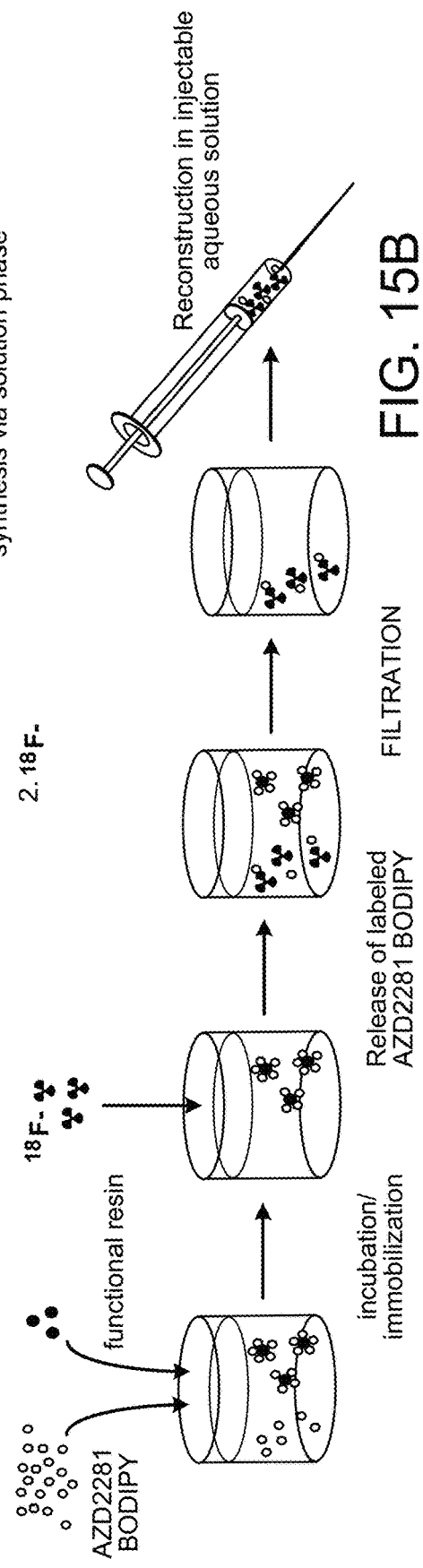
FIG. 15A
FIG. 15B

COMPOSITIONS AND METHODS FOR IN VIVO IMAGING

CLAIM OF PRIORITY

This application is a continuation of U.S. patent application Ser. No. 15/581,386, filed on Apr. 28, 2017, which is a continuation of U.S. patent application Ser. No. 13/988,790, filed with a 371 filing date of Aug. 2, 2013, which is a U.S. National Phase application under 35 U.S.C. § 371 of International Patent Application No. PCT/US2011/061856, filed on Nov. 22, 2011, which claims priority under 35 U.S.C. § 119(e) to U.S. Patent Application Ser. Nos. 61/419,929, filed on Dec. 6, 2010, and 61/416,035, filed on Nov. 22, 2010, all of which are incorporated herein by reference in their entireties.

STATEMENT REGARDING FEDERALLY SPONSORED RESEARCH OR DEVELOPMENT

The present invention was made with government support under Grant Nos. P50 CA86 355 and NIBI-RO1 EB-010 011 awarded by the National Cancer Institute; and Grant No. NIGMS T32 GM008313 awarded by the National Institutes of Health. The Government has certain rights in the invention.

TECHNICAL FIELD

This document relates to detectable compounds that bind PARP1. Also provided herein are methods for using such compounds to detect and image cells containing PARP1, for example, cancer cells.

BACKGROUND

Poly(ADP-ribose) polymerase 1 (PARP1) is an important cellular protein that senses DNA damage and initiates the base excision repair pathway. DNA damage (e.g., strand breaks) occurs during each cell cycle and must be repaired for a cell to survive. In cells undergoing rapid division and proliferation, such as cancer cells, levels of PARP1 are significantly increased. This is particularly true in cells lacking other DNA repair enzymes, such as cells lacking function BRCA1 and BRCA2.

SUMMARY

Described herein are detectable compounds that bind PARP1. Also provided herein are methods and materials for using such compounds to image cells containing PARP1, for example, cancer cells. In some cases, such cells overexpress PARP1. For example, a compound of Formula (1) can be used to detect or image a cancer cell in a subject through noninvasive imaging of the subject.

The methods and compositions provided herein provide several advantages. For example, one problem in the assessment of therapeutic efficacy of cancer therapies has been the inability to image PARP1 noninvasively at the whole-body level and to quantitate therapeutic inhibition. With the present technology it is possible to separate subjects into appropriate treatment groups and to detect emerging resistance. Given the emerging importance of positron emission tomography (PET) imaging in preclinical and clinical settings, and evidence that fluorescently labeled PARP1 inhibitors can be used for cellular imaging, the compounds provided herein function as detectable probes for whole-body PARP1 imaging. In some embodiments, a compound provided herein is useful for measuring inhibition of PARP1 by emerging therapeutic PARP1 inhibitors.

In addition to the advantage described above, one way to identify useful imaging agents is to empirically test a series of different agents in vivo. This approach, however, places considerable demands on the labeling of each compound. To overcome these lengthy sequential optimization procedures for each individual compound, provided herein is one such approach based on the combination of [4+2] inverse electron demand Diels-Alder cycloadditions; its utility is shown by the development of the novel PARP1 imaging agents described herein.

This disclosure provides a compound of Formula (I):

$$P-L_n-T_m-D$$

or a pharmaceutically acceptable salt form thereof,
wherein:
P is a PARP1 inhibitor;
L is a linker;
T is:

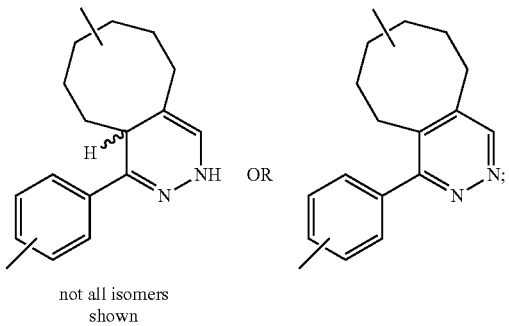

not all isomers shown

D is a detectable agent;
m is 0 or 1; and
n is 0 or 1.

In some embodiments, P is selected from the group consisting of: benzamide, quinolone, dihydroisoquinolinone, isoquinolinone, isoquinolone, benzopyrone, cyclic benzamide, benzimidazole, indole, isoindolinone, nicotinamide, 3-AB, phthalazinone, and quinazolinone. For example, P can be selected from the group consisting of: AZD2281 (olaparib), AG014699 (rucaparib), ABT888 (veliparib), BSI201 (iniparib), BSI101, DR2313, FR 247304, GPI15427, GPI16539, MK4827, NU1025, NU1064, NU1085, PD128763, PARP Inhibitor II (INH2BP), PARP Inhibitor III (DPQ), PARP Inhibitor VIII (PJ34), PARP Inhibitor IX (EB-47), and TIQ-A. In some embodiments, P is AZD2281.

In some embodiments, the compound of Formula (I) is a compound of Formula (II):

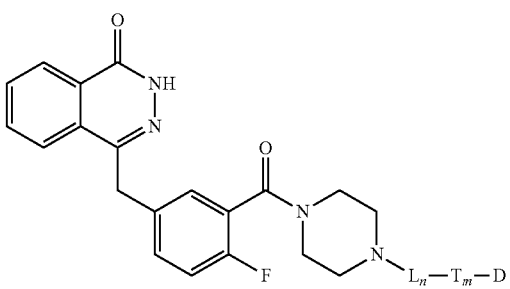

or a pharmaceutically acceptable salt form thereof, wherein:
L is a linker;
T is:

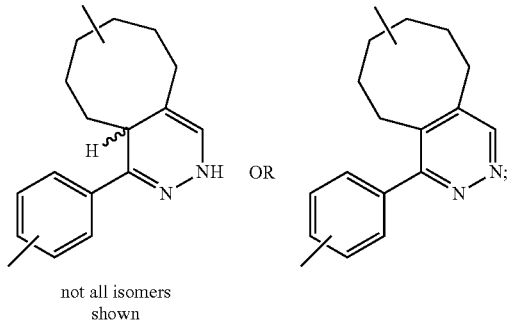

not all isomers shown

D is a detectable agent;

m is 0 or 1; and n is 0 or 1.

In some embodiments, D comprises one or more of organic small molecules, inorganic compounds, nanoparticles, enzymes or enzyme substrates, fluorescent materials, luminescent materials, bioluminescent materials, radioactive materials, and contrast agents. For example, D can comprise a radioactive material, a fluorescent material, or a mixture thereof.

Non-limiting examples of a compound of Formula (I) include:

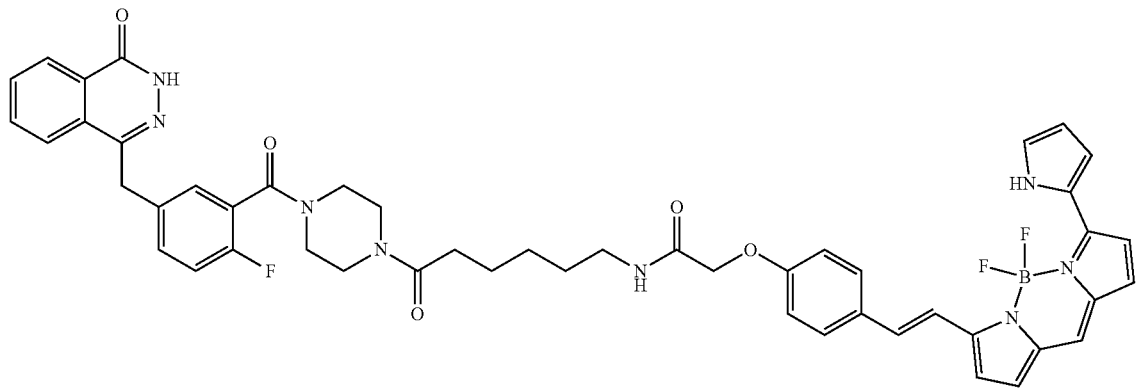

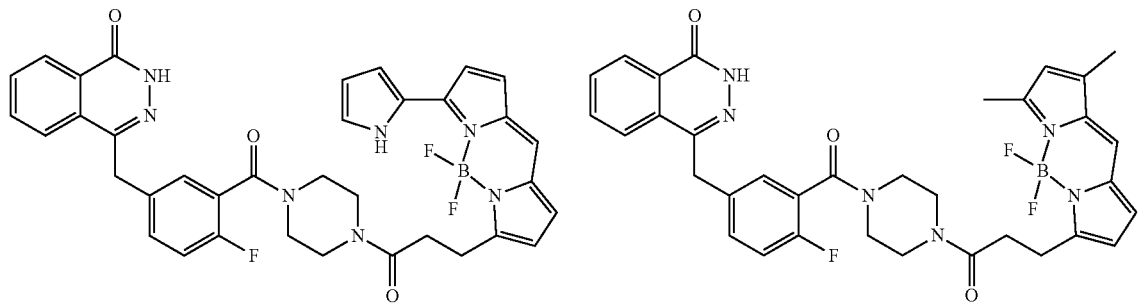

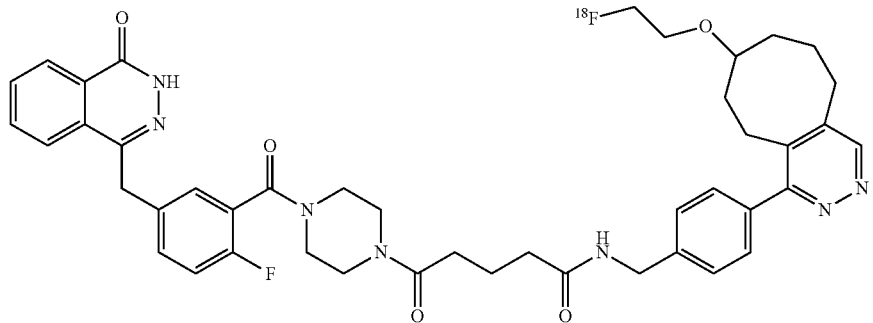

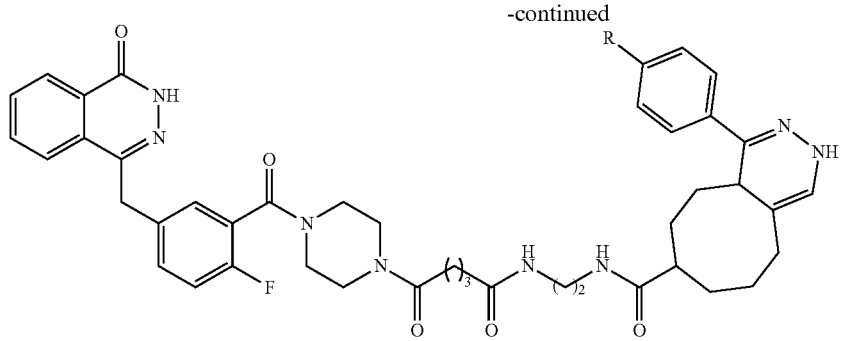

-continued

15 wherein R is Texas Red, a cyanine dye, Alexafluor-680, a BODIPY dye, a xanthene derivatives, a naphthalene dye, a courmarin derivative, an oxadiazole derivative, a pyrene derivative, an oxazine derivative, an acridine derivative, an arylmethine derivative, and a tetrapyrrole derivative.

In some embodiments, the compound of Formula (1) is selected from the group consisting of:

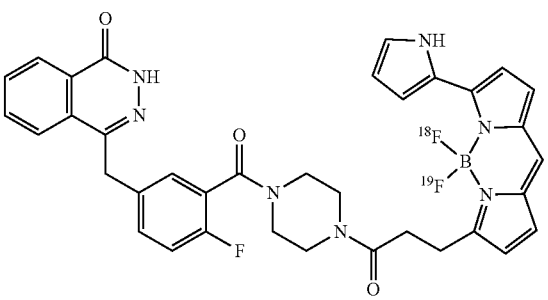

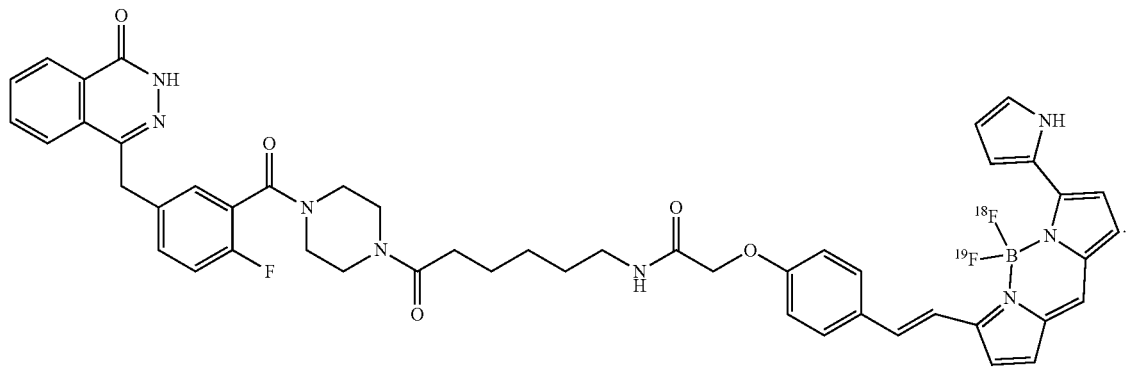

In some embodiments, a compound of Formula (1) is:

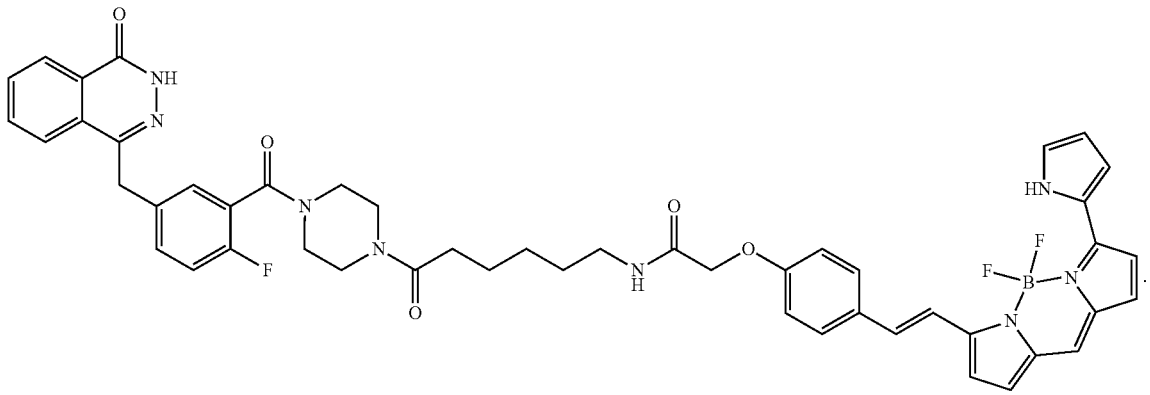

For example, the compound of Formula (1) can be:

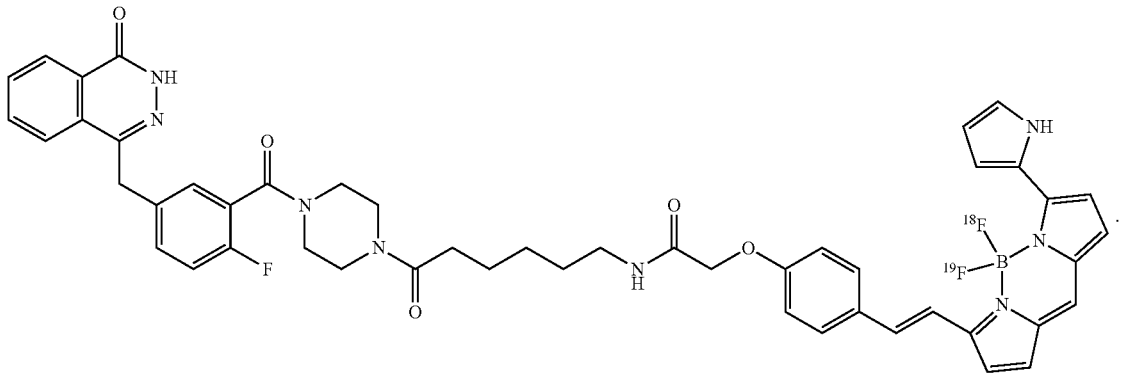

Also provided herein is a pharmaceutical composition comprising a compound of Formula (I), or a pharmaceutically acceptable salt form thereof.

The compounds provided herein are useful for detecting a cancer in a subject. In some embodiments, the method comprises: administering to a subject an effective amount of a compound of Formula (I), or a pharmaceutically acceptable salt form thereof, and detecting the detectable agent in the subject. In some embodiments, the compound of Formula (1) is administered before and after surgical removal of the cancer.

In some embodiments, detecting the detectable agent comprises using one or more of histochemistry, fluorescence detection, chemiluminescence detection, bioluminescence detection, magnetic resonance imaging, nuclear magnetic resonance imaging, positron emission tomography, single-photon emission computed tomography, X-ray imaging, X-ray computed tomography, ultrasound imaging, or photoacoustic imaging.

In some embodiments, the cancer is selected from the group consisting of: pancreatic cancer, ovarian cancer, and breast cancer.

Also provided herein is a method for imaging a cancer cell, the method comprising: contacting a cancer cell with an effective amount of a compound of Formula (I), or a pharmaceutically acceptable salt form thereof, and imaging the cell.

Further provided herein is a method for monitoring the cancer treatment of a patient, the method comprising: (a) administering to the patient, prior to a treatment, an effective amount of a compound of Formula (I), or a pharmaceutically acceptable salt form thereof, and imaging the patient; (b) administering to the patient, at a point following treatment, an effective amount the compound of Formula (I) and imaging the patient; and (c) comparing the image collected in step (a) with the image collected in step (b) to monitor the treatment. In some embodiments, the treatment comprises administration of an anti-cancer agent. In some embodiments, the method further comprises: administering to the patient an effective amount of the compound of Formula (I) during treatment and imaging the patient.

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "subject," as used herein, includes both humans and other animals, particularly mammals. Thus, the methods are applicable to both human therapy and veterinary applications. In some embodiments, the subject is a mammal, for example, a primate. In some embodiments, the subject is a human.

An "effective" amount of a compound provided herein is typically one which is sufficient to allow detection of the compound (e.g., detection of a cancer cell) and may vary according to the detection method utilized and the detection limit of the compound.

The term, "compound," as used herein is meant to include all stereoisomers, geometric isomers, constitutional isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2A shows AZD2281-TCO reacted with Texas Red-Tz; speckles outside the cells, presumably resulting from precipitated Texas Red-Tz (8), were removed.

FIG. 5A is a schematic illustrating the synthesis of $^{18}$F-AZD2281 (6); $^{18}$F-labeled TCO 3 and AZD2281-Tz (5) were combined and incubated for 3 minutes; magnetic TCO-scavenger resin was added, incubated for 5 minutes, and removed; purified $^{18}$F-AZD2281 was reconstituted and brought into an injectable volume. FIG. 5B illustrates the synthesis of the magnetic TCO-scavenger resin from amine-decorated beads and NHS-activated TCO (1). FIG. 5C illustrates the synthesis of $^{18}$F-labeled TCO (3). FIG. 5D provides the structure of AZD2281 (4). FIG. 5E shows the synthesis and structure of $^{18}$F-AZD2281 ((6); only one isomer shown). FIG. 5F illustrates the radioactivity and absorption traces of the $^{18}$F-AZD2281 reaction mixture before and after purification with the magnetic TCO-scavenger resin.

FIG. 7A shows combined PET/CT scans of a nontumor-bearing mouse injected with $^{18}$F-AZD2281 recorded 10, 30, and 50 minutes after injection. FIG. 7B shows the three-dimensional reconstruction of a tumor-bearing animal injected with $^{18}$F-AZD2281 with and without pre-injection of AZD2281 (bladder segmented out for clarity). FIG. 7C illustrates quantification of uptake through the tumor in hind legs with and without intraperitoneal pre-injection of unlabeled AZD2281 (SUV: standardized uptake value).

FIG. 9A shows that AZD2281-BODIPY FL (green) localizes with the nucleus (as confirmed with the red signal, Chromatin (essentially a DNA stain)). FIGS. 9B and 9C show the amount of fluorescence present in cells using AZD2281 and a PARP1/PARP2 antibody.

FIGS. 15A and 15B are schemes illustrating the preparation of $^{18}$F-AZD2281-BODIPY FL compounds.

DETAILED DESCRIPTION

Figure 1A:
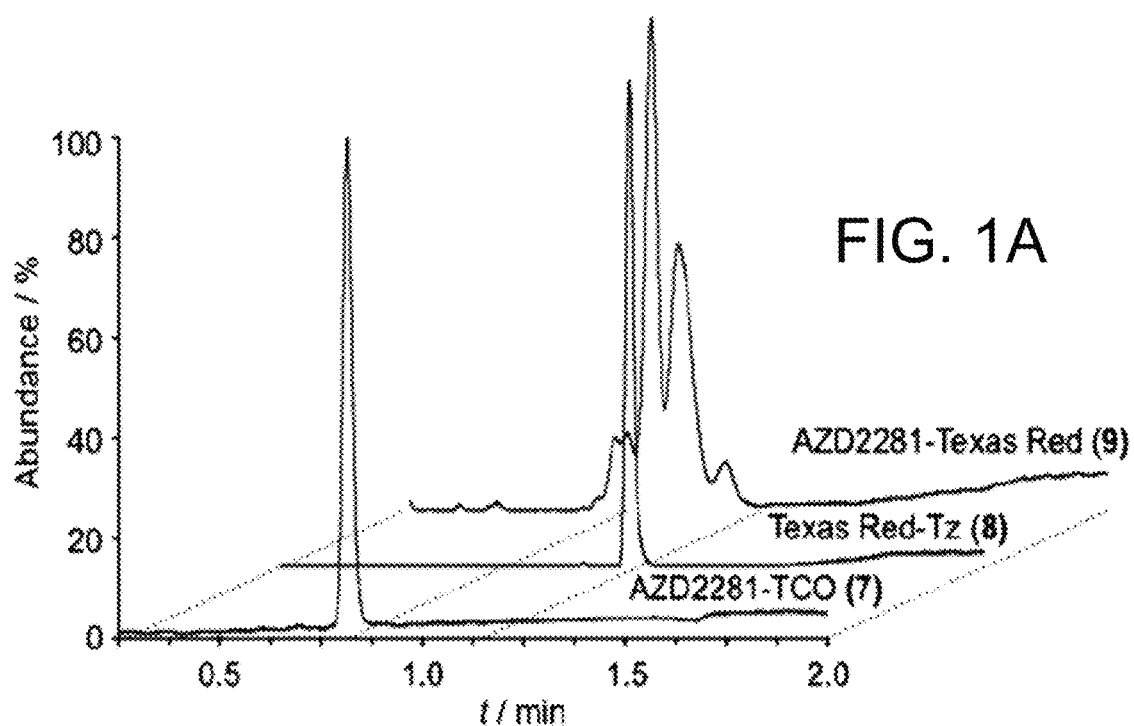
FIG. 1A is an HPLC trace of AZD2281-TCO (7); Texas Red-tetrazine (8; one isolated stereoisomer shown); and AZD2281-Texas Red (9; crude reaction mixture).

Described herein are detectable compounds that bind PARP1. Also provided herein are methods and materials for using such compounds to image cells containing PARP1, for example, cancer cells. In some cases, such cells overexpress PARP1. For example, a compound of Formula (1) or (2) can be used to detect or image a cancer cell, e.g., in a living subject, e.g., through noninvasive imaging of the subject.

Compounds

Provided herein are compounds of Formula (1):

P-L$_n$-T$_m$-D or a pharmaceutically acceptable salt form thereof, wherein:
P is a PARP1 inhibitor;
L is a linker;
T is:

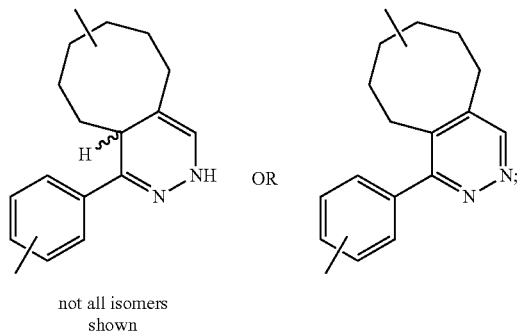

not all isomers shown

D is a detectable agent;
m is 0 or 1; and
n is 0 or 1.

A PARP1 inhibitor can include any compound which inhibits or reduces the activation of PARP1. For example, PARP1 activation in response to DNA breaks and/or involved in cell death. PARP1 inhibitors include compounds from various chemical classes including benzamides, quinolones, dihydroisoquinolinones, isoquinolinones, isoquinolones, benzopyrones, cyclic benzamides, benzimidazoles, indoles, isoindolinones, nicotinamides, 3-AB, phthalazinones, quinazolinones, phenanthridinones, and zinc-fingers. In some embodiments, a PARP1 inhibitor is selected from the group consisting of: AZD2281 (olaparib), AG014699 (rucaparib), ABT888 (veliparib), BSI201 (iniparib), BSI101, DR2313, FR 247304, GPI15427, GPI16539, MK4827, NU1025, NU1064, NU1085, PD128763, PARP Inhibitor II (INH2BP), PARP Inhibitor III (DPQ), PARP Inhibitor VIII (PJ34), PARP Inhibitor IX (EB-47), and TIQ-A. For example, a PARP1 inhibitor can be AZD2281.

In some embodiments, a compound of Formula (1) is a compound of Formula (2):

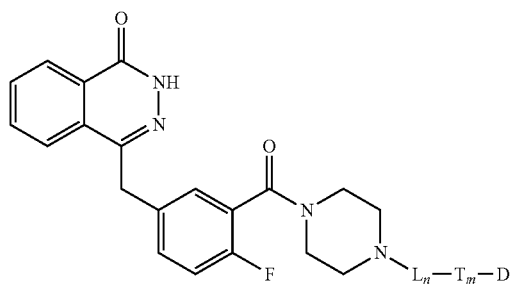

or a pharmaceutically acceptable salt form thereof, wherein:
L is a linker;
T is:

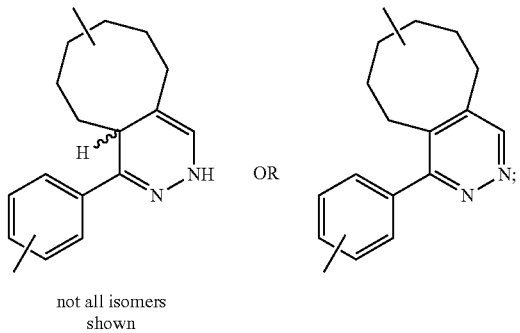

not all isomers shown

D is a detectable agent;
m is 0 or 1; and
n is 0 or 1.

Examples of detectable agents include various organic small molecules, inorganic compounds, nanoparticles, enzymes or enzyme substrates, fluorescent materials, luminescent materials, bioluminescent materials, chemiluminescent materials, magnetic materials, radioactive materials, and contrast agents. In some embodiments, the detectable agent is a radioactive material or a fluorescent material. Examples of suitable enzymes include horseradish peroxidase, alkaline phosphatase, beta-galactosidase, or acetylcholinesterase; examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl) aminohexanoic acid, succinimidyl ester (BODIPY® 650/665-X), 7-N,N-diethylaminocoumarin, sulforhodamine 101 acid chloride (Texas Red), VIVOTAG 680 (an amine-reactive near-infra-red fluorochrome, from VisEn Medical), umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{11}$C, $^{13}$N, $^{15}$O, $^{18}$F, $^{67}$Ga, $^{81m}$Kr, $^{82}$Rb, $^{86}$Y, $^{89}$Zr, $^{111}$In, $^{123}$I, $^{124}$I, $^{133}$Xe, $^{201}$Tl, $^{125}$I, $^{35}$S, $^{14}$C, or $^{3}$H, $^{64}$Cu, $^{99m}$Tc (e.g., as pertechnetate (technetate(VII), TcO$_4^-$) either directly or indirectly, $^{123}$I, or other radioisotope detectable by direct counting of radioemmission or by scintillation counting. In some embodiments, the radioactive material is complexed by a suitable ligand modality. Such ligands are well known in the art. For example, a ligand can include DTPA, DTPE, DOTA, NOTA, DO3A, DDPE, and DOTAGA. In some embodiments, a radioisotope is conjugated to the compound directly or indirectly via a linker (e.g., an alkyl or ether linker). In addition, contrast agents, e.g., contrast agents for MRI or NMR, for X-ray CT, Raman imaging, optical coherence tomography, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MI- ONs), and ultrasmall superparamagnetic iron oxide (US-PIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical))

When the compounds are enzymatically labeled with, for example, horseradish peroxidase, alkaline phosphatase, or luciferase, the enzymatic label is detected by determination of conversion of an appropriate substrate to product.

In some embodiments, the detectable agent is selected from the group consisting of: $^{18}$F, Texas Red, BODIPY FL, BODIPY 578, and BODIPY 650.

In vitro assays in which these compositions can be used include enzyme linked immunosorbent assays (ELISAs), immunoprecipitations, immunofluorescence, enzyme immunoassay (EIA), radioimmunoassay (RIA), and Western blot analysis.

Figure 14:
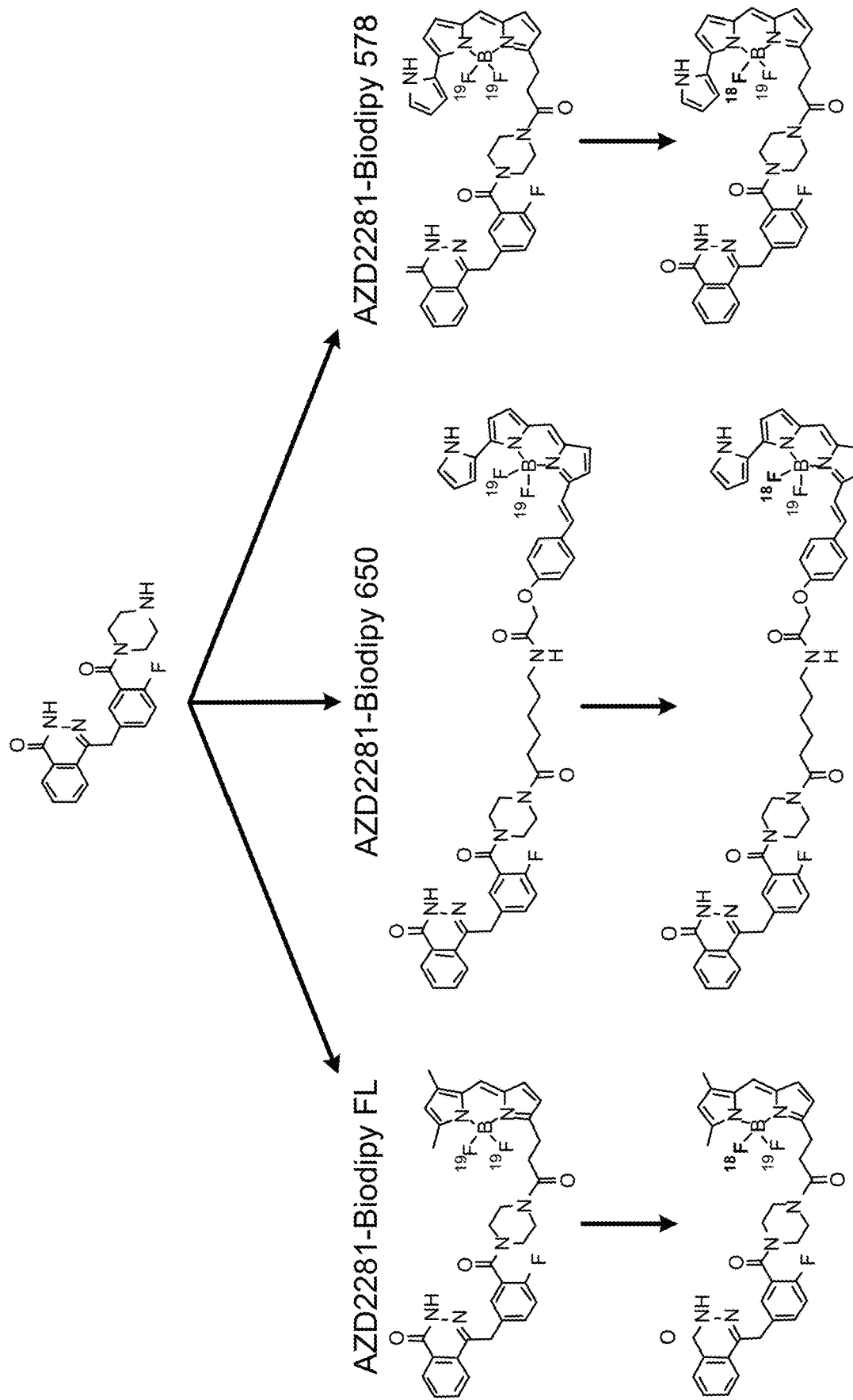
FIG. 14 illustrates various $^{18}$F-AZD2281-BODIPY compounds for in vivo imaging.

In some embodiments, a detectable agent comprises one or more of the detectable agents described above. For example, a fluorescent detectable agent can have one or more atoms replaced with one or more radionuclides. In some embodiments, a fluorophore comprising one or more fluorine atoms can have one or more of those fluorine atoms radioactively labeled with $^{18}$F. Non-limiting examples include $^{18}$F-BODIPY FL, $^{18}$F-BODIPY 578, and $^{18}$F-BODIPY 650. See, for example, FIG. 14.

The term "linker" as used herein refers to a group of atoms, e.g., 0-500 atoms, and can be comprised of the atoms or groups of atoms such as, but not limited to, hydrogen and carbon, e.g., methylene (—CH$_2$—), amino, amido, alkylamino, oxygen, polyethylene glycol (PEG), peptoid, sulfur, sulfoxide, sulfonyl, carbonyl, and imine. The linker can also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, saturated alkanes, alkyl ethers, alkyl diamines, and alkyl chains having one or more peptide bonds. In some embodiments, the linker is linked to the PARP1 inhibitor, the T moiety, or a detectable agent through a peptide bond. The linker must not interfere with the imaging methods or with the bioorthogonal conjugation reactions described herein.

Non-limiting examples of linkers provided herein include:

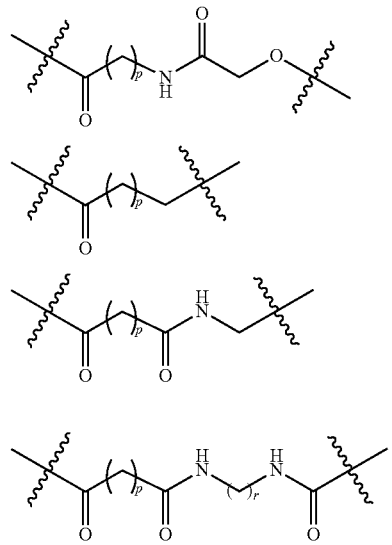

wherein each p is independently an integer from 1 to 20 (e.g., 1 to 15, 1 to 12, 1 to 10, 1 to 8, 1 to 5, 2 to 20, 4 to 20, 5 to 20, 8 to 20, 12 to 20, 15 to 20, 2 to 8, and 1 to 6);
and
r is an integer from 1 to 20 (e.g., 1 to 15, 1 to 12, 1 to 10, 1 to 8, 1 to 5, 2 to 20, 4 to 20, 5 to 20, 8 to 20, 12 to 20, 15 to 20, 2 to 8, and 1 to 6).

In some embodiments, p is an integer from 1 to 6 (e.g., 1, 2, 3, 4, 5, or 6). In some embodiments, r is an integer from 1 to 3 (e.g., 1, 2, or 3). In some embodiments, a linker is selected from the group consisting of:

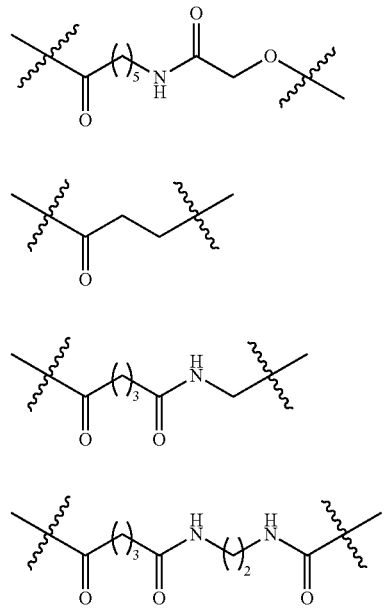

Non-limiting examples of a compound of Formula (1) or Formula (2) include:

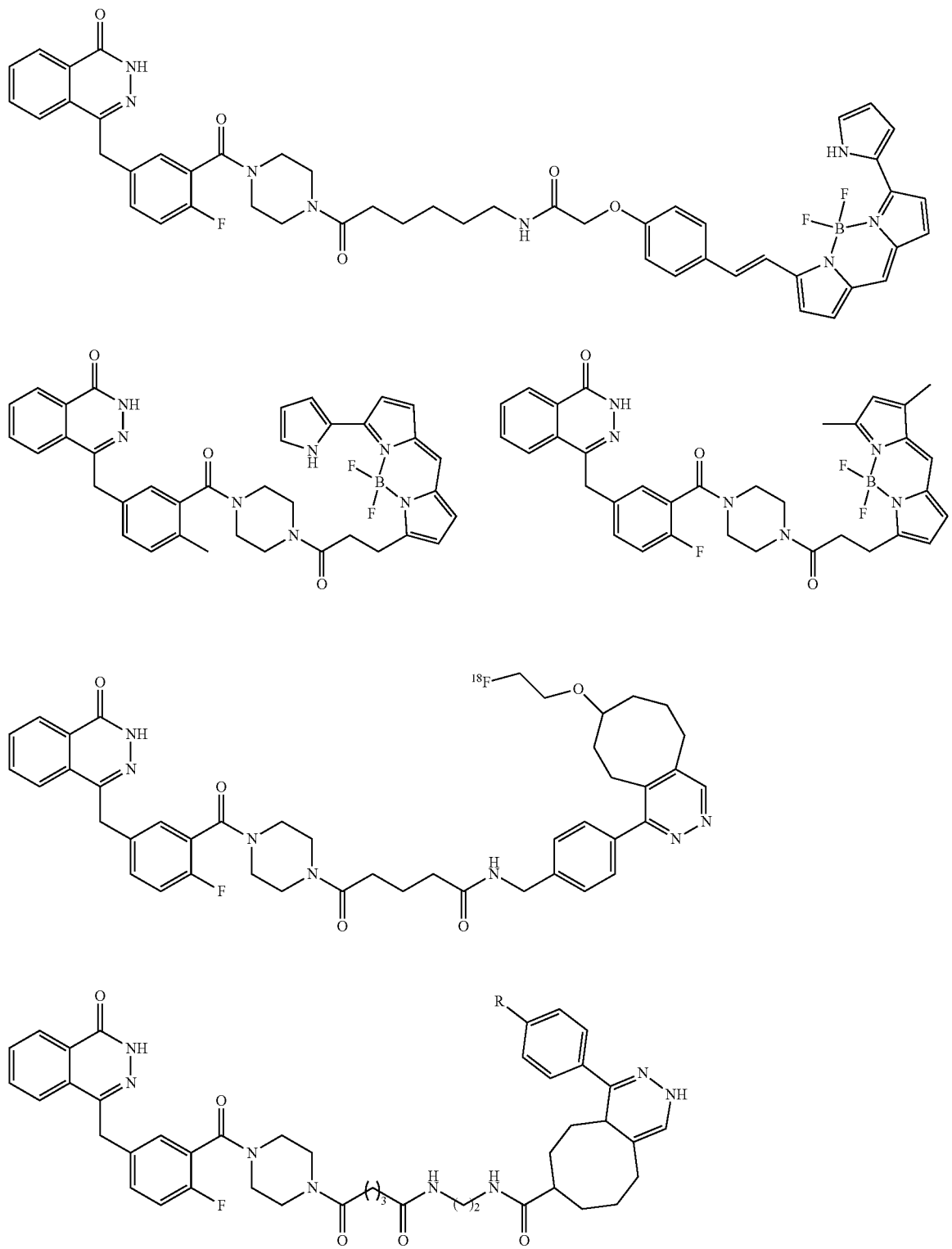

wherein R is Texas Red, cyanine dyes (e.g., VivoTag-680, Cy5), Alexafluor-680, BODIPY dyes (e.g., BODIPY-FL), Xanthene derivatives (e.g., Fluorescein), Naphthalene dyes (e.g., Dansyl), Courmarin derivatives, oxadiazole derivatives, pyrene derivatives, oxazine derivatives, acridine derivatives, arylmethine derivatives, tetrapyrrole derivatives. In some embodiments, R is Texas Red.

For example, a compound of Formula (1) or Formula (2) can include:
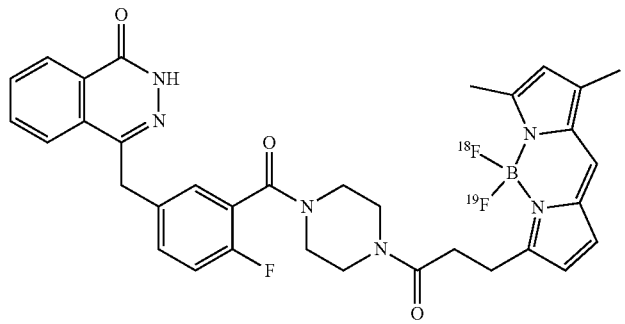
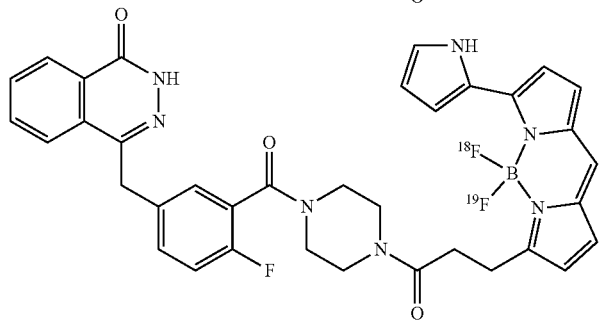
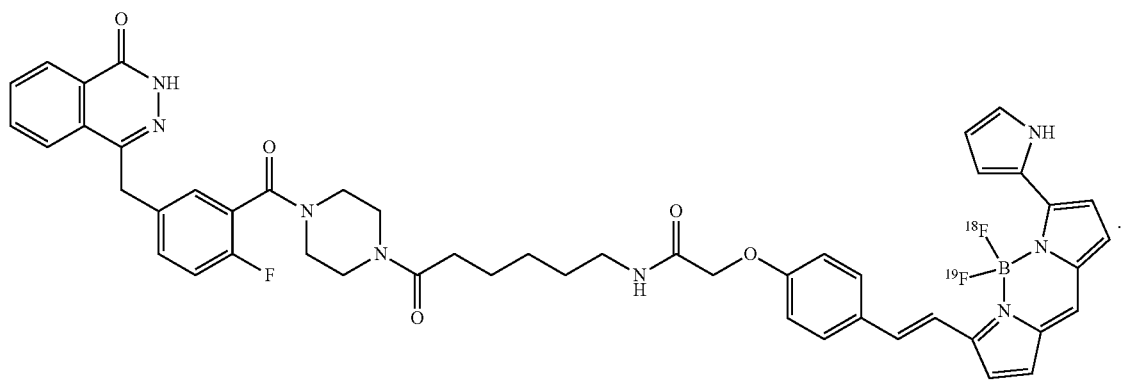
In some embodiments, the compound of Formula (1) or Formula (2) is:
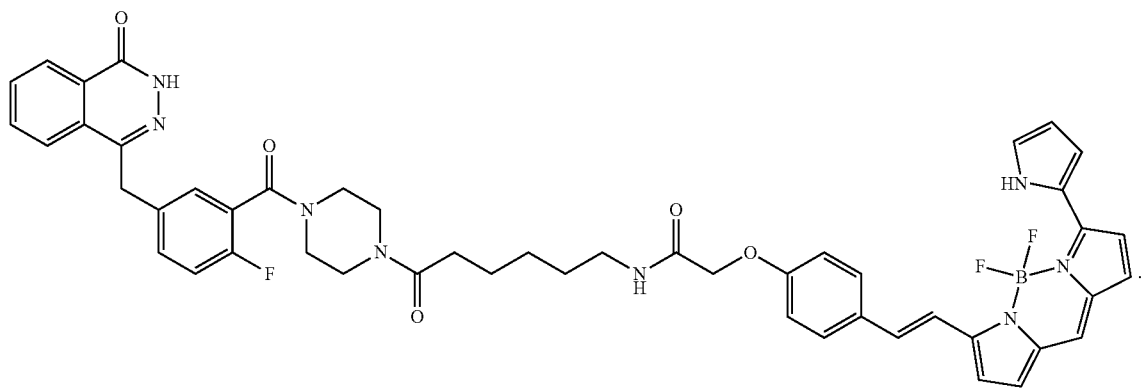

Compounds provided herein, including salts thereof, can be prepared using known organic synthesis techniques and can be synthesized according to any of numerous possible synthetic routes.

For example, AZD2281-Texas Red can be prepared, in part, as shown in the following scheme:

was attached to precursor (3), yielding the amine-functionalized AZD2281 derivative (4). Norbornene-functionalized AZD2281-NOB (6) was obtained by amide-bond formation with 5-norbornene-2-carboxylic acid in the presence of polymer supported dicyclohexylcarbodiimide (DCC) beads. In the case of AZD2281-trans-cyclooctene (AZD2281-TCO;

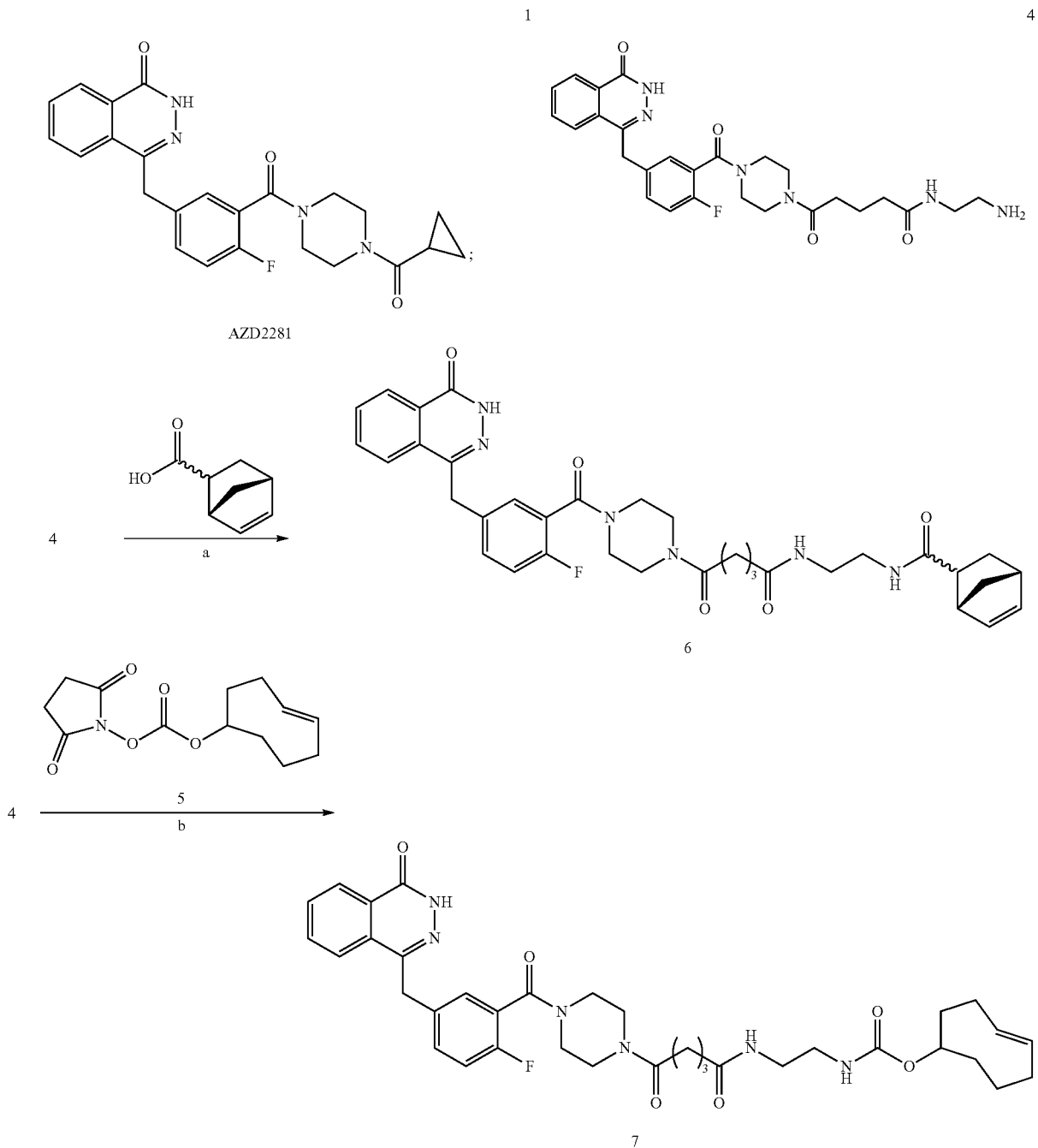

Reagents and conditions: a) Polystyrene-bound DCC, Et₃N, CH₂Cl₂, RT, overnight; b) Et₃N, CH₂Cl₂, overnight.

Briefly, for the synthesis of the bioorthogonally reactive derivatives AZD2281-NOB (6) and AZD2281-TCO (7), compound (2) was first reacted with glutaric acid anhydride to produce the glutaric acid-modified 4-(5-oxopentanamide) piperizine (3). Subsequently, an ethylene diamine spacer 7), precursor (3) was reacted with (E)-cyclooct-4-enyl 2,5-dioxopyrrolidin-1-yl carbonate (5) in the presence of triethylamine. Cycloaddition of both AZD2281-TCO (7) and Texas Red-Tz (8) was detected by mixing the two compounds (0.3 mm), agitating for several minutes, and analyzing the products by HPLC-MS.
As another example, preparation of AZD2281-$^{18}$F can be as follows:
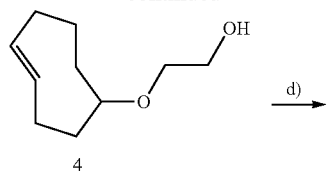
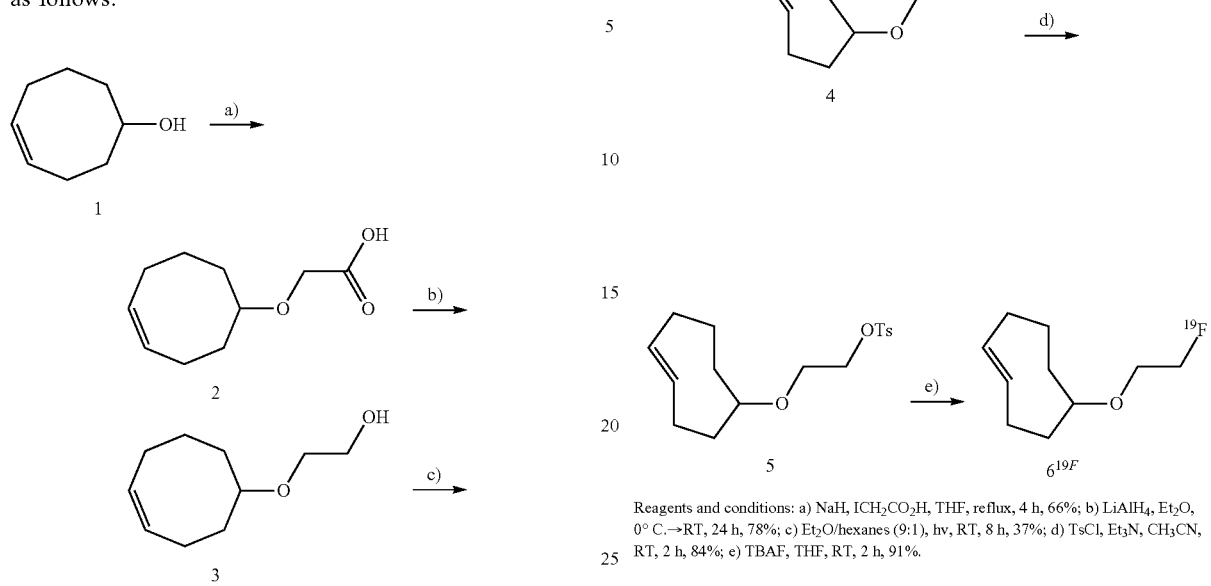
Reagents and conditions: a) NaH, ICH$_2$CO$_2$H, THF, reflux, 4 h, 66%; b) LiAlH$_4$, Et$_2$O, 0° C.→RT, 24 h, 78%; c) Et$_2$O/hexanes (9:1), hv, RT, 8 h, 37%; d) TsCl, Et$_3$N, CH$_3$CN, RT, 2 h, 84%; e) TBAF, THF, RT, 2 h, 91%.
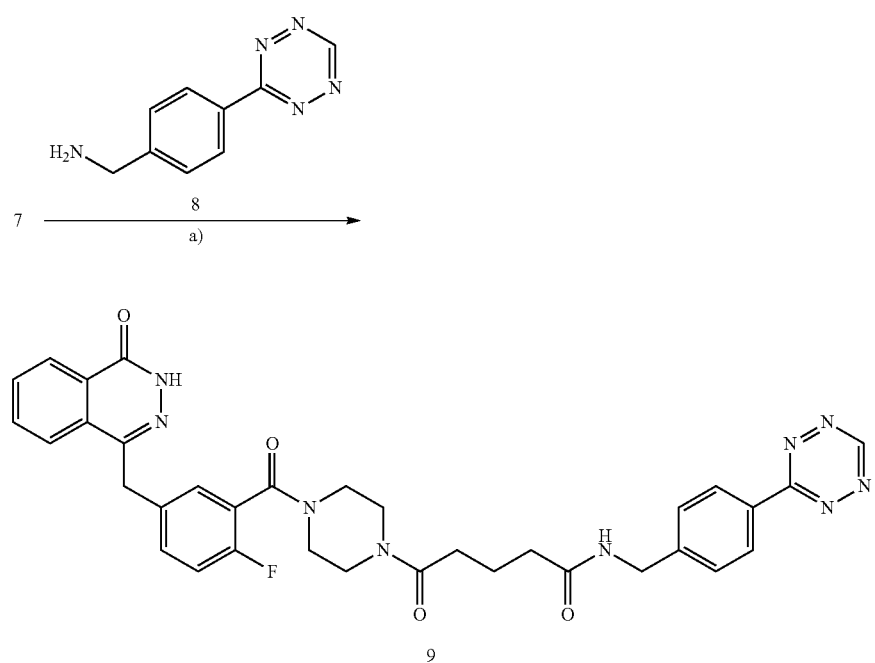
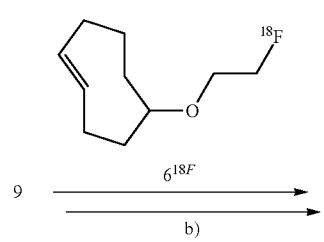

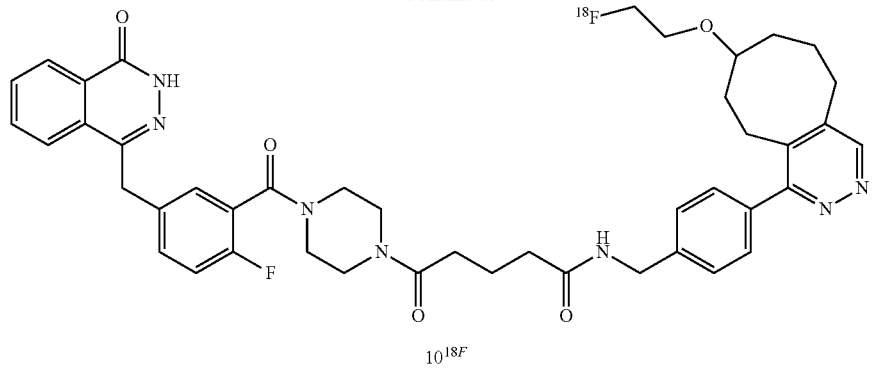

$10^{18F}$

Reagents and conditions: a) polystyrene-bound DCC, Et₃N, CH₂Cl₂, RT, 7 h, 25%; b) CH₂Cl₂, RT, 3 min, 60%.

Briefly, (Z)-2-(Cyclooct-4-enyloxy)acetic acid (2) was prepared in 63% yield over two steps from commercially available 9-oxabicyclo[6.1.0]non-4-ene. Carboxylic acid (2) was converted to (E)-2-(cyclooct-4-enyloxy)ethanol (4) first by lithium aluminum hydride (LiAlH₄) reduction to give (Z)-2-(cyclooct-4-enyloxy)ethanol (3) in 78% yield, followed by photochemical cis/trans isomerization and isolation of the (E)-isomers by the previously described cycle/trap method (M. Royzen et al., J. Am. Chem. Soc. 2008, 130, 3760-3761). The major (E)-cyclooctyl stereoisomer was isolated by column chromatography and converted to the corresponding tosylate (5) in 84% yield. (E)-5-(2-Fluoroethoxy)cyclooct-1-ene (6$^{18F}$) was prepared in 91% yield by the treatment of (5) with tetrabutylammonium fluoride (TBAF) in THF. All previously unknown compounds were fully characterized by $^1$H, $^{13}$C, and $^{18}$F NMR. As a precursor for the chemoselective reactive PARP1 inhibitor AZD2281-Tz (9), 4-[[4-fluoro-3-(4-(5-oxopentanamide) piperazine-1-carbonyl)phenyl]methyl]-2H-phthalazin-1-one (7) was generated as described herein (See Example 1). This precursor was reacted with (8) in the presence of polymer-supported N,N'-dicyclohexylcarbodiimide (DCC) beads to yield (9) as a pink solid. Cycloadduct (10$^{18F}$) was prepared by the addition of dimethyl sulfoxide (DMSO) solutions of (9) and (6$^{18F}$) at room temperature and subsequent highpressure liquid chromatography (HPLC) purification.

In some embodiments, wherein a compound of Formula (1) comprises a T moiety, preparation of the compound can include the use of bioorthogonal conjugation reactions such as the inverse electron demand Diels-Alder reaction. For example, in a compound of Formula (1) or Formula (2), T can be the reaction product of an inverse electron demand Diels-Alder reaction. This reaction employs a diene and a dienophile. The reaction of a diene (e.g., a substituted tetrazine) with a dienophile (e.g., an alkene or alkyne), produces an unstable cycloadduct that subsequently undergoes a retro-Diels-Alder cycloaddition reaction to produce dinitrogen as a byproduct and the desired dihydropyrazine (after reaction with an alkene) or pyrazine (after reaction with an alkyne) products (shown below). See e.g., Sauer et al., Chem Ber 998: 1435-1445, 1965, which is incorporated by reference in its entirety. The dihydropyrazine product may undergo an additional oxidation step to generate the corresponding pyrazine.

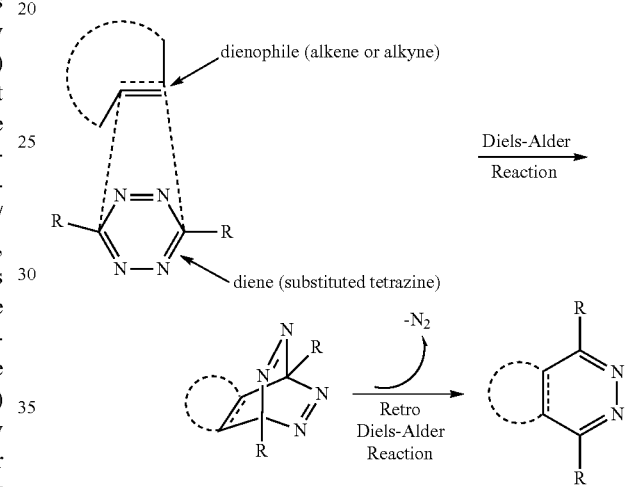

A variety of tetrazines and dienophiles including cyclic and linear alkenes or alkynes have been studied in this reaction. Selection of the appropriate reaction partners allows for tuning of the coupling rate by several orders of magnitude. (Balcar J et al., 1983, Tet Lett 24:1481-1484; Thalhammer F et al., 1990, Tet Lett 47:6851-6854). See also US 2006/0269942, WO 2007/144200, US 2008/0181847 and US 2011/0268654. Bioconjugation methods using inverse electron demand Diels-Alder cycloadditions between tetrazines and highly strained dienophiles such as norbornene and trans-cyclooctene are known in the literature, however the tetrazine used has limited stability to aqueous media. (Blackman et al., 2008, J Am Chem Soc, 130, 13518-9; Devaraj et al., 2009, Angew Chem Int Ed Engl, 48, 7013-6; Devaraj et al., 2008, Bioconjug Chem, 19, 2297-9; Pipkorn et al., 2009, J Pept Sci, 15, 235-41).

In some embodiments, the detectable agent carries a functional group such as an amine, alcohol, carboxylic acid or ester, or other group of atoms that can undergo a chemical reaction allowing attachment to the diene or dienophile. Alternatively or in addition, the dienophile or heterodienophile (which can be, e.g., an alkene, alkyne, nitroso, carbonyl or imine) possesses a reactive functional group for attachment to the detectable agent. Thus, the reactive functional group on the detectable agent and/or diene/dienophile undergoes a chemical reaction to form a link between the detectable agent and the diene or dienophile.

In some embodiments, the diene or dienophile can be incorporated into a PARP1 inhibitor and/or a detectable agent. In some embodiments, the diene or dienophile is incorporated through a linker. One of skill in the art could readily synthesize such compounds using known synthetic methods or modifying the examples provided herein.

In some embodiments, the diene can be a substituted tetrazine or other heteroaromatic ring system with at least two nitrogens adjacent to each other, and which is a highly reactive participant in the inverse electron demand Diels-Alder reaction. The diene can be linked to the amino acid or unnatural amino acid through the use of a linker. In this embodiment, the diene possesses a reactive group such as an amine, alcohol, carboxylic acid, ester, or activated ester, or other group that can undergo a chemical reaction with the reactive moiety on the PARP1 inhibitor or the detectable agent to form a link between the two. Dienes useful in the present disclosure include but are not limited to aromatic ring systems that contain two adjacent nitrogen atoms, for example, tetrazines, pyridazines, substituted or unsubstituted 1,2-diazines. Other 1,2-diazines can include 1,2-diazines annelated to a second it-electron-deficient aromatic ring such as pyrido[3,4-d]pyridazines, pyridazino[4,5-d]pyridazines, and 1,2,4-triazines. Pyridazines can also be fused with a five-membered heterocycle such as imidazo[4,5-d]pyridazines and 1,2,3-triazolo[4,5-d]pyridazines. In some embodiments, the diene is an asymmetrical tetrazine as described herein, e.g., 3-(p-Benzylamino)-1,2,4,5-tetrazine (Structure I).

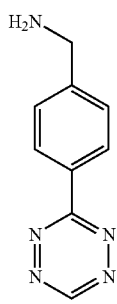

Structure I

Dienophiles useful in the present methods and compositions include but are not limited to carbon containing dienophiles such as alkenes or alkynes, or compounds containing nitroso, carbonyl or imine groups. In some embodiments, the dienophile is a strained dienophile. As used herein, a "strained" dienophile has a dihedral angle that deviates from the idealized 180 degree dihedral angle. Alternatively, non-strained dienophiles (e.g., sytrenes) and/or electron rich electrophiles (e.g., eneamines or vinyl ethers), can also be used with nitroso compounds. Alkenes as used herein refer to an alkyl group having one or more double carbon-carbon bonds such as an ethylene, propylene, and the like. Alkenes can also include cyclic, ring-strained alkenes such as trans-cyclooctene or norbornene carrying a double bond which induces significant ring strain and is thus highly reactive. Alkenes can also include more complex structures such as indoles and azaindoles, electron rich enamines. Heterodienophiles containing carbonyl, nitroso or imine groups can also be used. In some embodiments, the dienophile is a trans-cyclooctene or a trans-cyclooctenol, e.g., (E)-cyclooct-4-enol.

In some embodiments, the detectable agent is chemically attached to the dienophile. For example, the strained alkene is chemically coupled to a detectable agent, e.g., a trans-cyclooctene modified with a radioactive isotope, e.g., $^{18}F$ (see Structure II below).

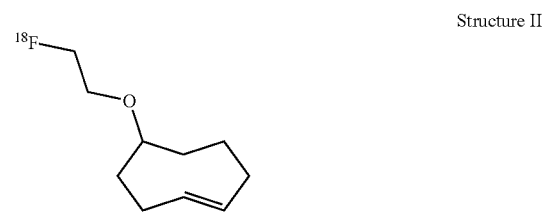 [SMILES: [18F]CCOC1CC/C=C/CCC1]

Structure II

Applicable to all other NHS esters, peptide bond formation is also possible using other standard coupling techniques (e.g. EDCI, DCI, HOBT/TBTU, and others).

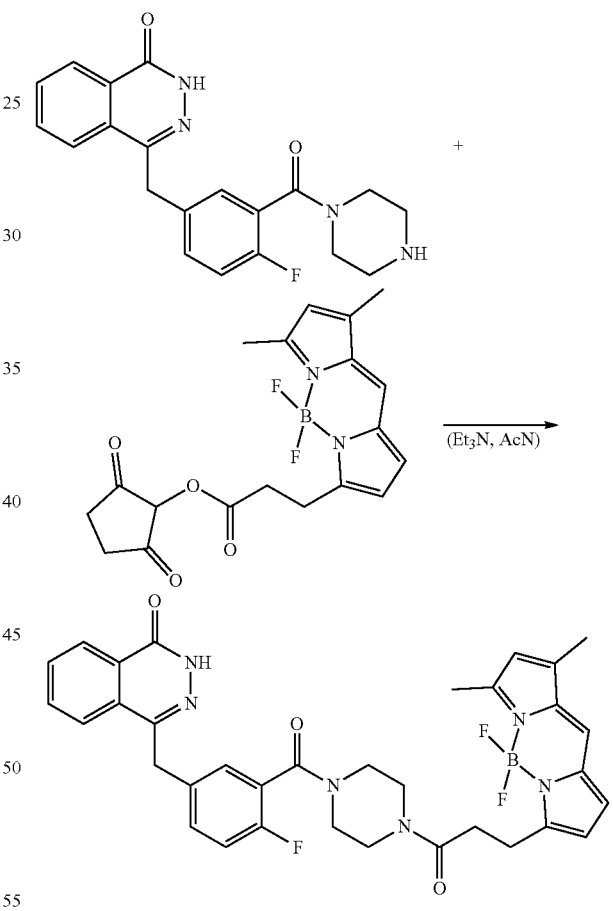

In some embodiments, AZD2281-BODIPY FL is reacted with trialkylsilyl triflates (e.g. trimethylsilyl triflate) and in some cases followed by dialkylaminopyridines (e.g. dimethylaminopyridine, DMAP). $^{18}F$-Fluoride is added and the $^{18}F$-AZD2281-BODIPY FL is being produced through the exchange of triflate or DMAP at the BODIPY boron core with $^{18}F$-fluoride. In some embodiments, trialkylsilyls triflates are immobilized on a solid support (e.g. magnetic materials, dextrans, polystyrenes, latex, biological macromolecules). In some embodiments, 4-amino pyridines are immobilized on a solid support (e.g. magnetic materials, dextrans, polystyrenes, latex, biological macromolecules). The reactive solid support is then treated with AZD2281-BODIPY FL. Incubation with $^{18}$F-fluoride is followed by filtration of the solid support, resulting in high specific activity labeled material (e.g. high specific activity PARP1 imaging agents). See, for example, FIG. 15.

One problem during the synthesis of $^{18}$F-radiolabeled compounds is that in most cases large amounts of precursors are used to efficiently react with small quantities of $^{18}$F. The resulting mixtures can be purified by HPLC to remove the excess starting material, which in most cases will compete with the radiolabeled probe for the targeted binding sites. In some embodiments, however, to avoid lengthy HPLC purifications, the resulting materials can be purified using a scavenger resin as provided herein. The resins can include those of Formula (3):

wherein:
R is a resin bead;
L is a linker; and
X is a moiety that reacts with the unreacted starting material.

The resin bead can be made of many types of materials known to those of skill in the art as long as the bead is large enough to be filtered. In some embodiments, the resin bead can be magnetic, a modified filter, a modified column material, etc. For example, the resin can be made of dextran, silica, glass, or any other non-reactive solid support. In some embodiments, the resin bead is a magnetic resin bead.
In some embodiments, X is a trans-cyclooctene. For example, a non-limiting example of a resin includes:

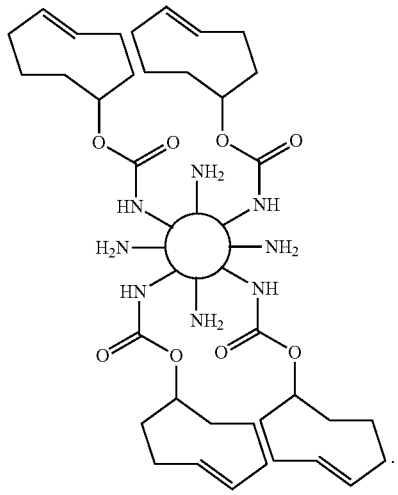

Accordingly, provided herein is a method of purifying a composition comprising an $^{18}$F-labeled compound (e.g., a compound of Formula (1). The method can include contacting a composition comprising a $^{18}$F-labeled compound and excess of non-labeled starting material with an excess of a resin of Formula (3); and separating out the product of the starting material and the resin of Formula (3). In some embodiments, the method can result in a composition comprising at least about 75% of an $^{18}$F-labeled compound (e.g., at least about 80%, at least about 85%, at least about 90%, at least about 93%, at least about 95%, at least about 96%, at least about 97%, at least about 98%, and at least about 99%). A resin of Formula (3) can be prepared, for example, by reaction of commercially available magnetic amine-decorated beads in a solution of DMF/PBS with a 75 mm solution of NHS-activated trans-cyclooctene (see FIG. 5).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1$^{st}$ Ed., Oxford University Press, 2000; *March's Advanced Organic chemistry: Reactions, Mechanisms, and Structure*, 5$^{th}$ Ed., Wiley-Interscience Publication, 2001; and Peturssion, S. et al., "*Protecting Groups in Carbohydrate Chemistry,*" *J. Chem. Educ.*, 74(11), 1297 (1997) (each of which is incorporated herein by reference in their entirety).

Reactions can be monitored according to any suitable method known in the art.

For example, product formation can be monitored by spectroscopic means, such as nuclear magnetic resonance spectroscopy (e.g., $^1$H or $^{13}$C), infrared spectroscopy, spectrophotometry (e.g., UV-visible, fluorescence), mass spectrometry, or by chromatographic methods such as high performance liquid chromatography (HPLC), liquid chromatography-mass spectroscopy (LCMS), thin layer chromatography (TLC), or radio-thin layer chromatograph (rTLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6) (2004), which is incorporated herein by reference in its entirety) and normal phase silica chromatography.

Pharmaceutical Compositions

The methods provided herein include the manufacture and use of pharmaceutical compositions, which include compounds identified by a method provided herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The pharmaceutical composition may be administered at once, or may be divided into a number of smaller doses to be administered at intervals of time. It is understood that the precise dosage and duration of administration may be determined empirically using known testing protocols or by extrapolation from in vivo or in vitro test data. It is to be noted that concentrations and dosage values may also vary with the size of the area to be imaged. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

The pharmaceutical compositions can be included in a container, pack, or dispenser together with instructions for administration.

Methods of Use

The compounds described herein can be imaged using methods known in the art. For example, imaging can be achieved in living animals, organs, or tissues, using e.g. near infrared (NIR), MR imaging (MRI), positron emission tomography (PET), single photon computerized tomography (SPECT), or other whole body imaging modalities. The detectable agent of the compound can be imaged by these whole body imaging modalities to detect cancer cells (e.g., cancer cells overexpressing PARP1). For example, a compound having a fluorescent detectable agent can be detected by traditional fluorescence imaging techniques allowing for the facile tracking of the compounds by fluorescence microscopy or flow cytometry using methods known in the art, e.g., as described in US 2005/0249668, the content of which is incorporated by reference in its entirety. In some embodiments, a compound having a radioactive agent can be imaged using positron emission tomography (PET).

The compositions and methods described herein can be imaged using a variety of modalities that are known to one of skill in the art. Detection methods can include both imaging ex vivo and in vivo imaging methods, e.g., immunohistochemistry, bioluminescence imaging (BLI), Magnetic Resonance Imaging (MRI), positron emission tomography (PET), Single-photon emission computed tomography (SPECT), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required. In some embodiments, one or more imaging techniques can be used in the methods provided herein. For example, fluorescence, PET and/or SPECT imaging can be used.

The compounds and compositions described herein can be used in in vivo imaging methods to detect, quantify and evaluate PARP1 (e.g., PARP1 in a cancer). In general, such methods include administering to a subject one or more compounds of Formula (1) or Formula (2) described herein; optionally allowing the compound to distribute within the subject; and imaging the subject, e.g., by fluoroscopy, radiography, computed tomography (CT), MRI, PET, SPECT, laparoscopy, endomicroscopy, or other whole body imaging modality to detect the presence of PARP1. Furthermore, it is understood that the methods (or portions thereof) can be repeated at intervals to evaluate the subject and detect any changes in PARP1 concentration over time. Information provided by such in vivo imaging, for example, the presence, absence, or level of emitted signal, can be used to detect and/or monitor the loss of PARP1 or increase of PARP1, e.g., after medical treatment.

A number of preclinical and clinical applications for a compound provided herein can be envisioned. For example, a compound described here can be used: 1) for the early detection cancers (e.g., cancers that overexpress PARP1 such as pancreatic cancer); 2) as an aid to surgeons during surgery (e.g., by allowing for real-time detection of cancer cells); and 3) as a method for monitoring the progress of a cancer treatment (e.g., by quantifying the amount of PARP1 present before, during, and after treatment).

In some embodiments, the methods provided herein include methods for detecting a cancer, i.e., a cancer that overexpresses PARP1. Generally, the methods include administering an effective amount of a compound (i.e., active ingredient) as provided herein (i.e., a compound of Formula (1)) to a subject who is in need of, or who has been determined to be in need of, such detection and detecting the compound. In addition, provided herein are methods for imaging a cancer cell. Generally, the methods include contacting a cell with an effective amount of a compound as provided herein and imaging the cell. Such methods may be conducted in vitro or in vivo.

The compounds according to Formula (1) can be used to detect any cancer that overexpresses PARP1, are believed effective to detect and image a broad range of cancers types, including but not limited to breast cancer, ovarian cancer, and prostate cancer. In some embodiments, the cancer is an epithelial cancer. The methods and compositions described herein can be used to help a physician or surgeon to identify and characterize cancers. The methods and compositions described herein can also be used in the detection, characterization, and/or determination of the localization of the cancer, especially early in the disease, the severity of a cancer, the staging of a cancer, and/or monitoring a cancer. The presence, absence, or level of an emitted signal can be indicative of the state of the cancer.

Cancers that may be detected and/or imaged by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, epithelial cancer, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "cancer cell", as provided herein, includes a cell afflicted by any one of the above identified disorders.

The compounds according to Formula (1) can also be administered to a subject in combination with surgical methods to treat cancers, e.g., resection of tumors. The compounds can be administered to the individual prior to, during, or after the surgery. The compounds can be administered parenterally, intravenous or injected into the tumor or surrounding area after tumor removal, e.g., to image or detect residual cancer cells. For example, the compound may be used to detect the presence of a tumor and to guide surgical resection. In some embodiments, the compound can be used to detect the presence of residual cancer cells and to guide continued surgical treatment until at least a portion (e.g., all) such cells are removed from the subject. Accordingly, there is provided a method of guided surgery to remove at least a portion of a tumor from a subject comprising providing a compound of Formula (1); causing the compound to be present in at least some cancer cells in an effective amount to inhibit PARP1 and for detection of the compound to be observable; observing the image (e.g., fluorescence, PET or SPECT scan); and performing surgery on the subject to remove at least a portion of the tumor that comprises detected cancer cells.

In some embodiments, a compound of Formula (1) or Formula (2) is imaged in vivo using PET or SPECT imaging. For example, the use of such methods permits the facile, real-time imaging and localization of cancers labeled with a compound having a radioactive detectable agent. In some embodiments, PET or SPECT can be used to diagnose cancer by imaging the accumulation of a compound provided herein in cancer cells expressing PARP1. In some embodiments, the use of PET and/or SPECT as an imaging modality can be useful during surgery to locate cancer cells (e.g., residual cancer cells following excision of a tumor mass).

In some embodiments, a compound of Formula (1) or Formula (2) is imaged in vivo using laparoscopy and endomiscroscopy. For example, the use of laparoscopy permits the facile, real-time imaging and localization of cancers labeled with a compound having a fluorescent detectable agent. In some embodiments, laparoscopy can be used to diagnose cancer by imaging the accumulation of a compound provided herein in cancer cells expressing PARP1. In some embodiments, the use of laparoscopy as an imaging modality can be useful during surgery to locate cancer cells (e.g., residual cancer cells following excision of a tumor mass). In some embodiments, a compound can be imaged using fiber optic endomicroscopy.

In addition, in vivo imaging can be used to assess the effect of an anti-cancer therapy on cells expressing PARP1, by using the compounds described herein, wherein the subject is imaged prior to, during, and/or after treatment with the therapy, and the corresponding signal/images are compared. For example, a subject with a cancer can be imaged prior to and after treatment with chemotherapy or radiation therapy to determine the response of the PARP1-expressing cancer cells to treatment.

As described herein, a compound of Formula (1) accumulates in PARP1 expressing cells (e.g., PARP1 overexpressing cancer cells). This accumulation, however, can be quantifiably inhibited by administration of an unlabeled PARP1 inhibitor, e.g., the parent PARP1 inhibitor present in the compound of Formula (1) or any other PARP inhibitor. Accordingly, further provided herein is a method for measuring PARP1 inhibition by any PARP1 inhibitor or compound that has an effect on PARP expression or activity level. Generally, the method includes contacting a cell (e.g., administering to a subject) an effective amount of a compound of Formula (1) and a therapeutic PARP1 inhibitor (i.e., non-labeled), and imaging the cell (e.g., the subject) to determine the amount of the compound of Formula (1) present.

In addition to promising approaches of PARP1 inhibitors as anti-cancer drugs, it has been shown that DNA-damage leads to rapid activation (10- to 500-fold) and recruitment of PARP1 (see, e.g., Hassa, 2008, *Front. Biosci.*, 13, 3046-3082; Jean-François Haince and Michael J. Hendzel, 2008, *J. Biol. Chem.*, 283, 1197-1208). Although not much is known about PARP1 protein levels and activities in tumor cells versus healthy cells (see Michèle Rouleau and Guy G. Poirier, 2010, *Nature Rev Cancer*, 10, 293-301), different reports show increased activity and/or expression levels of PARP1 in cancer cell lines and tumors versus healthy tissue (Zaremba T, 2009, *Br J Cancer.*, 101, 256-262; Katsuhiko Nosho, 2006, *Eur. J. Cancer*, 42, 2374-2381).

With respect to in vitro imaging methods, the compounds and compositions described herein can be used in a variety of in vitro assays. An exemplary in vitro imaging method comprises: contacting a sample, for example, a biological sample (e.g., a cell such as a cancer cell), with one or more compounds of Formula (1) or Formula (2); allowing the conjugate(s) to interact with a biological target in the sample; optionally, removing unbound agents; illuminating the sample with light of a wavelength absorbable by a fluorophore of the agents; and detecting a signal emitted from fluorophore thereby to determine whether the agent has been activated by or bound to the biological target.

After a compound has been designed, synthesized, and optionally formulated, it can be tested in vitro by one skilled in the art to assess its biological and performance characteristics. For instance, different types of cells grown in culture can be used to assess the biological and performance characteristics of the compound. Cellular uptake, binding or cellular localization of the agent can be assessed using techniques known in the art, including, for example, fluorescent microscopy, fluorescence-activated cell sorting (FACS) analysis, immunohistochemistry, immunoprecipitation, in situ hybridization and Forster resonance energy transfer (FRET) or fluorescence resonance energy transfer.

By way of example, the compound can be contacted with a sample for a period of time and then washed to remove any free compound. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the compounds. Other detection methods including, but not limited to flow cytometry, immunoassays, hybridization assays, and microarray analysis can also be used.

In some embodiments, the compounds can be used in an in vitro assay for detecting agents that inhibit PARP1.

EXAMPLES

The invention is further described in the following examples, which do not limit the scope of the invention described in the claims. Compound numbers are independent in each of the following Examples.

Example 1

A. Preparation of AZD2281-TCO (7).
Materials and Methods
Until otherwise noted, all reagents were purchased from Sigma-Aldrich (St. Louis, Mo.) and used without further purification. Texas Red-X, succinimidyl ester was purchased from Invitrogen (Carlsbad, Calif.). Cyclohexylcarbodiimide polystyrene resin was purchased from EMD biosciences (Gibbstown, N.J.). LC-ESI-MS analysis and HPLC purifications were performed on a Waters (Milford, Mass.) LC-MS system. For LC-ESI-MS analyses, a Waters XTerra® C18 5 μm column was used. For preparative runs, an Atlantis® Prep T3 OBD™ 5 μM column was used. High-resolution electrospray ionization (ESI) mass spectra were obtained on a Bruker Daltonics APEXIV 4.7 Tesla Fourier Transform mass spectrometer (FT-ICR-MS) in the Department of Chemistry Instrumentation Facility at the Massachusetts Institute of Technology. Cellular images were taken on a Nikon (Tokyo, Japan) Eclipse 80i microscope with either a Nikon Plan Apo 40X/0.95 air or a Nikon Plan Apo 60X/1.45 oil immersion objective. IC$_{50}$ assays were analyzed using a Tecan (Männedorf, Switzerland) Safire microplate system. All kinetic data were analyzed using Prism 4 (GraphPad, La Jolla, Calif.) for Mac.

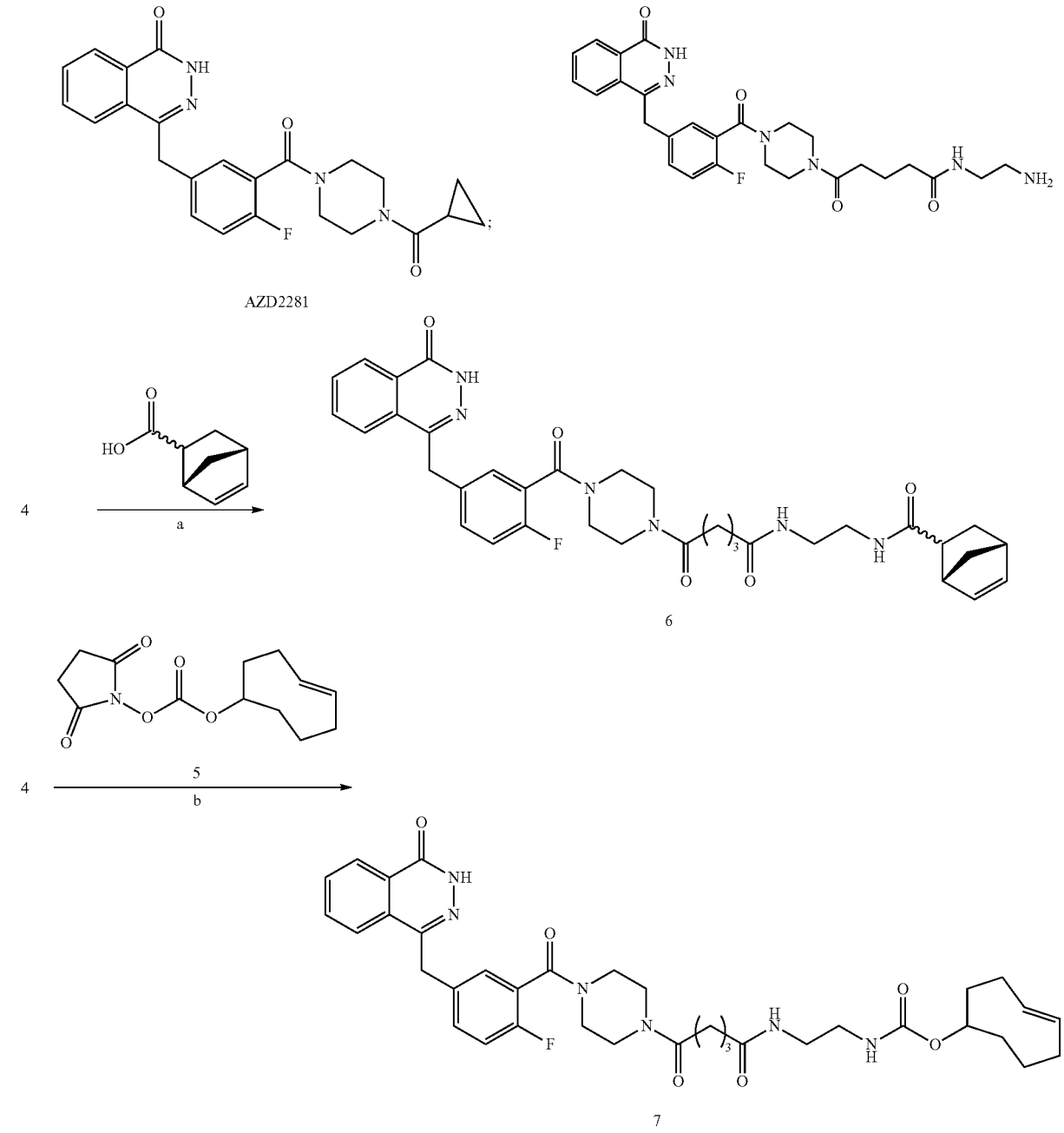

General Methods

Texas Red-Tz (8) was synthesized similar to methods described earlier. (See N. K. Devaraj et al., *Angew. Chem., Int. Ed.* 2010, 49, 2869-2872; N. K. Devaraj et al., *Angew. Chem., Int. Ed.* 2009, 48, 7013-7016, S7013/1-S7013/6; and N. K. Devaraj et al., *Bioconj. Chem.* 2008, 19, 2297-2299. (Cyclopropanecarbonyl)piperazine-1-carbonyl]-4-fluorophenyl]methyl]-2H-phthalazin-1-one (1), 4-[[4-Fluoro-3-(piperazine-1-carbonyl)phenyl]methyl]-2H-phthalazin-1-one (2) and (E)-cyclooct-4-enyl 2,5-dioxopyrrolidin-1-yl carbonate (5) were synthesized as described earlier. (See K. A. Menear et al., *J. Med. Chem.* 2008, 51, 6581-6591; and N. K. Devaraj et al., *Angew. Chem., Int. Ed.* 2009, 48, 7013-7016, S7013/1-S7013/6).

Preparation of 4-[[4-Fluoro-3-(4-(5-oxopentanamide)piperazine-1-carbonyl)phenyl]methyl]-2H-phthalazin-1-one (3)

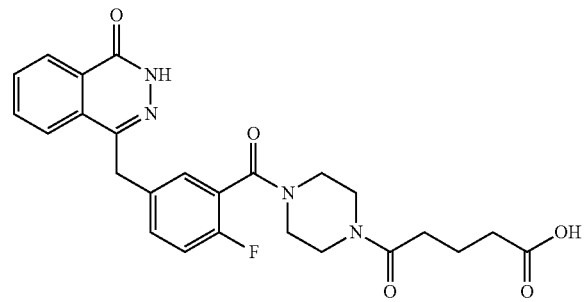

3

Glutaric anhydride (0.50 g, 4.37 mmol) and N,N-diisopropylethylamine (2.28 mL, 13.11 mmol) were added to a solution of 4-[[4-Fluoro-3-(piperazine-1-carbonyl)phenyl]methyl]-2H-phthalazin-1-one (2) (1.60 g, 4.37 mmol) in dichloromethane (50 mL) and the reaction mixture and stirred for 30 minutes. Water (50 mL) was then added and the reaction mixture stirred for another 30 minutes. The reaction mixture was acidified with HCl to pH 2, the organic phase separated and the aqueous phase extracted with dichloromethane (3×30 mL). The combined organic phases were dried over MgSO₄ and volatiles removed in vacuo. The resulting crude material was purified using silica chromatography (0%-30% MeOH/DCM), yielding the pure product as an off-white solid (1.52 g, 3.16 mmol, 72%).

Preparation of 4-[[4-Fluoro-3-(4-(N-(2-aminoethyl)-5-oxo-pentanamide)piperazine-1-carbonyl)phenyl]methyl]-2H-phthalazin-1-one (4)

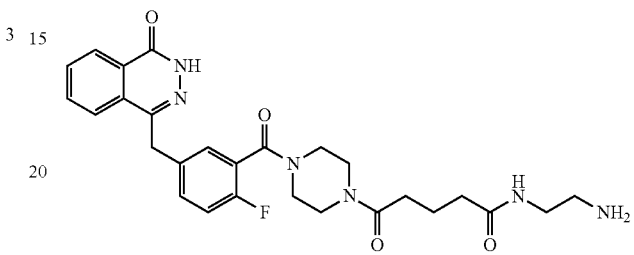

4

Cyclohexylcarbodiimide polystyrene resin (634 mg, 2.3 mmol/g) was added to a solution of 4-[[4-Fluoro-3-(4-(5-oxopentanamide)piperazine-1-carbonyl)phenyl]methyl]-2H-phthalazin-1-one (3) (350 mg, 0.73 mmol) in dichloromethane (20 mL) and the resulting mixture stirred gently for 7 hours at room temperature. Subsequently, ethylenediamine (976 μL, 14.6 mmol) was added and the reaction mixture stirred for another 60 minutes, before the reaction mixture was filtered and volatiles removed in vacuo. The crude material was purified via HPLC, yielding the title compound as a clear solid (62 mg, 0.12 mmol, 16%).

Preparation of AZD2281-NOB (6)

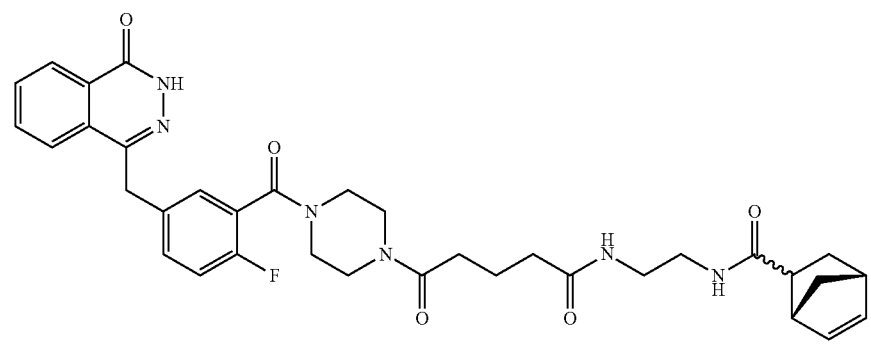

6

Cyclohexylcarbodiimide polystyrene resin (33 mg, 2.3 mmol/g) and triethylamine (16 μL, 0.11 mmol) were added to a solution of 4-[[4-Fluoro-3-(4-(N-(2-aminoethyl)-5-oxo-pentanamide)piperazine-1-carbonyl)phenyl] methyl]-2H-phthalazin-1-one (4) (20 mg, 38 μmol) and 5-norbornene-2-carboxylic acid (11 mg, 77 μmol) in dichloromethane (1 mL) and the resulting mixture stirred gently over night at room temperature. Subsequently, the reaction mixture was filtered and volatiles removed in vacuo. The crude material was purified via HPLC, yielding the title compound as a clear solid (5.9 mg, 9 μmol, 24%).

Preparation of AZD2281-TCO (7)

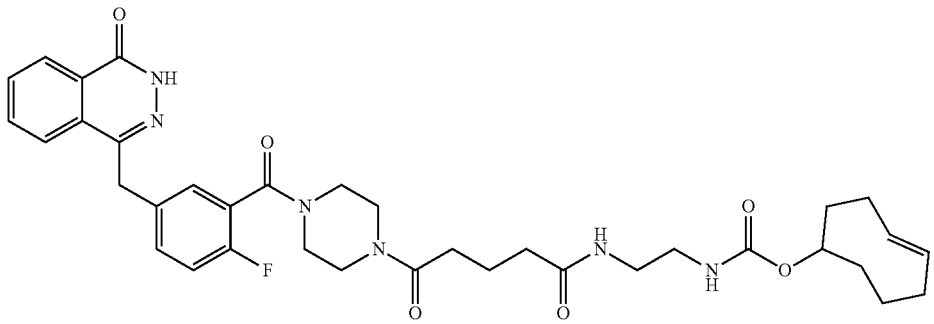

Triethylamine (16 μL, 0.11 mmol) was added to a solution of 4-[[4-Fluoro-3-(4-(N-(2-aminoethyl)-5-oxo-pentana-mide)piperazine-1-carbonyl)phenyl] methyl]-2Hphthalazin-1-one (4) (20 mg, 38 μmol) and (E)-cyclooct-4-enyl-2,5-dioxopyrrolidin-1-yl carbonate (5) (12 mg, 46 μmol) in dichloromethane (1 mL) and the resulting mixture stirred gently over night at room temperature. Subsequently, the reaction mixture was filtered and volatiles removed in vacuo. The crude material was purified via HPLC, yielding the title compound as a clear solid (11.3 mg, 17 μmol, 44%).

B. HPLC Characterization of Reaction Between Texas-Red-Tetrazine (8) and AZD2281-TCO (7)

Figure 1B:
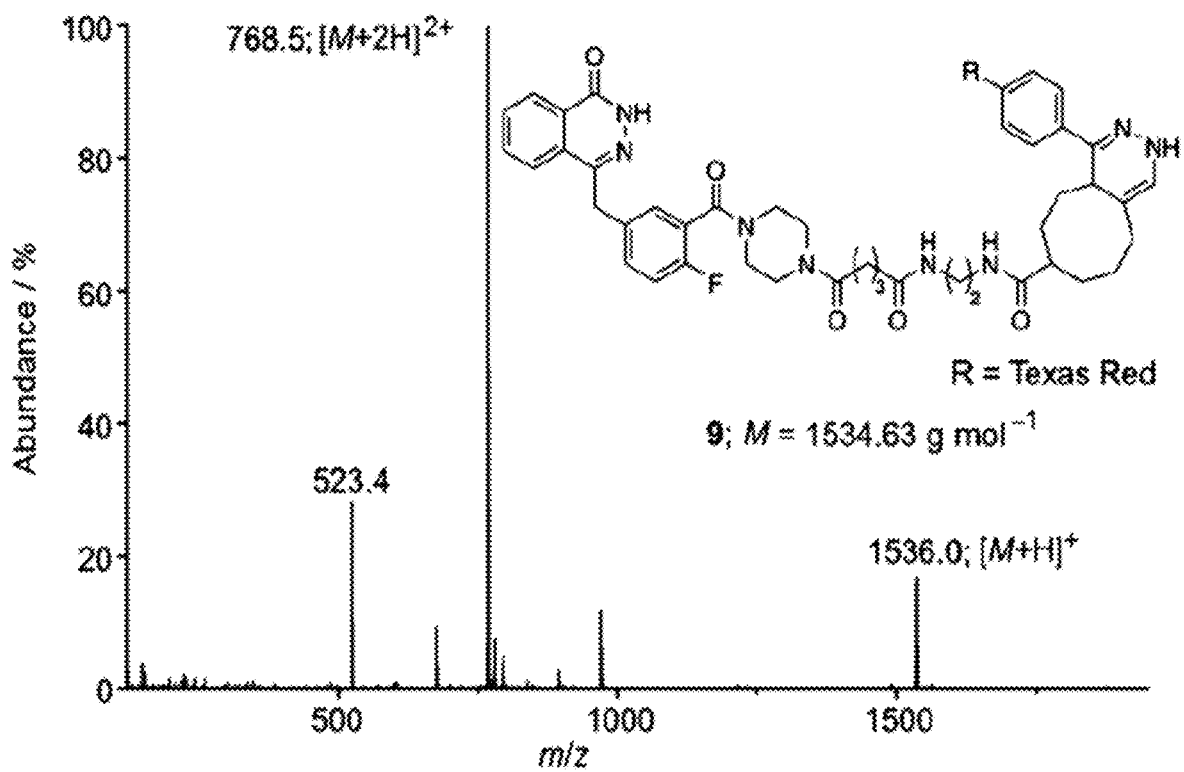
FIG. 1B shows an LC-MS spectrum of AD2281-Texas Red (9; LC-MS of major product peak shown).

(9). See FIG. 1. FIG. 1A shows the HPLC trace for the AZD2281-Texas Red (9) crude reaction mixture. LC-MS spectra confirmed the quantitative conversion of Texas Red-Tz (8). Multiple peaks were identified with a molecular mass corresponding to AZD2281-Texas Red (9; FIG. 1 B, m/z 1536.0 [M+H]+). These were the result of different isomers formed in the tetrazine trans-cyclooctene cycloaddition. The fast and selective conversion of AZD2281-TCO (7) to AZD2281-Texas Red (9) in the presence of Texas Red-Tz (8) indicates that these small molecules also have potential applicability to in vivo experiments.

C. PARP-1 $IC_{50}$ Determination

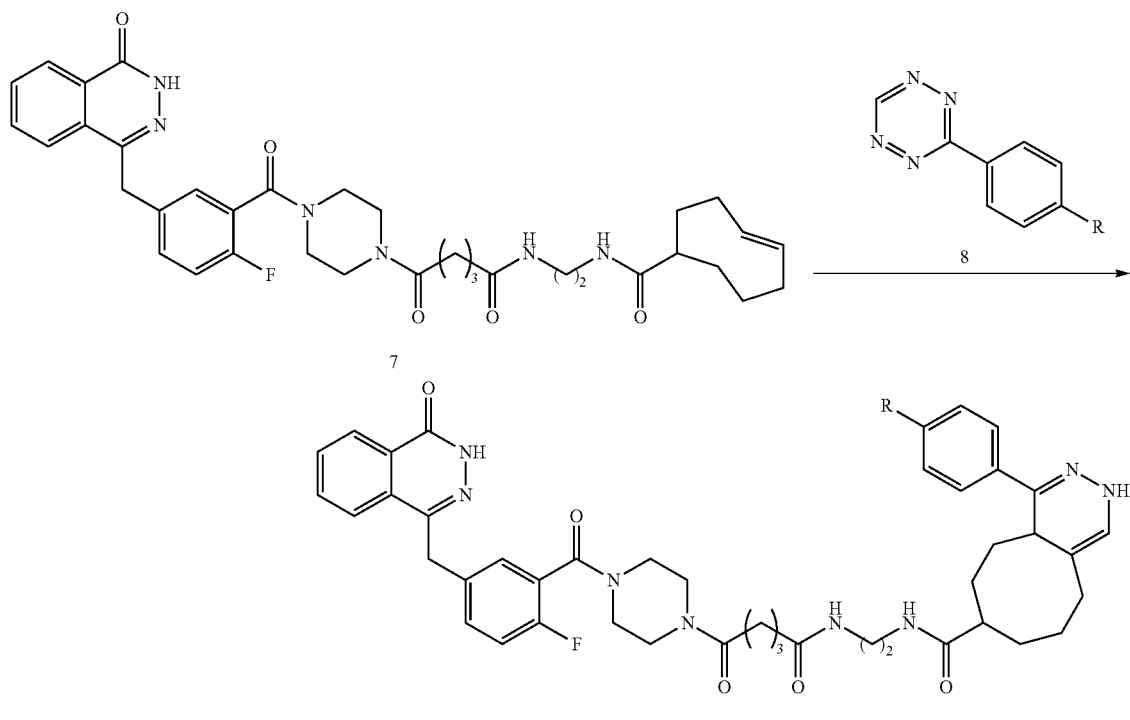

R = Texas Red

AZD2281-TCO (7) and Texas Red-tetrazine (8) were combined in 40 μL of DMSO/PBS at a final concentration of 0.3 mM for each reagent. The solution was stirred for several minutes at room temperature, yielding AZD2281-Texas Red The inhibitory potentials of AZD2281 derivatives 6 and 7, and of pre-reacted AZD2281-Texas Red (9), were tested using a PARP1 activity assay. A commercially available colorimetric assay (Trevigen, Gaithersburg, Md.) was used to measure PARP activity in vitro in the presence of inhibitors. Ten-fold dilutions of AZD2281-derivatives (6) (final concentration 400 nM to 0.04 nM); and (7), (9) (4 μM to 0.04 nM) were incubated with 0.5 units PARP HSA for 10 minutes in histone-coated 96-well plates. All experiments were carried out in triplicate. Control samples did not contain inhibitor and background measurement samples did not contain PARP-1. All reaction mixtures were adjusted to a final volume of 50 μL and a maximum final concentration 0.4% DMSO in assay buffer. The remainder of the assay was performed according to the manufacturer's instructions. PARP activity was measured by absorbance at 450 nm in each well using a Safire 2 microplate reader (Tecan Group, Männedorf, Switzerland). $IC_{50}$ values were calculated using Prism software (GraphPad, La Jolla, Calif.).

Analysis of the AZD2281 derivatives 6 and 7 resulted in $IC_{50}$ values of 10.1±1.3 nM and 11.8±1.4 nM, respectively. Thus, modification and conjugation of linkers and fluorophores to the 4-NH-piperazine group of AZD2281 precursor 2 appear to be tolerated by the enzyme, and allow the design of bifunctional derivatives. The $IC_{50}$ value of pre-reacted AZD2281-Texas Red (9; 15.4±1.2 nM) demonstrates that the trans-cyclooctene/tetrazine cycloaddition only minimally reduces binding of the 1(2H)-phthalazinone to PARP1, which confirms its possible application as an imaging probe.

D. In Vitro Cell Assays

Due to their fast reaction kinetics compared to AZD2281-NOB (6), the trans-cyclooctene conjugated AZD2281 (AZD2281-TCO; 7) and Texas Red-Tz (8) were tested under in vivo conditions in live cells.

Cell Culture

MDA-MB-231 and MDA-MB-436 cells were obtained from the ATCC and cultured in RPMI 1640 supplemented with 10% fetal bovine serum, L-glutamine, and penicillin/streptomycin. MDA-MB-231 and MDA-MD-436 cells stably expressing PARP-GFP were derived by transfection with Lipofectamine 2000 (Invitrogen) and isolation of individual G418-resistant clones. Cells were maintained in growth medium containing 1 mg/mL G418. Expression of PARP-GFP in MDA-MB-436 cells was verified using immunofluorescence microscopy to show nuclear localization of PARP-GFP, and western blotting for PARP-GFP.

For AZD2281-TCO $IC_{50}$ assays, MDA-MB-436 cells (500 μL, 80.000 cells/mL) were seeded into glycerine-treated 8-well chamber slides (Lab Tek™, Thermo Scientific, Rochester, N.Y.), and allowed to attach overnight. Cells were then incubated with Texas Red-Tz (8) (25 μL, 20 μM) for 20 minutes (37° C.) before the medium was removed and cells were washed (1×, medium, 500 μL). Subsequently, 500 μL medium, Hoechst 33258 (10 μL, 100× in PBS) and AZD2281-TCO (7) (25 μL, in PBS, 3% DMSO, 30 μM-100 nM) were added and incubated at 37° C. for 20 minutes. Cells were washed with PBS (3×500 μL), fixed with paraformaldehyde (4% in PBS) and washed with PBS (3×500 μL, time between each wash=5 minutes). PBS was removed and cells mounted using Prolong Gold (Invitrogen, Carlsbad, Calif.) before imaging.

For AZD2281-TCO blocking experiments, MDA-MB-436 cells (500 μL, 80.000 cells/mL) were seeded into glycerine-treated 8-well chamber slides (Lab Tek™, Thermo Scientific, Rochester, N.Y.), and allowed to attach overnight. Cells were then incubated with Texas Red-Tz (8) (25 μL, 20 μM) for 20 minutes (37° C.) before the medium was removed and cells were washed (1×, medium, 500 μL). Subsequently, 500 μL medium, Hoechst 33258 (10 μL, 100× in PBS), AZD2281 (1) (5 μL in DMSO, 10 mM) and AZD2281-TCO (7) (25 μL, in PBS, 3% DMSO, 30 μM-100 nM) were added and incubated at 37° C. for 20 min. Cells were washed with PBS (3×500 μL), fixed with paraformaldehyde (4% in PBS) and washed with PBS (3×500 μL, time between each wash=5 min). PBS was removed and cells mounted using Prolong Gold (Invitrogen, Carlsbad, Calif.) before imaging.

Image Analysis

Cells were observed on a Nikon 80i (Nikon, Tokyo JP) microscope equipped with an ImagEM camera (Hammamatsu Photonics, Tokyo JP). Images detailing distinct and separate cellular regions were obtained with the following filters: (Dapi, excitation 350±50 nm, emission 460±50 nm, dichroic 400LP; IgG Pab, excitation 480±20 nm, emission 535±25 nm, dichroic 505LP; Texas Red-Tz (8), excitation 560±20 nm, emission 630±30 nm, dichroic 595DCLP; Chroma Technology, Bellows Falls, Vt.). Images in each channel were captured using identical acquisition parameters. For each image, both cell structures and nuclei structures have been obtained using the appropriate fluorescence filters and appropriate excitation signal levels to avoid collecting auto-fluorescence. The collected data was then pre-processed with Cellprofiler (A. E. Carpenter, et al., *Genome Biology* 2006, 7, R100) and statistics collected using Matlab (The Mathworks, Waltham, Mass.). Cell structures were then identified using Otsu's method (N. Malpica, et al., *Cytometry* 1997, 28, 289-297; and N. Otsu, *IEEE Trans. Sys. Man. Cyber.* 1979, 9, 62-66) and binary masks were generated matching the boundary of each cell structure. Within each image and for each cell, the fluorescence signal for the total cell and the signal in the nuclear area was calculated using the corresponding mask as a spatial filter. The two signals were then normalized for their total areas. The ratio of the fluorescent signal in the cytosol region over the signal in the nuclear region was then calculated. Background subtraction was performed on the normalized signal using the cell's negative masks. For all cells we chose an optimal ratio between 0.35 and 0.48 for the cytosol area over the nucleus area.

MDA-MB436 Cellular Imaging

MDA-MB-436 cells (500 μL, 80.000 cells/mL) were seeded into glycerine-treated 8-well chamber slides (Lab Tek™, Thermo Scientific, Rochester, N.Y.), and allowed to attach overnight. They were incubated with Texas Red-Tz (8) (25 μL, 20 μM) for 20 minutes (37° C.) before the medium was removed and cells were washed (1×, medium, 500 μL). Subsequently, 500 μL medium and AZD2281-TCO (7) (25 μL, in PBS, 3% DMSO, 30 μM) were added and incubated at 37° C. for 20 min. Cells were washed with PBS (3×500 μL), fixed with paraformaldehyde (4% in PBS) and washed with PBS (3×500 μL, time between each wash=5 min). Cells were permeabilized using Triton-X-100 (2% in PBS, 10 min) and incubated with anti-PARP-1 Mab (EMD biosciences, Gibbstown, N.J.) for 3 hours, before stained with secondary IgG-GFP Pab (EMD biosciences, Gibbstown, N.J.). PBS was removed and cells mounted using Prolong Gold (Invitrogen, Carlsbad, Calif.) before imaging.

Results

Figure 2A:
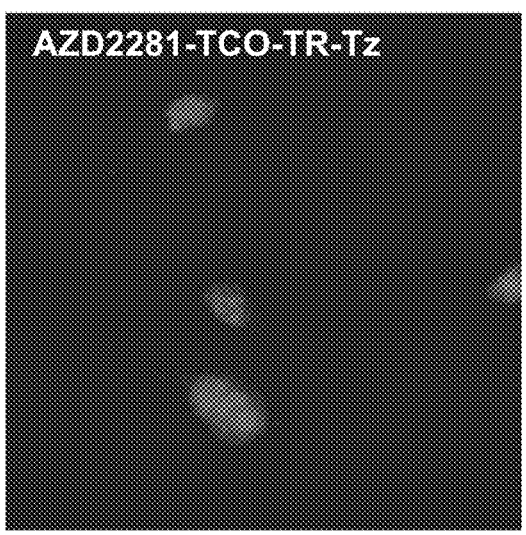
FIG. 2A illustrates the reaction of AZD2281-TCO (7) and Texas Red-Tz (8) in MDA-MB436 cells.
Figure 2B:
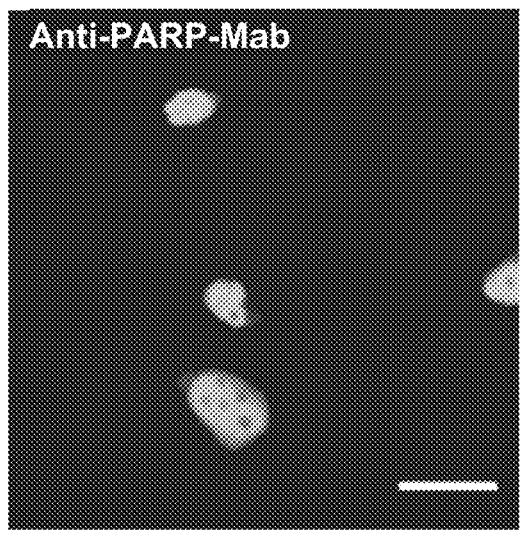
FIG. 2B shows anti-PARP1 monoclonal antibody staining.
Figure 2C:
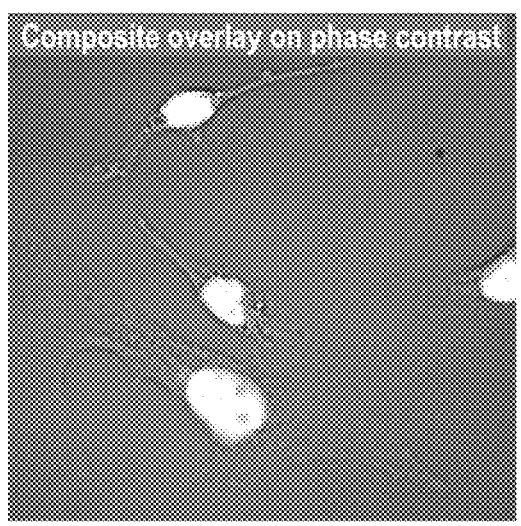
FIG. 2C is a composite overlay on phase contrast.
Figure 2D:
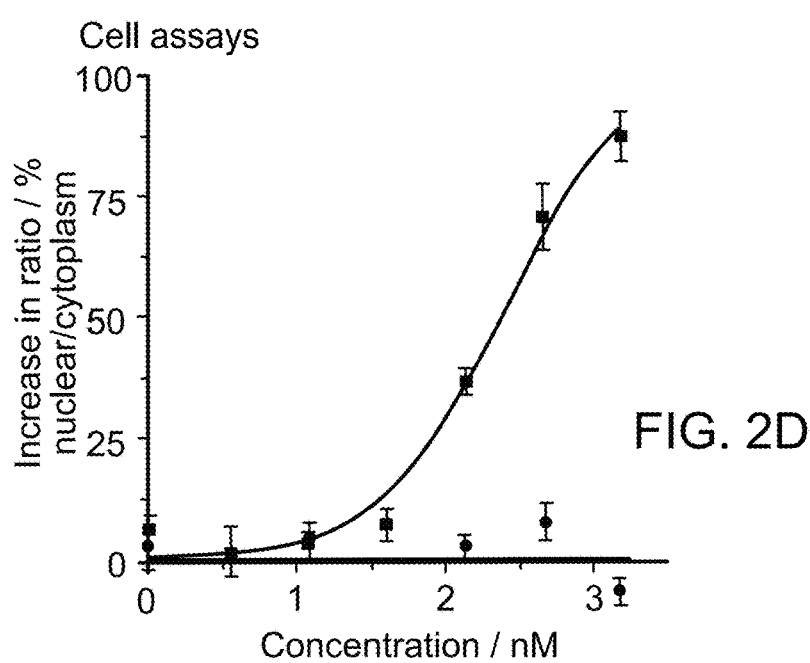
FIG. 2D illustrates the ratio of nuclear/cytoplasmic signal for AZD2281-TCO/Texas Red-Tz in the absence (not blocked: circle) and presence (blocked: square) of blocking reagent AZD2281. Scale Bar: 20 mm.

Staining patterns for the Texas Red dye (FIG. 2A) showed that it not only localized in the nucleus, but also accumulated in the nucleolus. Whilst anti-PARP1 Mabs showed similar nuclear localization (FIG. 2B), there was an absence of Mab signal in the nucleoli. This was presumably due to steric hindrance and not to the absence of PARP in the nucleolus, as earlier reports have indicated (V. S. Meder et al., *J. Cell Sci.* 2005, 118, 211-222; and J.-F. Haince et al., *J. Biol. Chem.* 2008, 283, 1197-1208). The results in FIG. 2C confirm that there was excellent spatial correlation between the small molecules (AZD2281-TCO (7)/Texas Red-Tz (8)).

E. PARP1-GFP Reporter Construct

A PARP1-GFP fusion protein was also constructed and expressed in MDA-MB436 cells as an independent confirmation of probe localization. PARP-GFP was constructed by PCR of human PARP-1 from Open Biosystems clone 5193735 from the NIH_MGC_114 cDNA library, and cloning into pAcGFP-N1 between XhoI and XmaI restriction sites. The PARP-GFP construct was verified by DNA sequencing.

PARP-1-GFP MDA-MB436 Cellular Imaging

PARP-1-GFP expressing MDA-MB-436 cells (500 μL, 80.000 cells/mL) were seeded into glycerine-treated 8-well chamber slides (Lab Tek™, Thermo Scientific, Rochester, N.Y.), and allowed to attach overnight. They were washed with PBS (3×500 μL), fixed with paraformaldehyde (4% in PBS) and washed with PBS (3×500 μL, time between each wash=5 min). Cells were permeabilized using Triton-X-100 (0.5% in PBS, 10 min) and incubated with anti-PARP-1 Mab (EMD biosciences, Gibbstown, N.J.) for 3 h, before stained with secondary IgG-GFP Pab (EMD biosciences, Gibbstown, N.J.). PBS was removed and cells mounted using Prolong Gold (Invitrogen, Carlsbad, Calif.) before imaging.

Figure 3:
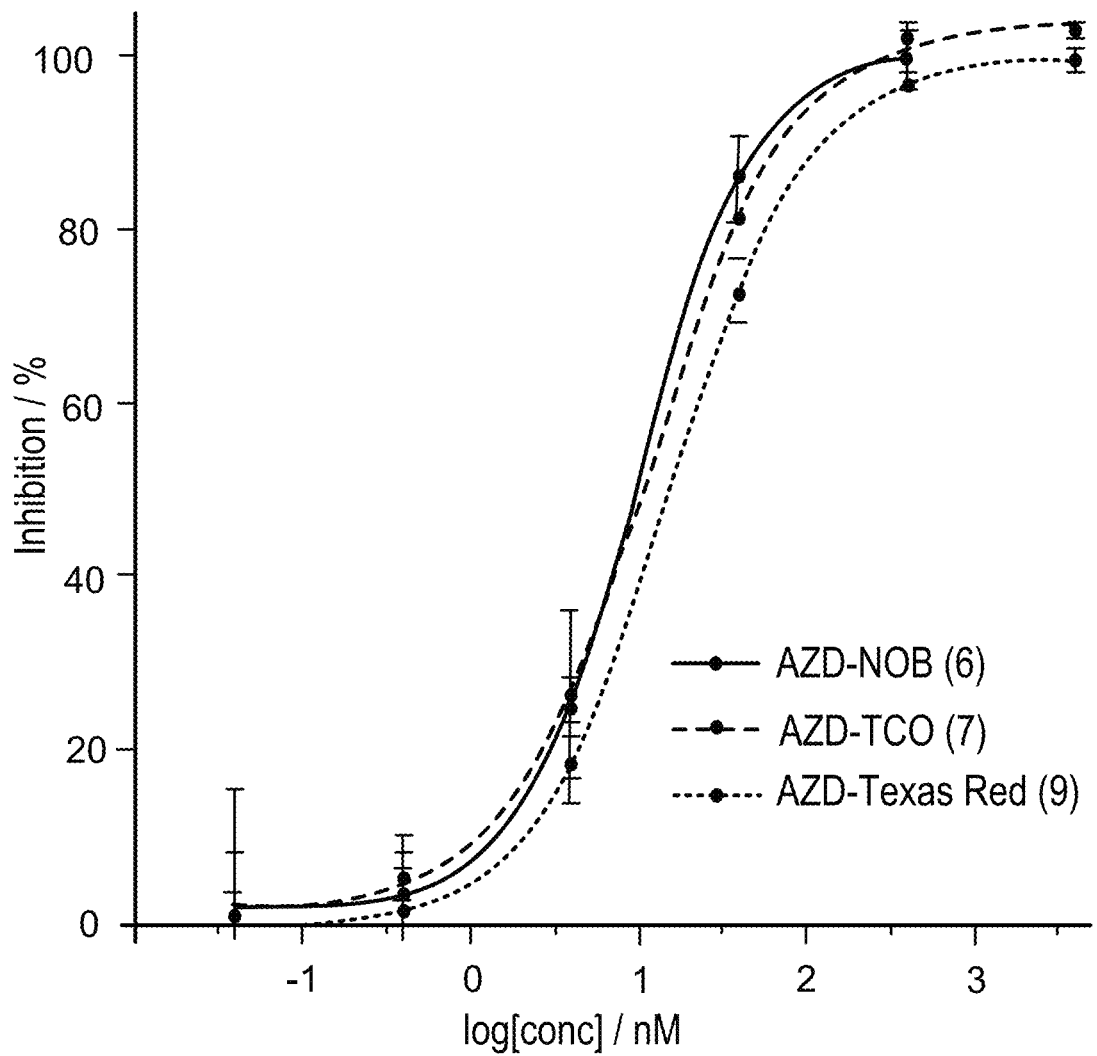
FIG. 3 shows $IC_{50}$ curves for the bifunctional 1(2H)-phthalazinone-based targeted probes.

In the PARP1-GFP expressing cells, GFP expression was clearly observed, primarily in the nucleoli but also in the nucleus. This pattern was identical to that seen with the AZD2281-TCO/Texas Red-Tz pair. (Table 1, FIG. 3). Interestingly, incubation of live cells with Texas Red-Tz (8) without AZD2281-TCO (7) did not lead to nuclear localization of the dye. Instead, there was non-lower nuclear/cytoplasmic localization ratios (modest increase of 38±2%). The superior results of sequential treatment of MDAMB436 cells with AZD2281-TCO (7) and Texas Red-Tz (8) demonstrates the advantages of a bioorthogonal in vivo reaction, since both partners (the targeting molecule 7 as well as the fluorophore 8) are small in size (7: 674.76 gmol$^{-1}$; 8: 889.05 gmol$^{-1}$), and this contributes to easier permeation. Once assembled, however, penetration is less efficient leading to trapping of the conjugate and high target-to-background ratios.

TABLE 1

IC$_{50}$ values for the bifunctional 1(2H)-phthalazinone-based targeted probes and for AZD2281-Texas Red.

| Compound | Name | # | MW [g mol$^{-1}$] | IC$_{50}$ [nM] | Reactive with |
|---|---|---|---|---|---|
| Reactive | AZD2281-NOB | 6 | 642.7 | 10.1 ± 1.3 | Tz-fluorochromes |
| inhibitor | AZD2281-TCO | 7 | 674.8 | 11.8 ± 1.4 | Tz-fluorochromes |
| Fluorescent inhibitor | AZD2281-Texas Red | 9 | 1535.6 | 15.4 ± 1.2 | NA |

Example 2

A. Synthesis

Materials and Methods.

Unless otherwise noted, all reagents were purchased from Sigma-Aldrich (St. Louis, Mo.) and used without further purification. Cyclohexylcarbodiimide polystyrene resin was purchased from EMD biosciences (Gibbstown, N.J.). 4-[[4-Fluoro-3-(4-(5-oxopentanamide)piperazine-1-carbonyl) phenyl]methyl]-2H-phthalazin-1-one (7), tetrazine amine (8), and 4-[[4-fluoro-3-(piperazine-1-carbonyl)phenyl] methyl]-2H-phthalazin-1-one (11) were synthesized as described earlier (T. Reiner et al., *Chem Bio Chem* 2010; N. K. Devaraj et al., *Bioconjug. Chem.* 2008, 19, 2297-2299; and K. A. Menear et al., *J. Med. Chem.* 2008, 51, 6581-6591. $^{18}$F-Fluoride (n.c.a.) in $^{18}$O-enriched water was purchased from PETNET (Woburn, Mass.). Automated synthesis of $^{18}$F-labeled trans-cyclooctene was carried out using a Synthra RN Plus automated synthesizer (Synthra GmbH, Hamburg, Germany) operated by SynthraView software. For nonradioactive compounds, LC-ESI-MS analysis and HPLC-purifications were performed on a Waters (Milford, Mass.) LC-MS system. For LC-ESI-MS analyses, a Waters XTerra® C18 5 μm column was used. Preparative high performance liquid chromatography (HPLC) runs for synthetic intermediates utilized an Atlantis® Prep T3 OBD™ 5 μM column (eluents 0.1% TFA (v/v) in water and MeCN; gradient: 0-1.5 min, 5-100% B; 1.5-2.0 min 100% B). For radiolabeled compounds, preparative scale HPLC purification was achieved using a Machery-Nagel Nucleodur C18 Pyramid 250×10 mm Vario-Prep column (60:40 0.1% trifluoroacetic acid (v/v) in water-acetonitrile (MeCN) at 5.5 mL·min$^{-1}$) with a 254 nm UV detector and radiodetector connected in series. Analytical HPLC of radiolabeled compounds was performed employing a Grace VYDAC (218TP510) C18 reversed-phase column (eluents 0.1% TFA (v/v) in water and MeCN; gradient: 0-17 min, 5-60% B; 17-21 min, 60-95% B; 21-24 min, 95% B; 24-25 min, 95-5% B; 25-30 min, 5% B; 2 mL·min$^{-1}$) with a dual-wavelength UV-vis detector and a flow-through gamma detector connected in series. HyperSep C18 cartridges were purchased from Thermo Electron (Bellefonte, Pa.) and Sep-pak VAC Alumina-N cartridges from Waters (Milford, Mass.). High-resolution electrospray ionization (ESI) mass spectra were obtained on a Bruker Daltonics APEXIV 4.7 Tesla Fourier Transform mass spectrometer (FT-ICR-MS) in the Department of Chemistry Instrumentation Facility at the Massachusetts Institute of Technology. IC$_{50}$ assays were analyzed using a Tecan (Männedorf, Switzerland) Safire2 microplate system. All kinetic data were analyzed using Prism 4 (GraphPad, La Jolla, Calif.) for Mac.

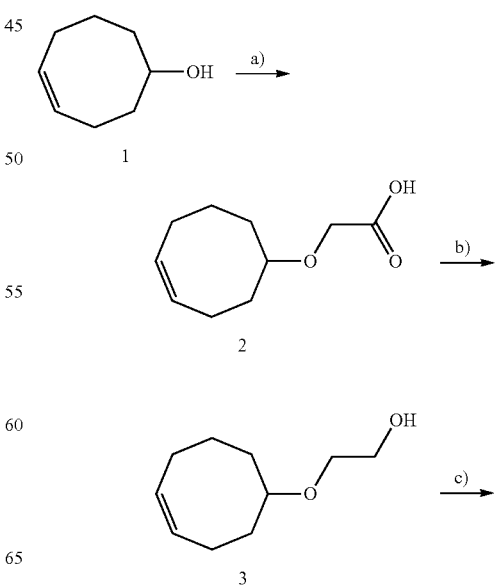

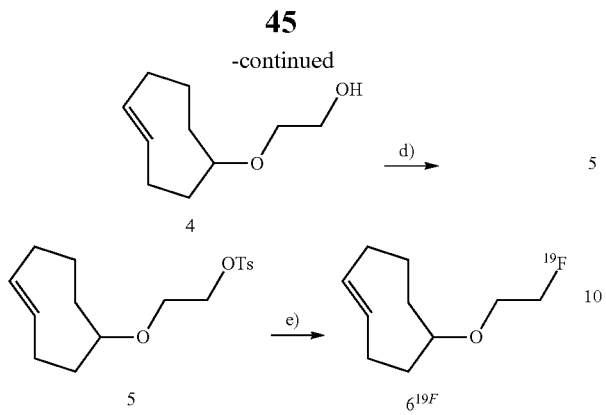

Synthetic scheme for the synthesis of radiolabeled $^{18}$F-TCO ($6^{18F}$). Reagents and conditions: a) NaH, ICH2CO2H, THF, reflux, 4 h, 66%; b) LiAlH$_4$, Et$_2$O, 0° C.→RT, 24 h, 78%; c) Et$_2$O/hexanes (9:1), hv, RT, 8 h, 37%; d) TsCl, Et$_3$N, CH$_3$CN, RT, 2 h, 84%; e) TBAF, THF, RT, 2 h, 91%.

Preparation of (Z)-Cyclooct-4-enol (1)

9-Oxabicyclo[6.1.0]non-4-ene (4.2 g, 33.8 mmol) was added slowly to LiAlH$_4$ (1.2 g, 30.4 mmol) suspended in diethyl ether (100 mL). After stirring at room temperature for 4 hours, the reaction was worked up by the sequential addition of 4 mL H$_2$O, 4 mL 25% NaOH(aq), and 4 mL of H$_2$O. The resulting mixture was filtered and the filtrate dried (Na$_2$SO$_4$) and filtered again. The clear ether solution was concentrated to give 4.1 g of (Z)-cyclooct-4-enol in 96.1% yield.

Preparation of (Z)-2-(Cyclooct-4-enyloxy)acetic acid (2)

(Z)-Cyclooct-4-enol (2.0 g, 15.8 mmol) was added slowly to a suspension of sodium hydride (1.3 g of 60% dispersion in mineral oil, 31.7 mmol) in 50 mL THF. This was stirred at reflux for 1 hour, then a solution of iodoacetic acid (2.9 g, 15.8 mmol) in 10 mL THF was added and reflux was continued for 4 hours, then the reaction was cooled to room temperature and concentrated under reduced pressure. The residue was dissolved in 10% NaOH(aq) (50 mL) and extracted with Et$_2$O (2×25 mL). The pH of the aqueous solution was lowered to (4) by the addition of 6N HCl and extracted again with DCM (2×25 mL). Separately, the organic solutions were dried (MgSO$_4$), filtered, and concentrated by rotary evaporator. The ether extraction resulted in 1.0 g of starting (Z)-cyclooct-4-enol and the DCM extraction resulted in 1.9 g of (Z)-2-cyclooct-4-enyloxy)acetic acid (2) (65.5% yield).

Preparation of (Z)-2-(Cyclooct-4-enyloxy)ethanol (3)

(Z)-2-Cyclooct-4-enyloxy)acetic acid (1.9 g, 10.3 mmol) was added to a suspension of LiAlH$_4$ (0.4 g, 9.5 mmol) in Et$_2$O (10 mL) at 0° C., warmed to room temperature, and was stirred for 24 hours. Unreacted LiAlH$_4$ was quenched with 10% HCl(aq) and the reaction diluted with 30 mL H$_2$O. The Et$_2$O layer was separated and the aqueous solution was extracted with Et$_2$O (2×10 mL). The combined Et$_2$O solutions were dried (MgSO$_4$), filtered, and concentrated. The crude mixture was subjected to column chromatography (2:3 hexanes:ethyl acetate) to give 1.4 g of (Z)-2-(cyclooct-4-enyloxy)ethanol (3) (Rf=0.58), a 78.3% yield.

Preparation of (E)-2-(Cyclooct-4-enyloxy)ethanol (4)

(Z)-2-(Cyclooct-4-enyloxy)ethanol (1.0 g, 5.9 mmol) was converted to the (E)-isomers following a previously described cycle/trap method (M. Royzen et al., J. Am. Chem. Soc. 2008, 130, 3760-3761) with the exception of using methyl 4-(trifluoromethyl)benzoate (1.1 g, 7.9 mmol) as the photochemical sensitizer. The (E)-isomers were released from the 10% AgNO$_3$ silica gel with 50 mL of 30% ammonium hydroxide(aq) and 50 mL DCM by stirring for 10 minutes. The suspension was filtered, the organics separated, dried (MgSO$_4$) and concentrated to give 500 mg of a pale yellow oil. This crude mixture was subjected to column chromatography (2:1 pentane:Et$_2$O; starting material Rf=0.23) securing 106 mg of the minor isomer (Rf=0.31) and 262 mg of the major isomer (Rf=0.14).

Preparation of (E)-2-(Cyclooct-4-enyloxy)ethyl 4-methylbenzenesulfonate (5)

The major isomer of (E)-2-(cyclooct-4-enyloxy)ethanol (180 mg, 1.1 mmol), tosyl chloride (262 mg, 1.4 mmol), and triethylamine (214 mg, 2.1 mmol) were combined in acetonitrile (6 mL). Reaction progress was monitored by TLC (1:1 hexanes:EA; starting material Rf=0.50 and desired product Rf=0.84). After 2 hours stirring at room temperature, the reaction mixture was filtered and concentrated by rotary evaporation. The crude mixture was subjected to column chromatography (1:1 hexanes:ethyl acetate) to give 298 mg of (E)-2-(cyclooct-4-enyloxy)ethyl 4-methylbenzenesulfonate (5), a 84% yield.

Preparation of (E)-5-(2-Fluoroethoxy)cyclooct-1-ene ($6^{19F}$)

(E)-2-(Cyclooct-4-enyloxy)ethyl 4-methylbenzenesulfonate (19 mg, 58.6 µmol) diluted in THF (1 mL) was treated with a tetrabutylammonium fluoride in THF (123 µL of 1 M solution). Reaction progress was monitored by TLC (2:1 pentane:Et$_2$O; starting material Rf=0.62 and desired product Rf=0.92). After stirring for 2 hours, the mixture was concentrated and the resulting amber oil subjected to column chromatography (silica gel, pentane) isolating 9.2 mg of (E)-5-(2-fluoroethoxy)cyclooct-1-ene ($6^{19F}$ (91.1%)).

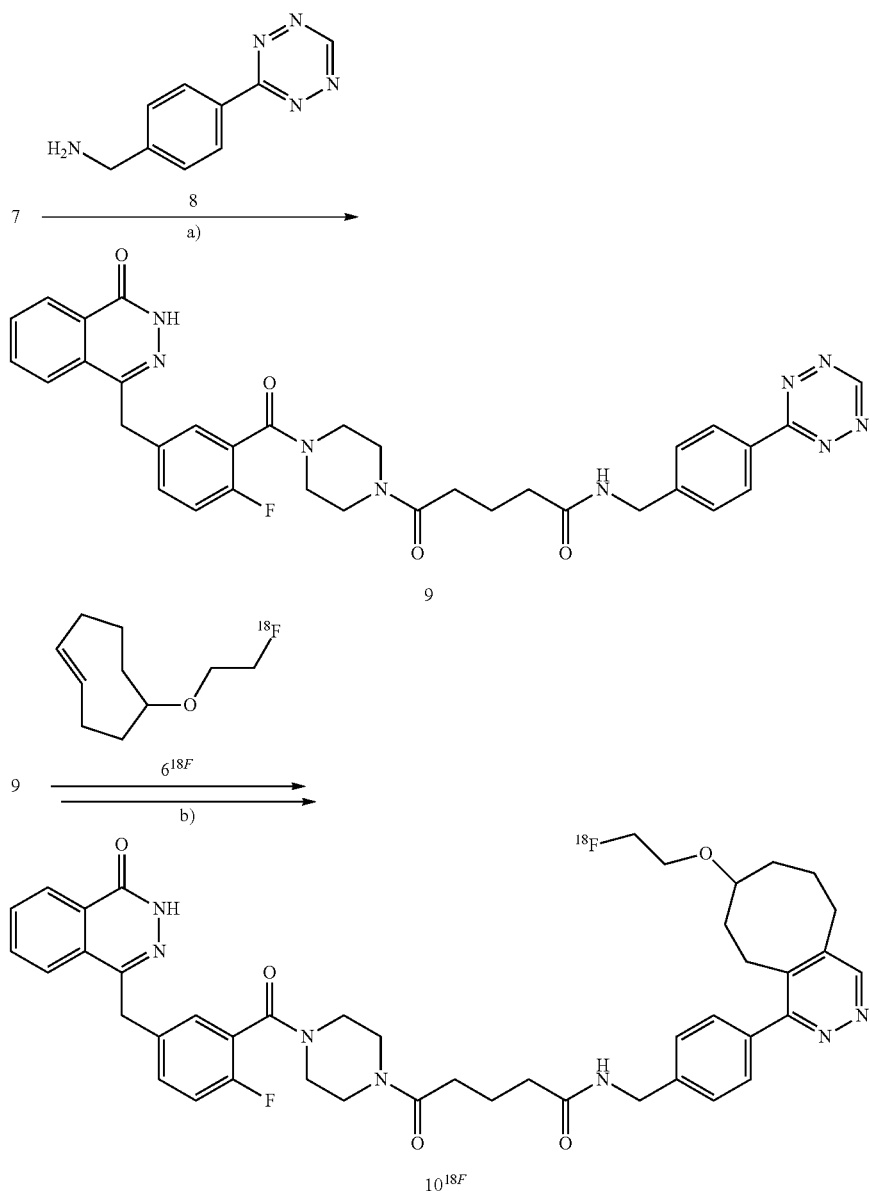

Synthetic scheme for the synthesis of radiolabeled AZD2281-$^{18}$F ($10^{18F}$). Reagents and conditions: a) polystyrene-bound DCC, Et$_3$N, CH$_2$Cl$_2$, RT, 7 h, 25%; b) CH$_2$Cl$_2$, RT, 3 min, 60%.

Preparation of AZD2281-Tz (9)

Cyclohexylcarbodiimide polystyrene resin (127 mg, 2.3 mmol/g) was added to a solution of 4-[[4-Fluoro-3-(4-(5-oxopentanamide) piperazine-1-carbonyl)phenyl]methyl]-2H-phthalazin-1-one 7 (70 mg, 0.15 mmol) in dichloromethane (10 mL) and the resulting mixture was stirred gently for 7 hours at room temperature. Subsequently, tetrazine amine (8) (55 mg, 0.29 mmol) and triethylamine (81 µL, 0.58 mmol) was added and the mixture stirred for another 60 minutes, before the reaction mixture was filtered and volatiles removed in vacuo. The crude material was purified via HPLC, yielding the title compound as a pink solid (24 mg, 37 µmol, 25%).

Preparation of 1-AZD2281-$^{19}$F ($10^{19F}$)

A solution of AZD2281-Tz (9) in DMSO (10 µL, 1 mM, 0.01 µmol) was added to ($6^{19F}$) (10 uL, 1 mM in DMSO, 0.01 µmol) and agitated for 30 minutes, before the crude reaction mixture was purified via HPLC-chromatography. HRMS-ESI [M+H]+m/z calcd. for [C44H47F2N7O5]+ 792.368, found 792.3690.

Preparation of 1-AZD2281-$^{16}$O ($10^{16O}$)

A solution of AZD2281-Tz (9) in DMSO (10 µL, 1 mM, 0.01 µmol) was added to 4 (10 uL, 1 mM in DMSO, 0.01 µmol) and agitated for 30 minutes, before the crude reaction mixture was purified via HPLC-chromatography. HRMS-ESI [M+H]+m/z calcd. for [C44H48FN7O6]+790.3723, found 790.3707.

Preparation of 1-AZD2281-$^{18}$O ($10^{18O}$)

A solution of HPLC purified 1-AZD2281-$^{18}$F ($10^{18F}$) was allowed to stand at room temperature for 48 h to allow all radioactive $^{18}$F to decay. HRMS-ESI [M+H]+m/z calcd. for [C44H48FN7O5$^{18}$O]+792.3765, found 792.3753.

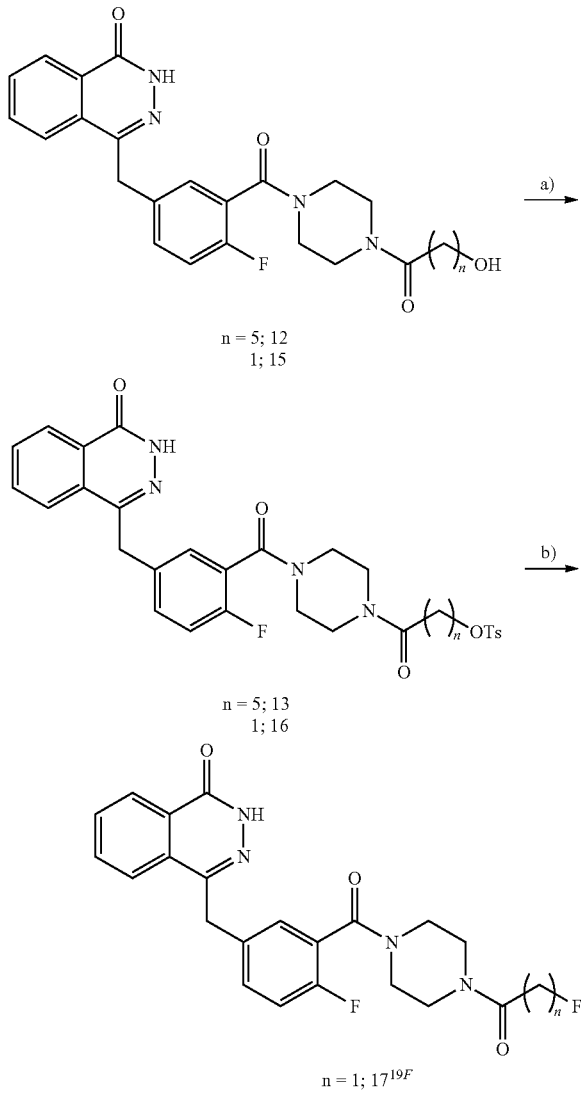

Synthetic scheme for the synthesis of conventionally fluorinated AZD2281 derivatives. Reagents and conditions: a) TsCl, Et$_3$N, CH$_2$Cl$_2$, RT, overnight, 24% for (13) and 32% for (16); b) NaF, CH$_3$CN, 40° C., 6 h, 16%.

Preparation of 4-[[4-Fluoro-3-((6-hydroxyhexanoyl) piperazine-1-carbonyl)phenyl]methyl]-2H-phthalazin-1-one (12)

4-[[4-Fluoro-3-(piperazine-1-carbonyl)phenyl]methyl]-2H-phthalazin-1-one (11) (250 mg, 0.68 mmol), HBTU (337 mg, 0.89 mmol) and triethylamine (285 µL, 1.18 mmol) were added to a solution of 6-hydroxyhexanoic acid (180 mg, 1.36 mmol) in DMF (3.0 mL) and the reaction mixture was stirred at room temperature for 60 minutes, before dichloromethane (8 mL) and water (8 mL) were added, the organic phase separated and washed with water (3×8 mL). The organic phase was dried over MgSO$_4$, volatiles removed in vacuo and the resulting crude material purified via HPLC, yielding the title compound as a clear solid (55.6 mg, 0.12 mmol, 17%).

Preparation of 4-[[4-Fluoro-3-((6-tosylhexanoyl) piperazine-1-carbonyl)phenyl]methyl]-2H-phthalazin-1-one (13)

Triethylamine (29 µL, 0.21 mmol) was added to a solution of p-toluenesulfonyl chloride (20 mg, 0.10 mmol) and 4-[[4-Fluoro-3-((6-hydroxyhexanoyl)piperazine-1-carbonyl) phenyl]methyl]-2H-phthalazin-1-one (12) (25 mg, 0.052 mmol) in dichloromethane (5 mL), the reaction mixture was stirred at room temperature overnight and purified via HPLC, yielding the title compound as a clear solid (7.8 mg, 0.01 mmol. 24%).

Preparation of 4-[[4-Fluoro-3-((2-hydroxyacetyl) piperazine-1-carbonyl)phenyl]methyl]-2H-phthalazin-1-one (15)

4-[[4-Fluoro-3-(piperazine-1-carbonyl)phenyl]methyl]-2H-phthalazin-1-one (11) (86 mg, 0.24 mmol), HBTU (116 mg, 0.30 mmol) and triethylamine (164 µL, 1.18 mmol) were added to a solution of 2-hydroxyacetic acid (36 mg, 0.48 mmol) in DMF (1.5 mL) and the reaction mixture was stirred at room temperature for 40 minutes, before dichloromethane (4 mL) and water (4 mL) were added, the organic phase separated and washed with NaOH (0.2 M, 3×4 mL) and water (3×4 mL). The organic phase was dried over MgSO$_4$, volatiles were removed in vacuo and the resulting crude material was purified via HPLC, yielding the title compound as a clear solid (24.3 mg, 0.06 µmol, 50%).

Preparation of 4-[[4-Fluoro-3-((2-tosyl-acetyl)piperazine-1-carbonyl)phenyl]methyl]-2H-phthalazin-1-one (16)

Triethylamine (53 µL, 0.38 mmol) was added to a solution of p-toluenesulfonyl chloride (36 mg, 0.19 mmol) and 4-[[4-Fluoro-3-((2-hydroxyacetic acid)piperazine-1-carbonyl)phenyl] methyl]-2H-phthalazin-1-one (15) (40 mg, 0.094 mmol) in dichloromethane (5 mL), the reaction mixture was stirred at room temperature overnight and purified via HPLC, yielding the title compound as a clear solid (34 mg, 0.06 mmol. 32%).

Preparation of 2-AZD2281-$^{19}$F ($17^{19F}$)

Freshly dried NaF (8.4 mg, 0.2 mmol) was added to a solution of 4-[[4-fluoro-3-((2-tosyl-acetyl)piperazine-1-carbonyl)phenyl]methyl]-2H-phthalazin-1-one (16) (10 mg, 0.02 mmol) in dry acetonitrile (2 mL) and was stirred for 6 hours at 40° C. before the reaction mixture was purified via HPLC, yielding the title compound as a clear solid (1.2 mg, 2.8 µmol, 16%).

B. Radiochemistry

4-(4-fluoro-3-(4-(2-18F-fluoroacetyl)piperazine-1-carbonyl)benzyl)phthalazin-1 (2H)-one ($17^{18F}$)

[$^{18}$F]-F$^-$, n.c.a. (no carrier added), (~77 MBq, 2.4±0.9 mCi) in H$_2$$^{18}$O (~150 µL), 250 µL of a 75 mM tetrabutylammonium bicarbonate ("Bu$_4$NHCO$_3$) solution in water, and 750 µL of MeCN were combined in a 10-mL test tube and heated (microwave) to 98° C. under a stream of argon. At 4, 8 and 12 minutes, 1 mL of MeCN was added and evaporated off. To the dried [$^{18}$F]-F$^-$ (n.c.a.)/$^n$Bu$_4$NHCO$_3$ was added 100 µL of a 35 mM solution of tosylate (16) in dimethylformamide and heated to 40° C. for 10 minutes. To remove unreacted [$^{18}$F]-fluoride, this mixture was filtered through an Alumina-N cartridge (100 mg, 1 mL, Waters) to give 16 µCi in the filtrate. HPLC coinjection of a sample of (17$^{19F}$) with an aliquot of this filtrate demonstrated formation of the desired product (17$^{18F}$) in 30 minutes and 0.8% dcRCY.

2-$^{18}$F-(E)-5-(2-Fluoroethoxy)cyclooct-1-ene (6$^{18F}$)

2-$^{18}$F-(E)-5-(2-Fluoroethoxy)cyclooct-1-ene ($^{18}$F-TCO) was prepared using Synthra RN Plus automated synthesizer (Synthra GmbH, Hamburg, Germany) operated by Synthra-View software in an average time of 40 minutes. The target well was charged with [$^{18}$F]-F$^-$, n.c.a., (~1110 MBq, 30±10 mCi) in H$_2$$^{18}$O (150 µL), 250 µL of a 75 mM tetrabutylammonium bicarbonate (TBAB) solution in water, and 200 µL of MeCN. The synthesizer reagent vials were filled as follows: A2 with MeCN (350 µL), A3 with tosylate (5) (4.0 mg, 12.3 µmol) in DMSO (400 µL), A5 with DMSO (50 µL), and B2 with H$_2$O (800 µL). The [$^{18}$F]-F-/TBAB solution was transferred to Reaction Vessel #1 and dried by azeotropic distillation of the acetonitrile/water solution by heating to 60° C. under reduced pressure and a flow of argon to achieve ~310 mbar for 2 minutes followed by 98° C. and 270 mbar for 4 minutes. Reaction Vessel #1 was cooled to 50° C., tosylate (5) in DMSO (400 µL) added, the reaction vessel pressurized to 2000 mbar, and heated to 90° C. for 10 minutes. Cooled to 30° C., the mixture was filtered through an Alumina-N cartridge (100 mg, 1 mL, Waters) into Reaction Vessel #2. The Alumina-N cartridge was washed with DMSO (50 µL) and the combined filtrates were diluted with water (800 µL). This solution was subjected to preparative HPLC purification. (61$^{8F}$) was collected (tR=10.1 min) in 4-5 mL of solvent, isolated by C18 solid phase extraction and eluted with DCM (600 µL) to give 7.7±3.4 mCi of 618F in 44.7±7.8% (n=16) decay-corrected radiochemical yield (dcRCY) in an average time of 41 min from the end of drying of [$^{18}$F]-F$^-$ (n.c.a.). Analytical HPLC demonstrated >93% radiochemical purity of (6$^{18F}$).

1-AZD2281-$^{18}$F (10$^{18F}$).

To the above described (6$^{18F}$)/DCM solution was added AZD2281-Tz (9) (7 µL of 18.5 mM DMSO solution, 0.13 µmol) and stirred at rt for 3 minutes. The mixture was concentrated with a gentle stream of argon, reconstituted in 1:1 MeCN/H$_2$O (to a volume of 1.3 mL), subjected to preparative HPLC purification (tR=6.0 min) and isolated by C18 solid phase extraction. Elution with MeOH (600 uL) followed by evaporation of solvent provided 2.3±0.8 mCi (n=3) of (10$^{18F}$).

1-AZD2281-$^{18}$O (10$^{18O}$).

A solution of HPLC purified 1-AZD2281-$^{18}$F (10$^{18F}$) was allowed to stand at room temperature for 48 hours to allow all radioactivity to decay. HRMS-ESI [M+H]+m/z calcd. for [C44H48FN7O518O]+792.3765, found 792.3753.

C. PARP1 IC$_{50}$ Determination.

To assess the effect of the TCO/Tz ligand on target affinity, a colorimetric assay was employed to measure PARP1 activity.

A commercially available colorimetric assay (Trevigen, Gaithersburg, Md.) was used to measure PARP activity in vitro in the presence of inhibitors. Tenfold dilutions of compounds (6$^{19F}$), (10$^{19F}$), (17$^{19F}$) (final concentration 4 µM to 0.04 nM) and (9) (1 µM to 0.1 nM) were incubated with 0.5 units PARP HSA for 10 minutes in histone-coated 96-well plates. All experiments were carried out in triplicate. Control samples did not contain inhibitor and background measurement samples did not contain PARP1. All reaction mixtures were adjusted to a final volume of 50 µL and a maximum final concentration 0.4% DMSO in assay buffer. The remainder of the assay was performed according to the manufacturer's instructions. PARP activity was measured by absorbance at 450 nm in each well using a Safire2 microplate reader. IC$_{50}$ values were calculated using the Prism software package.

Figure 4:
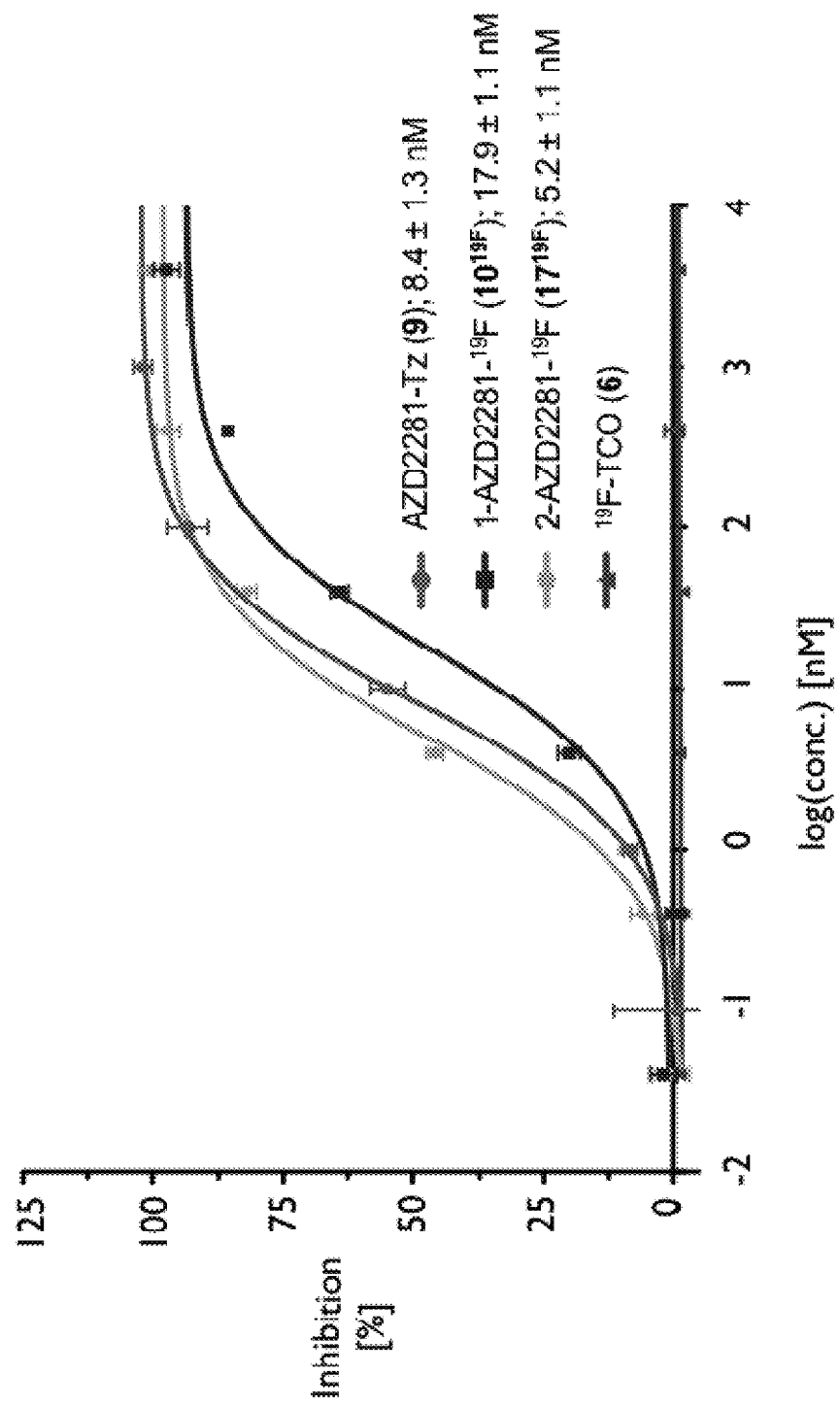
FIG. 4 is a line graph representing $IC_{50}$ curves for PARP1 inhibitors (9) (circle), ($10^{19F}$) (square), ($17^{19F}$) (inverted triangle) and trans-cyclooctene ($6^{19F}$) (triangle).

The published value for AZD2281 is 5 nm (K. A. Menear et al., *J. Med. Chem.* 2008, 51, 6581-6591; and D. V. Ferraris, *J. Med. Chem.* 2010, 53, 4561-4584), identical to what we observed in our assay. Conventionally fluorinated (17$^{19F}$) had an IC$_{50}$ value of 5.2±1.1 nm, consistent with the small side group. Compound (9) showed an IC$_{50}$ value of 8.4±1.3 nm, quite remarkable given the bulkier side chain. Cycloaddition fluorinated (10$^{19F}$) had an IC$_{50}$ value of 17.9±1.1 nm (FIG. 4), still in the low double-digit nanomolar range and likely sufficient for imaging purposes. These findings are also in agreement with previous results showing that modification of AZD2281 at the piperizine position only minimally perturbs the ability to bind PARP1 (T. Reiner, S. Earley, A. Turetsky, R. Weissleder, *Chem Bio Chem* 2010, 11, 2374-2377).

Example 3

A. Synthesis
Materials and Methods.

Unless otherwise noted, all reagents were purchased from Sigma-Aldrich (St. Louis, Mo.) and used without further purification. Cyclohexylcarbodiimide polystyrene resin was purchased from EMD biosciences (Gibbstown, N.J.). Magnetic amine-decorated beads were purchased from Invitrogen (Dynabeads® M270 amine, Carlsbad, Calif.). Oregon Green-Tz[1], 4-[[4-fluoro-3-(piperazine-1-carbonyl)phenyl]methyl]-2H-phthalazin-1-one (AZD2281, (4)), AZD2281-Tz (5) and (E)-2-(Cyclooct-4-enyloxy)ethyl 4-methylbenzenesulfonate (2) were synthesized as described earlier (K. A. Menear et al., *J. Med. Chem.* 2008, 51, 6581-6591; and E. J. Keliher et al., *Chem Med Chem* 2010, DOI: 10.1002/cmdc.201000426). $^{18}$F-Fluoride (n.c.a.) in $^{18}$O-enriched water was purchased from PETNET (Woburn, Mass.). Automated synthesis of $^{18}$F-labeled trans-cyclooctene was carried out using a Synthra RN Plus automated synthesizer (Synthra GmbH, Hamburg, Germany) operated by Synthra-View software. For non-radioactive compounds, LC-ESI-MS analysis and HPLC-purifications were performed on a Waters (Milford, Mass.) LC-MS system. For LC-ESI-MS analyses, a Waters XTerra® C18 5 µm column was used. Preparative high performance liquid chromatography (HPLC) runs for synthetic intermediates utilized an Atlantis® Prep T3 OBD™ 5 µM column (eluents 0.1% TFA (v/v) in water and MeCN; gradient: 0-1.5 min, 5-100% B; 1.5-2.0 min 100% B). For radiolabeled compounds, preparative scale HPLC purification was achieved using a Machery-Nagel Nucleodur C18 Pyramid 250×10 mm Vario-Prep column (60:40 0.1% trifluoroacetic acid (v/v) in water-acetonitrile (MeCN) at 5.5 mL·min$^{-1}$) with a 254 nm UV detector and radiodetector connected in series. Analytical HPLC of radiolabeled compounds was performed employing a Grace VYDAC (218TP510) C18 reversed-phase column (eluents 0.1% TFA (v/v) in water and MeCN; gradient: 0-17 min, 5-60% B; 17-21 min, 60-95% B; 21-24 min, 95%

B; 24-25 min, 95-5% B; 25-30 min, 5% B; 2 mL·min-1) with a dual-wavelength UV-vis detector and a flow-through gamma detector connected in series. HyperSep C18 cartridges were purchased from Thermo Electron (Bellefonte, Pa.) and Sep-pak VAC Alumina-N cartridges from Waters (Milford, Mass.). High-resolution electrospray ionization (ESI) mass spectra were obtained on a Bruker Daltonics APEXIV 4.7 Tesla Fourier Transform mass spectrometer (FT-ICR-MS) in the Department of Chemistry Instrumentation Facility at the Massachusetts Institute of Technology. $IC_{50}$ assays were analyzed using a Tecan (Männedorf, Switzerland) Safire2 microplate system. All kinetic data were analyzed using Prism 4 (GraphPad, La Jolla, Calif.) for Mac.
Preparation of Magnetic Trans-Cyclooctene Scabenger Resin.

One problem during the synthesis of $^{18}F$-radiolabeled compounds is that in most cases large amounts of precursors are used to efficiently react with small quantities of $^{18}F$. The resulting mixtures are typically purified by HPLC to remove the excess starting material, which in most cases will compete with the radiolabeled probe for the targeted binding sites. To avoid lengthy HPLC purifications, we designed a trans-cyclooctene resin to "pull out" excess tetrazine-conjugated AZD2281 derivatives from the reaction mixture (FIG. 5A).

Magnetic amine-decorated beads (400 μL, approx. 12 mg) were separated from the storage buffer and washed with a mixture of PBS 1× and DMF (3×400 μL, PBS 1×/DMF=1/1) and were resuspended in PBS 1×/DMF (400 μL, 1/1). Trans-Cyclooctene 1 was added (40 μL, 75 mM in DMF) and the mixture stirred gently for 2.5 h. Subsequently, the beads were washed with a mixture of PBS 1× and DMF (4×400 μL, PBS 1×/DMF=1/1), resuspended in PBS 1×/DMF (400 μL, 1/1) and stored at 4° C. (FIG. 5B).

Preparation of 2-[$^{18}F$]-(E)-5-(2-Fluoroethoxy)cyclooct-1-ene (3)

2-[$^{18}F$]-(E)-5-(2-Fluoroethoxy)cyclooct-1-ene (3) was synthesized similar to methods described earlier (E. J. Keliher et al., *Chem Med Chem* 2010, DOI: 10.1002/cmdc.201000426; FIG. 5C). Briefly, 2-[$^{18}F$]-(E)-5-(2-fluoroethoxy)cyclooct-1-ene ($^{18}F$-TCO) was prepared using Synthra RN Plus automated synthesizer (Synthra GmbH, Hamburg, Germany) operated by SynthraView software in an average time of 40 minutes. The target well was charged with [$^{18}F$]-F-, n.c.a., (~1110 MBq, 30±10 mCi) in $H_2^{18}O$ (150 μL), 250 μL of a 75 mM tetrabutylammonium bicarbonate (TBAB) solution in water, and 200 μL of MeCN. The synthesizer reagent vials were filled as follows: A2 with MeCN (350 μL), A3 with tosylate 2 (4.0 mg, 12.3 μmol) in DMSO (400 μL), A5 with DMSO (50 μL), and B2 with $H_2O$ (800 μL). The [$^{18}F$]-F-/TBAB solution was transferred to Reaction Vessel #1 and dried by azeotropic distillation of the acetonitrile/water solution by heating to 60° C. under reduced pressure and a flow of argon to achieve ~310 mbar for 2 minutes followed by 98° C. and 270 mbar for 4 minutes. Reaction Vessel #1 was cooled to 50° C., tosylate (2) in DMSO (400 μL) added, the reaction vessel pressurized to 2000 mbar, and heated to 90° C. for 10 minutes. Cooled to 30° C., the mixture was filtered through an Alumina-N cartridge (100 mg, 1 mL, Waters) into Reaction Vessel #2. The Alumina-N cartridge was washed with DMSO (50 μL) and the combined filtrates were diluted with water (800 μL). This solution was subjected to preparative HPLC purification. $^{18}F$-TCO (3) was collected (tR=10.1 min) in 4-5 mL of solvent, isolated by C18 solid phase extraction and eluted with DCM (600 μL), concentrated with a gentle stream of argon, reconstituted in 1:1 MeCN/$H_2O$ (to a volume of 1.0 mL) to give 6.7±2.2 mCi of ($3^{18F}$) in 37.0±1.9% (n=4) decay-corrected radiochemical yield (dcRCY) in an average time of 41 minutes from the end of drying of [$^{18}F$]-F- (n.c.a.). Analytical HPLC demonstrated >93% radiochemical purity (RCP) of ($3^{18F}$).

Preparation of 18F-AZD2281 (6)

$^{18}F$-AZD2281 (6) was synthesized similar to methods described earlier (E. J. Keliher et al., *Chem Med Chem* 2010, DOI: 10.1002/cmdc.201000426). AZD2281-Tz (5) (7 μL of an 18.5 mM DMSO solution (0.13 μmol)) was added to a solution of ($3^{18F}$) (2.3 mCi) and stirred at room temperature for 3 minutes. This results in quantitative conversion of $^{18}F$-TCO (3), yielding a mixture of $^{18}F$-AZD2281 (6) and excess AZD2281-Tz (5; FIG. 5E). The solution was treated with 4 mole equivalents of TCO-beads (0.52 μmol TCO), vortexed and allowed to stand for 5 minutes. The beads were removed by magnetic separation and the reaction mixture analyzed by HPLC, 92.1±0.4% dcRCY and 96.0±2.0% (n=3) RC purity. Treatment of this solution for 5 minutes with the TCO-decorated scavenger resin (4 mol equiv of TCO) removed unreacted AZD2281-Tz with minimal loss (approximately 4%) of radiolabeled compound (6). Magnetic removal of the beads provided (6) in (92.1 0.4)% dcRCY, which was then reconstituted in a medium suitable for animal injection (FIG. 5A). HPLC analysis of the reaction mixture before and after treatment with the TCO-decorated scavenger resin shows that the absorption peak resulting from AZD2281-Tz completely vanishes, whereas the activity peak resulting from $^{18}F$-AZD2281 persists (FIG. 5F).

B. Loading of Magnetic TCO Scavenger-Resin.

Loading of the magnetic TCO-scavenger resin was determined by separating both the beads and their unmodified precursors (each 50 μL, approx. 1.5 mg) from the storage solution (PBS 1×/DMF=1/1) and storage-buffer, respectively and washing with a mixture of PBS 1× and DMF (3×50 μL, PBS 1×/DMF=1/1). They were resuspended in a solution of Oregon Green-Tz (50 μM, 50 μL; PBS 1×/DMF=1/1), and stirred gently for 50 min. The amount of Oregon Green-Tz "pulled out" of the solution by trans-cyclooctene was measured by determining the solution's absorption at 504 nm and the loading (specific-non-specific adsorption) calculated to be 13 μmol/g.

C. Assays

Cell Culture

MDA-MB-231 and MDA-MB-436 cells were obtained from ATCC (Manassas, Va.) and cultured in RPMI 1640 supplemented with 10% fetal bovine serum, L-glutamine, and penicillin/streptomycin (each Invitrogen, Carlsbad, Calif.) at 37° C. and 5% $CO_2$.

PARP1 Expression Analysis

PARP1 expression in MDA-MB-231 and MDA-MB-436 cells was determined by immunoblot analysis. Cells were lysed in RIPA buffer (Cell Signaling Technology, Danvers, Mass.) containing complete protease inhibitors (Roche Applied Science, Indianapolis, Ind.), and protein concentration was quantified using the microBCA assay (Pierce, Rockford, Ill.). Lysates containing SDS loading buffer were boiled for 10 minutes, proteins were separated by SDS-PAGE, then transferred to PVDF membranes using the iBlot (Invitrogen, Carlsbad, Calif.). Membranes were blocked overnight at 4° C. using 5% milk (for PARP1 blot) and 5% BSA (for GAPDH blot) in TBSTween 20, probed with antibodies against PARP1 (XY-7, Santa Cruz Biotechnologies, Santa Cruz, Calif.) and GAPDH (Millipore, Temecula, Calif.) for 1 hour at room temperature, then washed with PBS. Membranes were then incubated with appropriate secondary antibodies conjugated to HRP for 1 hour at room temperature. After washing, membranes were incubated with SuperSignal West Pico chemiluminescent substrate (Pierce, Rockford, Ill.) for 5 minutes, and exposed to film.

The $IC_{50}$ value of $^{18}$F-AZD2281 against PARP1 was determined to be (17.9 1.1) nm in biochemical assays using the isolated enzyme (AZD2281 itself has an $IC_{50}$ value of 5 nM). This demonstrates PARP1 to be an ideal target for the rapid screening of $^{18}$F-labeled inhibitors, as it can accommodate relatively large prosthetic groups that do not affect binding affinity.

Cell Based Assays

For cell based assays, MDA-MB-231 and MDA-MB-436 cells (50,000 cells/well) were seeded into 96-well plates and allowed to attach over night at 37° C. and 5% C02. Ten-fold dilutions of AZD2281 4 (final concentration: 10 µM to 0.01 nM) were added to the wells and incubated for 10 minutes, before 5 µCi of 18F-AZD2281 6 (5 µL, 0.2 µCi/µL) were added and the cells incubated for 20 minutes. Then, the medium was replaced and waited for another 10 minutes, before the cells were washed with PBS (3×100 µL) and subjected to gamma-counting.

Figure 6:
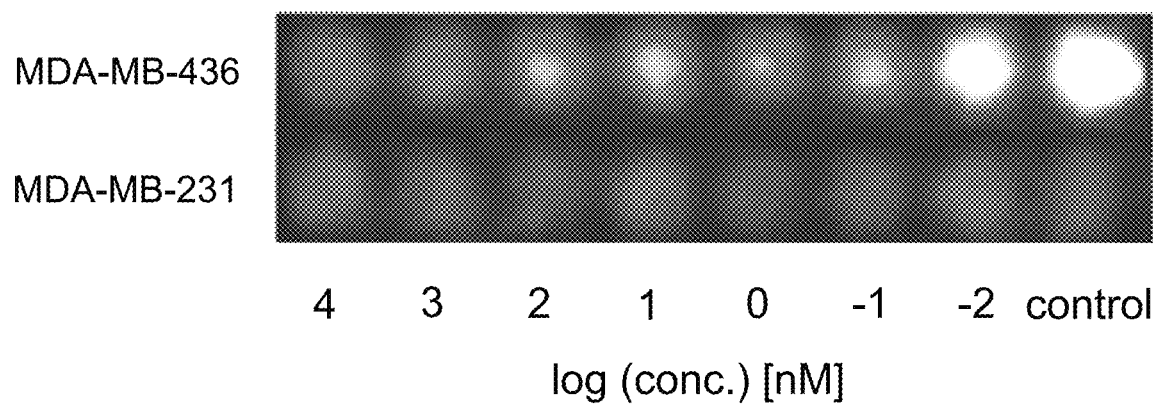
FIG. 6 shows the results of competitive in vitro inhibition assays with $^{18}$F-AZD2281. Cells containing either a high (MDA-MB-436) or a low amount of PARP1 (MDA-MB-231) were treated with 5 mCi of $^{18}$F-AZD2281 in the presence of different concentrations of AZD2281 (10 μM-0.01 nM). After the cells were washed, cell-associated activity was determined by measurement of the g-radiation. For the control measurement, no unlabeled AZD2281 was added.

Cellular uptake of $^{18}$F-AZD2281 was determined by quantification of the remaining activity after incubation and washing of the adherent cells. $^{18}$F-AZD2281 was shown to be cell-permeable and its uptake inhibitable upon addition of excess nonradioactive AZD2281 (FIG. 6). Uptake of $^{18}$F-AZD2281 was lower for MDA-MB-231 cells than for MDA-MB-436 cells, which correlates with protein expression of PARP1 in the respective cell lines.

Mice

Non-tumor bearing Nu/Nu mice were injected with ($6^{18F}$) and used for organ distribution immediately after injection over a time period of 2 hours. Tumor-bearing mice received s.c. injections with 5×106 MDA-MB-436 cells (American Type Culture Collection) in Matrigel (BD Biosciences) into each flank and underwent imaging 7 days later (injection of ($6^{18F}$) and immediate imaging over a time period of 2 hours). All mice were anesthetized (isoflurane 1.5%; $O_2$ 2 L/min) during imaging with a gas delivery system integrated into a multimodal imaging cartridge. All animal experiments were approved by Massachusetts General Hospital's Institutional Review Committee.

Images were acquired on the Siemens Inveon PET-CT. Each PET acquisition was 120 minutes in duration. PET was reconstructed from 600 million coincidental 511 keV photon counts on a series of LSO (lutetium oxyorthosilicate) scintillating crystals. Counts were rebinned in 3D by registering photons spanning no more than 3 consecutive rings and reconstructed into sinograms using a high resolution Fourier Rebin algorithm. Sinograms also yielded a 3D mapping of positron signal using a 2D filtered back-projection algorithm and a Ramp filter with a Nyquist cut-off of 0.5. Datasets were anisotropic matrices containing 128×128×159 pixels, measuring 0.796 mm/pixel in the z direction and 0.861 mm/pixel in the x and y directions. Calibration of PET signal preceded all scans by scanning an 8.0 cm in diameter cylindrical phantom containing a known amount of $^{18}$F isotope. Data are expressed as standard uptake values (SUV), which normalizes activity measurements to body weight and injected activity.

For anatomic reference of PET signal, x-rays were projected over 360 degrees to create a computed tomographic (CT) image. X-ray projections had a cone beam angle of 9.3 degrees and a power of 80 keV. A 500 µA anode source was located 347 mm from the center of rotation and x-rays were incident on a CCD detector containing 2048 transaxial and 3072 axial pixels. Projections were calibrated using 70 dark and 70 light images, interpolated bilinearly, processed through a Shepp-Logan filter, and then reconstructed using a filtered back projection algorithm. CT datasets were isotropic matrices with a total of 512×512×768 pixels measuring 110 µm³. During CT acquisition, iodine contrast was infused into the tail vein at a rate of 35 µL/min to enhance intravascular contrast. Projections were acquired at end expiration of the respiratory cycle using a BioVet gating system (M2M Imaging, Cleveland, Ohio) and total CT acquisition time was ~10 minutes. PET-CT fusion and image analysis were performed using Inveon Research Workplace 3.0 (Siemens). Three-dimensional visualizations were produced with the DICOM viewer OsiriX (The OsiriX foundation, Geneva, Switzerland).

Figure 7A:
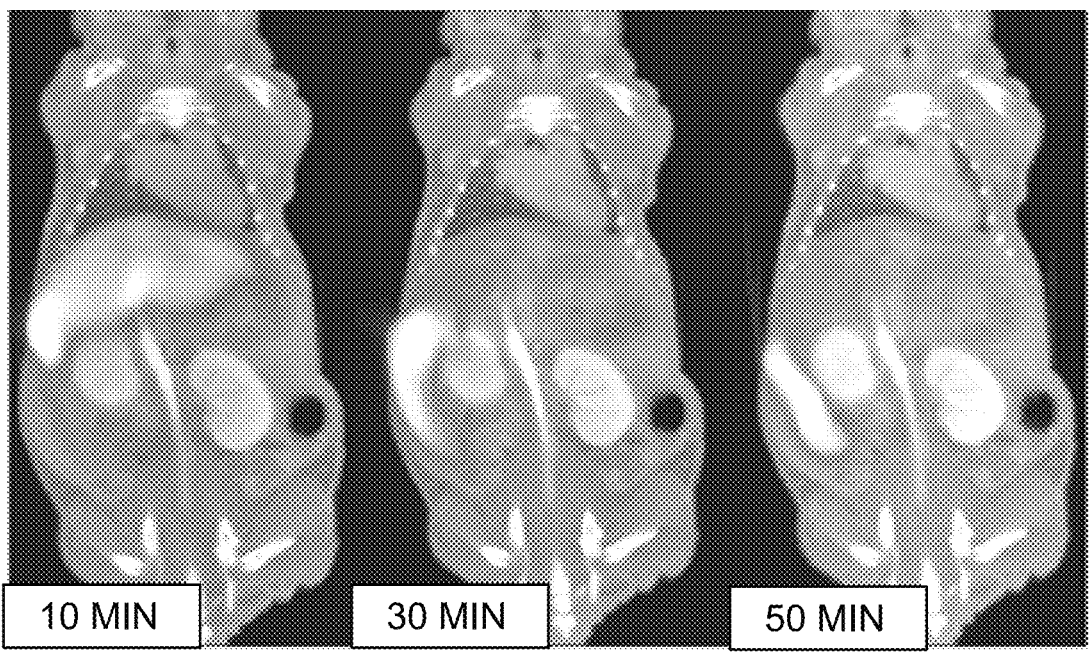
FIGS. 7A-C illustrate an in vivo evaluation of $^{18}$F-AZD2281.
Figure 7B:
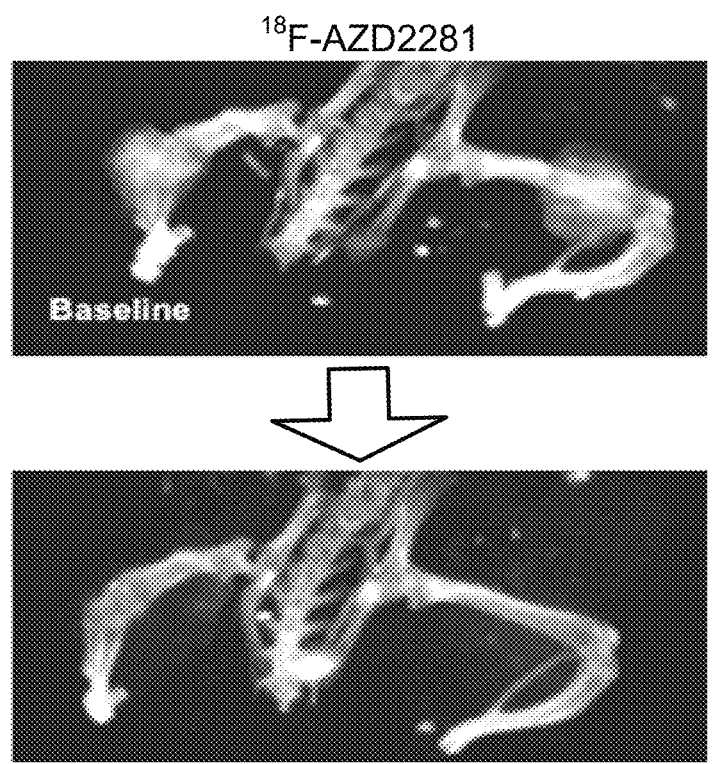
Figure 7C:
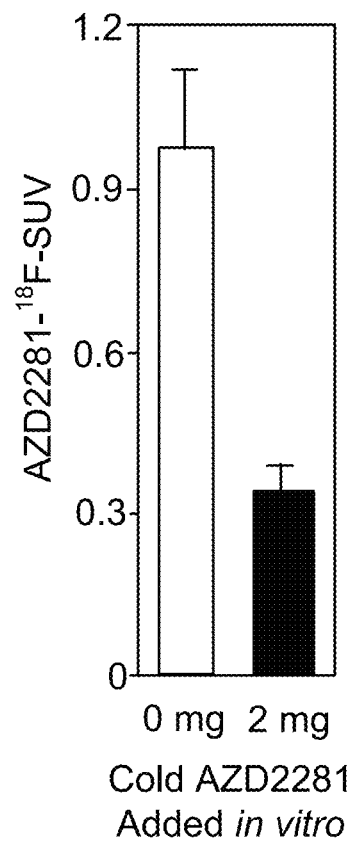

FIG. 7A displays the distribution of the PET probe in the Nu/nu mice at 10, 30, and 50 minutes. The images clearly show initial localization of the probe to be mainly in liver, gall bladder, and intestines, consistent with hepatobiliary excretion. After 50 minutes (FIG. 7A), the majority of the probe had left the bloodstream ($t_{1/2}$=6 min) and was excreted through the large intestines. FIG. 7B shows a three-dimensional reconstruction of a tumor-bearing mouse injected with 30 mCi of $^{18}$F-AZD2281. Uptake in the tumors is clearly visible. Immediately after imaging, the mice were injected with 1 mg AZD2281 BID. Re-injection of 30 mCi of $^{18}$F-AZD2281 confirmed inhibition of the probe s uptake into the tumors (FIGS. 7B and 7C). Therefore, owing to the rapid decay rate of $^{18}$F, each mouse serves as its own control on subsequent days of imaging, facilitating direct comparisons of standardized uptake value (SUVs).

Example 4. Non-Invasive Monitoring of Treatment Response Using AZD2281-$^{18}$F $^{18}$F-AZD2281 was synthesized as described herein. Nu/Nu mice bearing either A2780 tumors (treatment response) or A2780, Paca2, Panc1 and SKOV3 (differential uptake) were injected with the hot probe (500-750 Ci) and imaged ~1.5 hours thereafter. Treatment consisted of injection of 0.5-1.0 mg AZD2281 (Olaparib) 18 hours before imaging (ip, interperitoneal) or ~1.5-3.5 hours before imaging (iv, intravenous). Uptake was determined non-invasively by drawing SUVs (Standard Uptake Values).

Figure 8A:
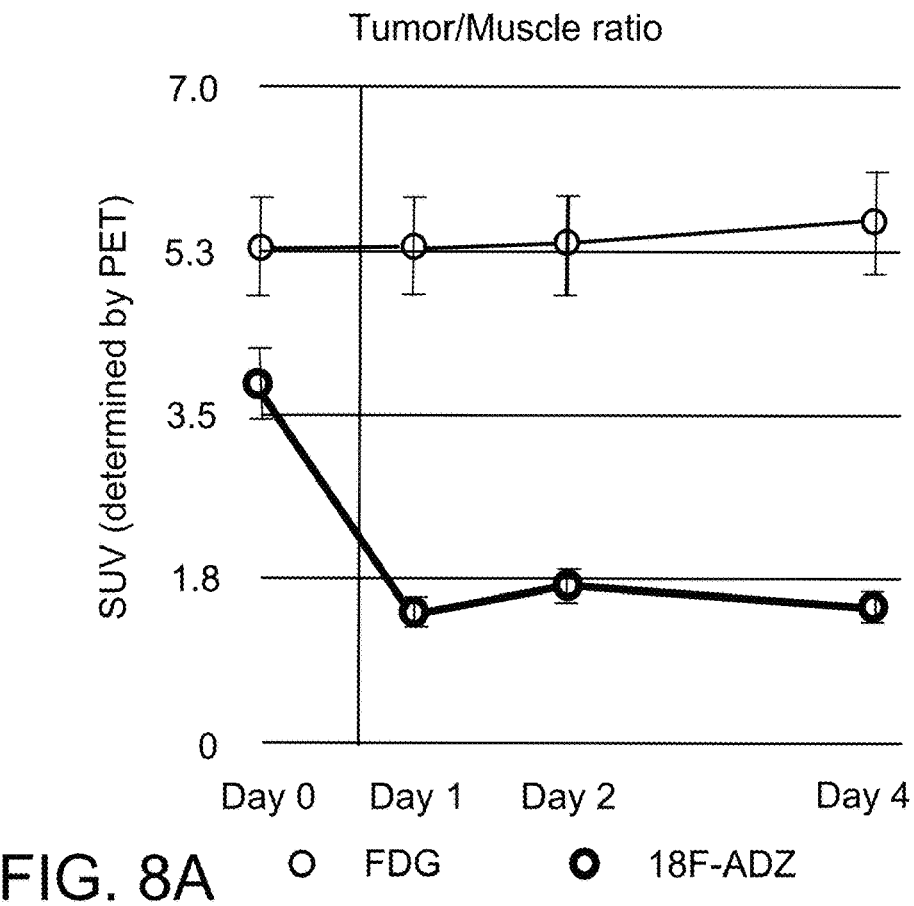
FIG. 8A illustrates the ability of FDG and $^{18}$F-AZD2281 to distinguish between muscle and tumor cells.
Figure 8B:
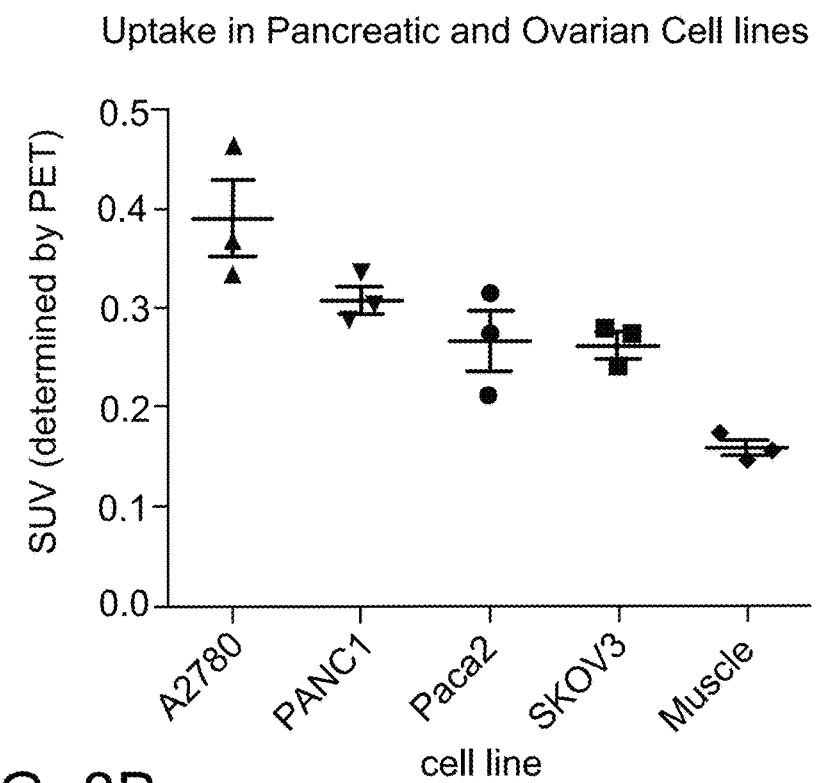
FIG. 8B shows the relative uptake of $^{18}$F-AZD2281 activity of different ovarian and pancreatic tumors (A2780 and SKOV3=ovarian, PANC1 and PACA2=pancreatic).

FIG. 8A shows that FDG, the current gold standard in cancer imaging, is not able (based on tumor/muscle signal intensity) to distinguish between treated untreated tumors. Injection of Olaparib (AZD2281; Tx=treatment, starting between day 0 and day 1) into tumors lets the signal of $^{18}$F-AZD2281 drop, which is a major advantage in terms of predicting if a human tumor will respond to treatment with Olaparib or other PARP inhibitors. FIG. 8B shows the relative uptake of $^{18}$F-AZD2281 activity of different ovarian and pancreatic tumors (A2780 and SKOV3=ovarian, PANC1 and PACA2=pancreatic). This data indicates that a wide variety of tumors respond to $^{18}$F-AZD2281 treatment, and that those cancers can be detected using the compounds provided herein.

Example 5. Comparison of Uptake and Expression

RAW 264.7, Panc-1, MIAPaca2, A2780, OVCAR429, UCI 101, UCI 107, SKOV-3, OVCAR-3, and OV-90 cells (200 µL, 35,000 cells/mL) were each seeded in their respective growth medium on 96-well plates and allowed to attach for 48 hours. They were incubated with AZD2281-BODIPY FL (2 µL, 100 µM) for 20 minutes (37° C.) before the medium was removed and cells were washed (1×, medium, 200 µL). Cells were then fixed with paraformaldehyde (4% in PBS) and washed with ice cold PBS/0.1% Triton X-100/0.5% bovine serum albumin (3×200 µL, 3rd wash left for 30 min). Cells were incubated with anti-PARP-1/2 Rab (1:50; SCBT, Santa Cruz, Calif.) at 4° C. overnight. Cells were washed with PBS/0.1% Triton X-100 (3×200 µL) before stained with secondary IgG-Cy5 Gab (1:100; Millipore, Billerica, Mass.) for 3 h at 4° C. Cells were then washed with PBS (1×, 200 µL), stained with Hoechst (Invitrogen, Carlsbad, Calif.) and blue whole cell stain (Thermo Scientific, Waltham, Mass.) for 30 minutes at room temperature, and washed with PBS (3×, 200 µL) before imaging and quantification of the respective fluorescence signals.

FIG. 9A shows that AZD2281-BODIPY FL (green—inner halo) localizes with the nucleus (as confirmed with the red signal (inner most signal), Chromatin (essentially a DNA stain)). This is where PARP1, the target, is located. It does not go into the perinuclear region (the rest of the cell), as shown by the blue stain, which basically colors the cell walls. The composite combines all colors. FIG. 9B plots the amount of fluorescence present in cells using AZD2281 and a PARP1/PARP2 antibody. The more PARP1/PARP2 there is in a cell line, the more AZD2281-BODIPY FL is taken up by the cell. FIG. 9C shows the same data as FIG. 9B, but plots the data differently. This figure shows that the R2 (a measure for correlation) is very high, indicating that AZD2281-BODIPY FL not only targets PARP1, but targets it quantitatively, allowing for an accurate measurement of the amount of PARP1 in a given cell line (or, in a clinical setting, tumor environment).

Example 6. Life Cell Imaging

For in vitro kinetic studies, HT1080 cells were labeled with a 1 µM concentration of AZD2281 fluorophore conjugate in cell culture medium and imaged on an inverted Deltavision epifluorescence microscope using a 37° C. heated stage and 5% $CO_2$ atmosphere for various times. After subtracting the background fluorescence, the data were fitted to an exponential association curve. For clearance, cells were labeled at 1 µM for 1 hour until the cells had reached equilibrium. Cells were washed twice in cell culture media and imaged continuously (BODIPYFL conjugate) or after various time points (BODIPY578 and BODIPY650). The loss in fluorescence was fitted to a biexponential decay curve.

Figure 10:
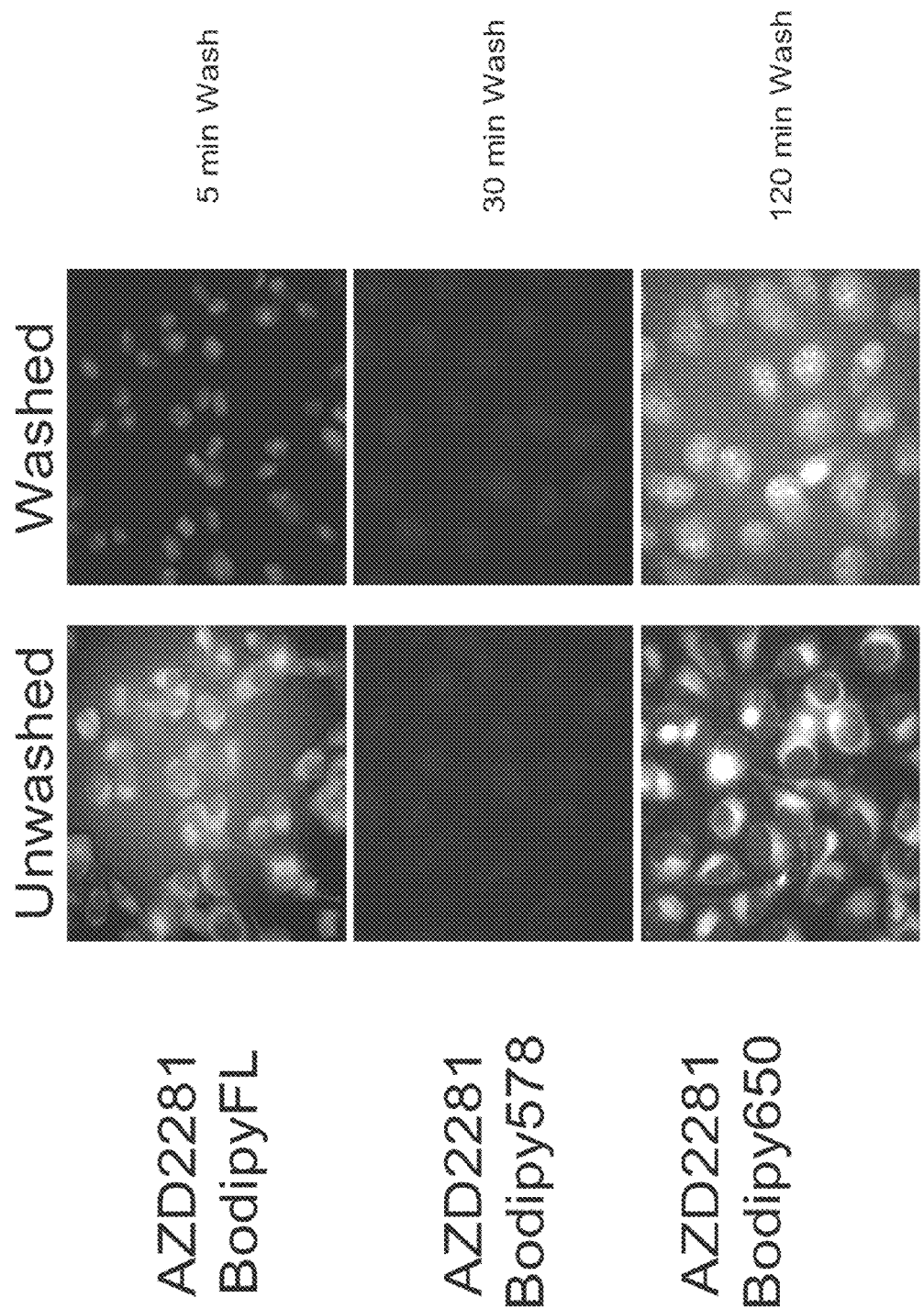
FIG. 10 illustrates the life cell imaging of three different AZD2281 fluorophores.
Figure 11:
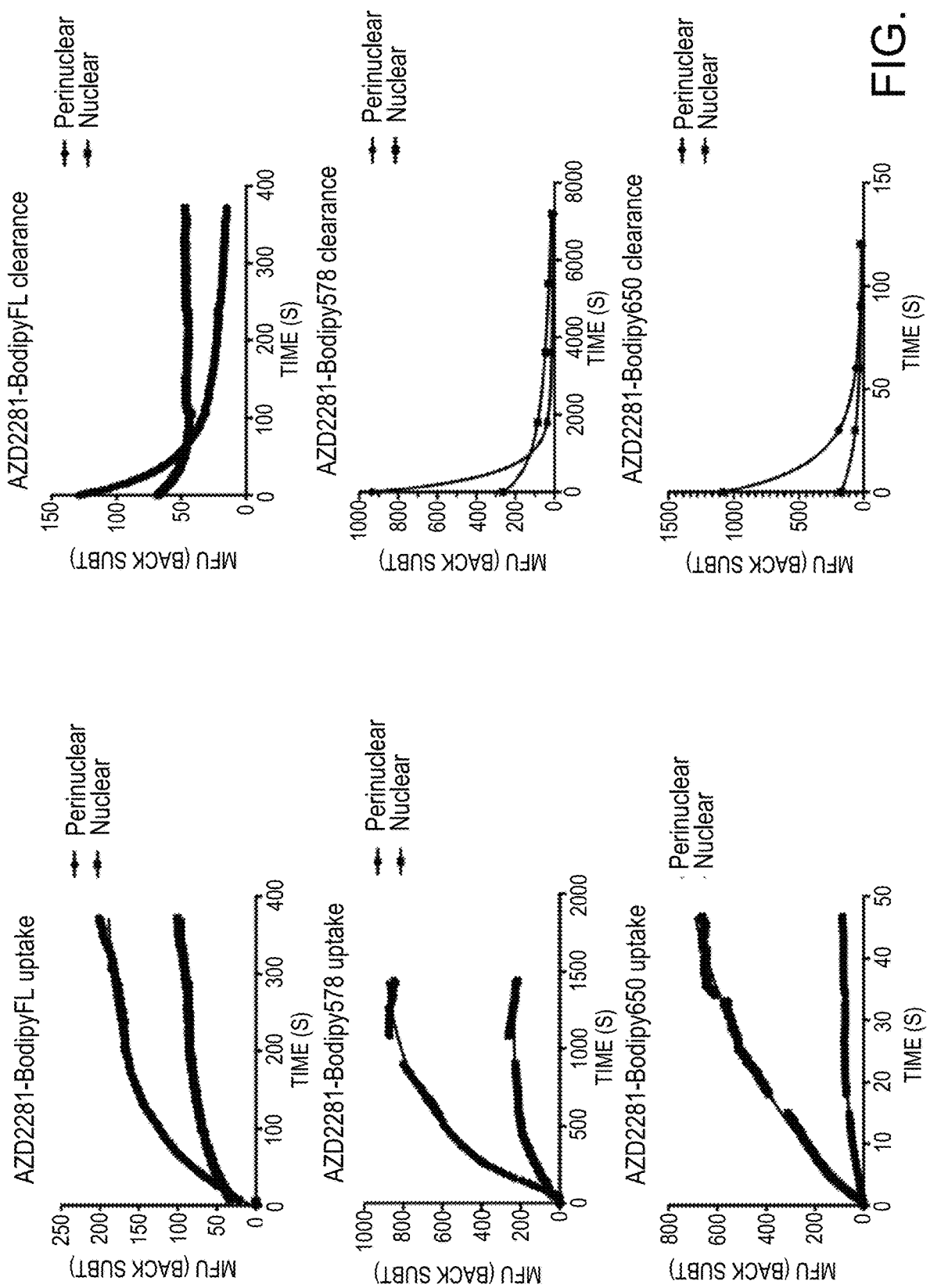
FIG. 11 shows line graphs illustrating the life cell imaging of three different AZD2281 fluorophores.

In FIGS. 10 and 11, three different AZD2281 fluorophores were tested using life cell imaging. The cells are not fixed, but in their most natural state (as close as possible to using intravital imaging). First, the compounds were added to the medium surrounding the cells, the compounds entered the cells, and when the medium (which contained AZD2281-fluorophores) was replaced, the AZD2281-fluorophores were washed out of the perinuclear region (where PARP1 is not located). However, the compounds were retained in the nuclear region (where PARP1 is located), showing that all the compounds tested work in an in vitro setting. Table 2 details the properties of the compounds tested, obtained by serial imaging techniques.

TABLE 2

| AZD2281 | Uptake | Clearance (weighted) | Properties |
|---|---|---|---|
| BODIPYFL | Perinuclear = 1.2 min<br>Nucleus = 1.1 min | Perinuclear = 1.7 min<br>Nucleus = slow (remeasure) | MW = 640 |
| BODIPY578 | Perinuclear = 5.4 min<br>Nucleus = 3.6 min | Perinuclear = 6.9 min<br>Nucleus = 23.8 min | MW = 677 |
| BODIPY650 | Perinuclear = 21.2 min<br>Nucleus = 8.3 min | Perinuclear = 12.8 min<br>Nucleus = slow (remeasure) | MW = 895 Da |

Example 7. Cellular Resolution of Fluorescent AZD2281 Derivatives

For the in vivo studies, mice with window chambers were implanted with 1 million HT-1080 cells expressing H2B-apple fluorescence protein. 75 nmol of AZD2281-BODIPYFL were dissolved in 75 µL of 1:1::DMAC:solutol and 75 µL of PBS and injected via tail vein. Images of the vessels were taken using a 20× water immersion objective on a laser scanning confocal microscope while the mouse was anesthetized with isoflurane. After 1 hour, the non-specific uptake of the probe cleared revealing nuclear uptake of the probe.

Figure 12:
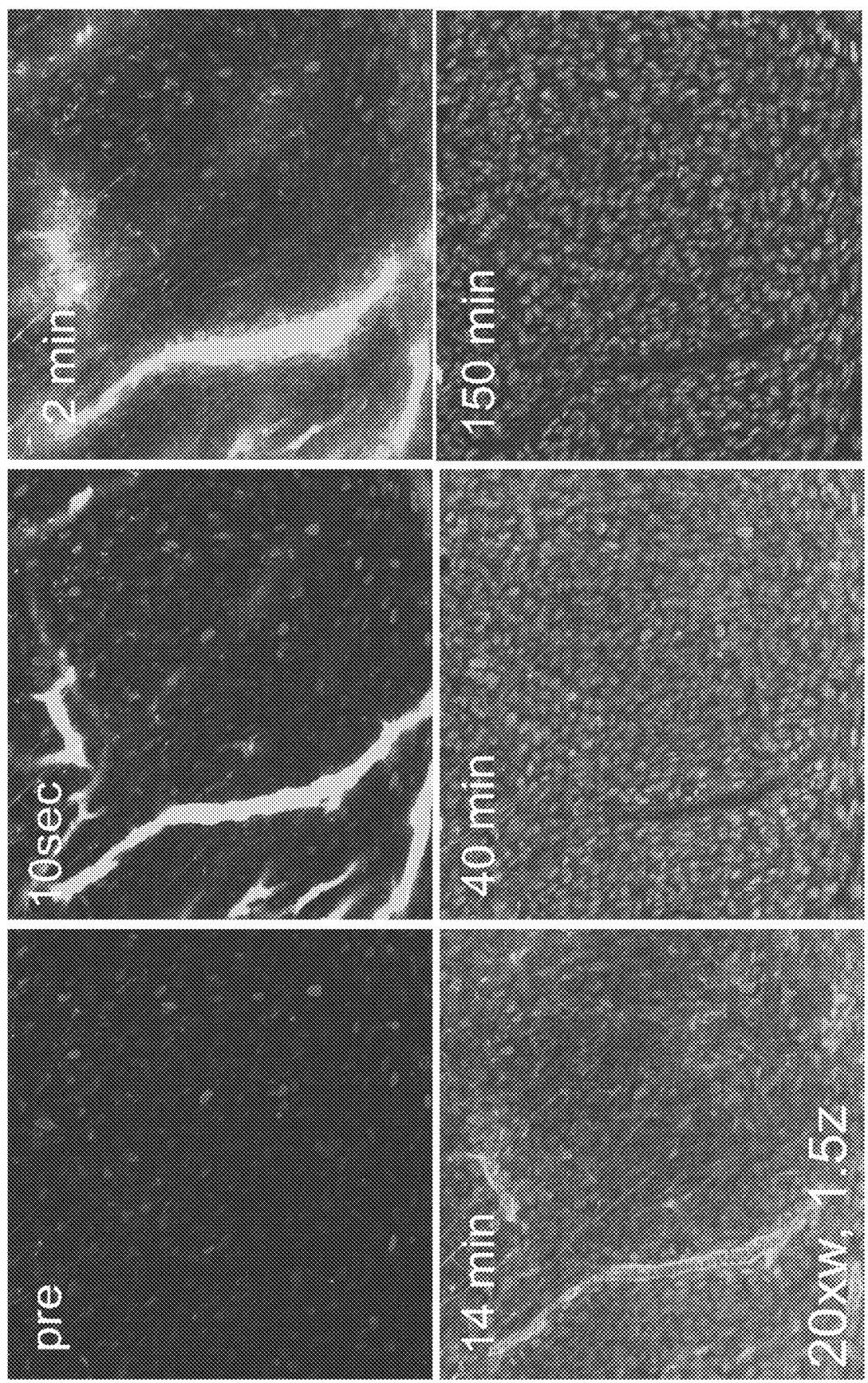
FIG. 12 shows the behavior of AZD281-BODIPY FL in vivo following iv administration of the compound into a mouse.

FIG. 12 shows the behavior of AZD281-BODIPYFL in vivo. The compound was injected into a mouse by iv (10 seconds). The compound is first observed in the vascular system (where it was injected) and then concentrates in each and every tumor cell of the tumor (red dots). This data shows the ability of the compound to bind to PARP1 in vivo.

Example 8. Selective Tumor-Uptake of Fluorescent AZD2281 Derivatives

For $^{18}F$-AZD2281 standardized uptake values, five Nu/Nu mice each received four subcutaneous injections containing SKOV-3, MIA Paca2, A2780, or Panc-1 cells in the flanks and shoulders (2.5×10⁶ cells in 100 µL 70:30 PBS/BD matrigel per injection) (BD Biosciences, Bedford, Mass.). Tumors were allowed to grow for two weeks before imaging. 75 nmol of AZD2281-BODIPYFL were dissolved in 75 µL of 1:1::DMAC:solutol and 75 µL of PBS and injected via tail vein. The agent was allowed to circulate and clear for 45 minutes, before the mice were sacrificed, tumors and muscle tissue excised and the relative fluorescence uptake of tissues quantified against mice which were injected with just 1:1::DMAC:solutol.

Figure 13A:
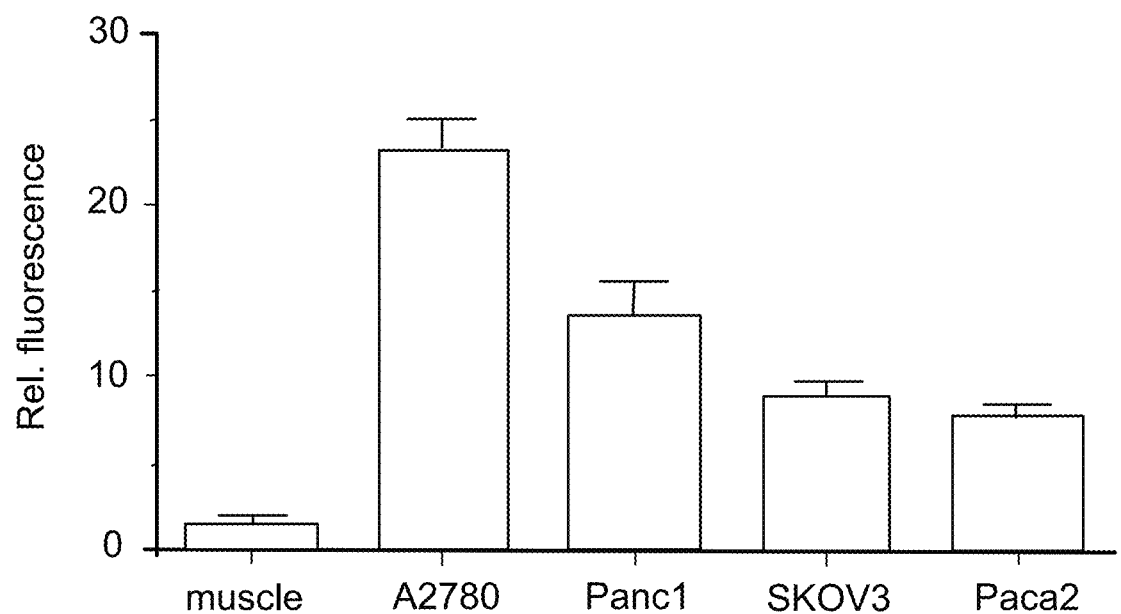
FIG. 13A is a bar graph illustrating the uptake of AZD2281-BODIPY FL on a global level.
Figure 13B:
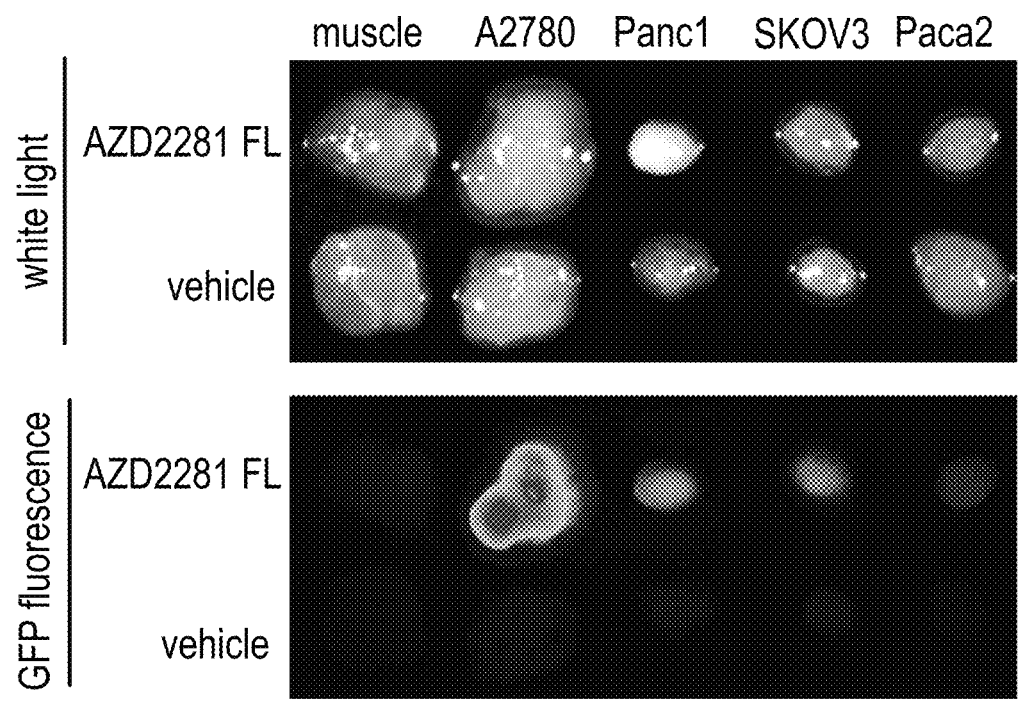
FIG. 13B shows the uptake of AZD2281-BODIPY FL on a cellular level.

FIG. 13 shows that the uptake of AZD2281-BODIPY FL is not just specific on a cellular level, but also globally. Tumors have higher PARP1 levels than other tissue, and this is shown by the fact that very little of the compound gets taken up by muscle cells compared to the tumor tissues. This data corresponds well to the in vitro data described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula:

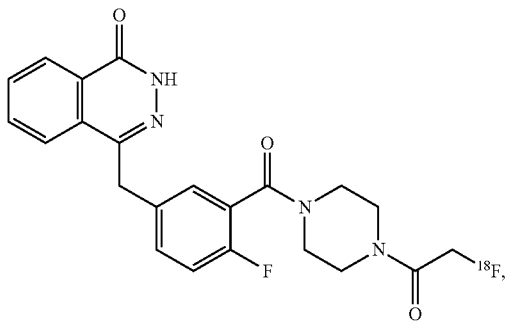

or a pharmaceutically acceptable salt thereof.

2. A pharmaceutical composition comprising the compound of claim 1, or a pharmaceutically acceptable salt thereof, and a pharmaceutically acceptable carrier or diluent.

3. A method for detecting a cancer in a subject, the method comprising:
(a) administering to the subject an effective amount of a compound which is:

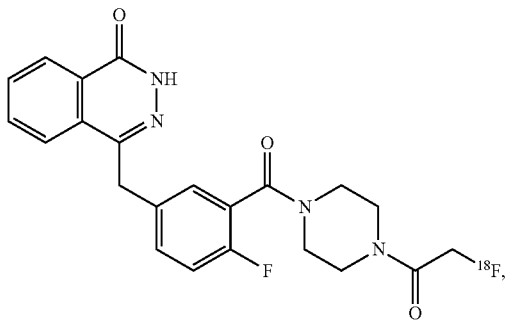

or a pharmaceutically acceptable salt thereof; and
(b) detecting the compound in the subject.

4. The method of claim 3, wherein detecting the compound comprises performing a detection method selected from the group consisting of fluorescence detection, chemiluminescence detection, magnetic resonance imaging, nuclear magnetic resonance imaging, positron emission tomography, and single-photon emission computed tomography.

5. The method of claim 3, wherein the cancer is selected from the group consisting of: pancreatic cancer, ovarian cancer, and breast cancer.

6. The method of claim 3, wherein the compound is administered before and after surgical removal of the cancer.

7. A method for monitoring the cancer treatment of a patient, the method comprising:
(a) administering to the patient, prior to a treatment, an effective amount of a compound which is:

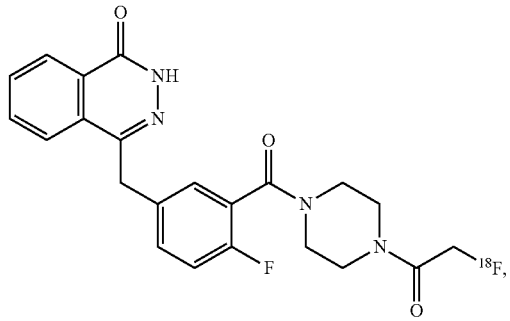

or a pharmaceutically acceptable salt thereof, and imaging the patient;
(b) administering to the patient, at a point following treatment, an effective amount a compound which is:

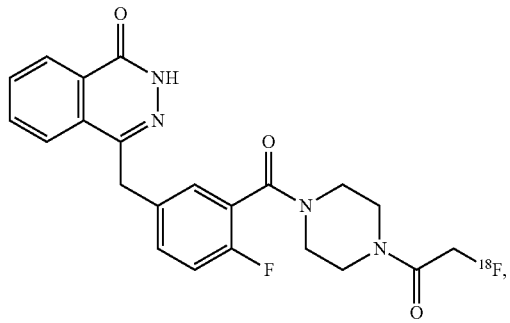

or a pharmaceutically acceptable salt thereof, and imaging the patient; and
(c) comparing the image collected in step (a) with the image collected in step (b) to monitor the treatment.

8. The method of claim 7, wherein the treatment further comprises administration of an anti-cancer agent.

9. The method of claim 7, wherein the method further comprises: administering to the patient an effective amount of a compound which is:

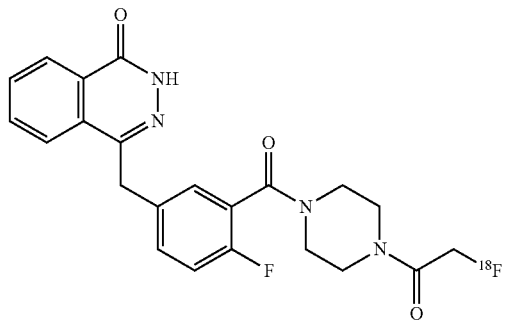 [SMILES: O=C(C[18F])N1CCN(C(=O)c2cc(Cc3n[nH]c(=O)c4ccccc34)ccc2F)CC1]

or a pharmaceutically acceptable salt thereof, during treatment and imaging the patient.

* * * * *